US011090171B2

(12) United States Patent
Radspieler

(10) Patent No.: US 11,090,171 B2
(45) Date of Patent: Aug. 17, 2021

(54) APPARATUS, SET AND METHOD FOR CREATING A PLASTER IMPRESSION OF A LIMB STUMP OF A PATIENT FOR MANUFACTURING A PROSTHESIS SHAFT AND ADAPTOR

(71) Applicant: Romedis GmbH, Neubeuern (DE)

(72) Inventor: Andreas Radspieler, Neubeuern (DE)

(73) Assignee: ROMEDIS GMBH, Neubeuern (DE)

( * ) Notice: Subject to any disclaimer, the term of this patent is extended or adjusted under 35 U.S.C. 154(b) by 640 days.

(21) Appl. No.: 15/553,955

(22) PCT Filed: Feb. 26, 2016

(86) PCT No.: PCT/EP2016/054143
§ 371 (c)(1),
(2) Date: Aug. 25, 2017

(87) PCT Pub. No.: WO2016/135320
PCT Pub. Date: Sep. 1, 2016

(65) Prior Publication Data
US 2018/0036144 A1 Feb. 8, 2018

(30) Foreign Application Priority Data

Feb. 26, 2015 (DE) .............................. 102015102798
Mar. 16, 2015 (DE) .............................. 102015103864
(Continued)

(51) Int. Cl.
*A61F 2/60* (2006.01)
*A61F 2/50* (2006.01)
(Continued)

(52) U.S. Cl.
CPC .............. *A61F 2/5046* (2013.01); *A61F 2/60* (2013.01); *A61F 2002/501* (2013.01);
(Continued)

(58) Field of Classification Search
CPC .... A61F 2/5046; A61F 2/60; A51F 2002/501; A51F 2002/505; A51F 2002/5052–5053;
(Continued)

(56) References Cited

U.S. PATENT DOCUMENTS 1,335,475 A   3/1920  Bergman
3,889,301 A * 6/1975  Bonner, Sr. ........... A61F 2/7843
                                                         623/37
(Continued)

FOREIGN PATENT DOCUMENTS

CA   2730895 A1   1/2010
DE   9303681 U1   7/1993
(Continued)

OTHER PUBLICATIONS

International Search Report: PCT/EP2016/054143 dated Jun. 1, 2016.
(Continued)

*Primary Examiner* — Jeffrey M Wollschlager
*Assistant Examiner* — Xue H Liu
(74) *Attorney, Agent, or Firm* — Millman IP Inc.

(57) ABSTRACT

The present invention relates to a medical apparatus (100) for use in manufacturing a plaster impression of limb stump, in particular of a lower stump, wherein the apparatus (100) comprises a pressure vessel (1) with a fluid chamber of pressure chamber (DK) for receiving or storing a fluid (F) being under pressure, wherein the pressure vessel (1) is limited against an exterior (Ä), wherein the pressure vessel (1) comprises an insertion opening (9) for the insertion of a limb stump (KS) into the interior (I) of the pressure vessel (1) and a fluid-tight membrane (5) made of two materials, which are arranged to form or limit the fluid chamber or the pressure chamber (DK). In addition, the present invention relates to a system (300) having a medical apparatus (100)
(Continued)

and at least one contact surface (111). Furthermore, the present invention relates to a method.

26 Claims, 31 Drawing Sheets

(30) Foreign Application Priority Data

| | | | |
|---|---|---|---|
| Mar. 18, 2015 | (DE) | ............................. | 102015104070 |
| Apr. 15, 2015 | (DE) | ............................. | 102015105775 |
| Apr. 28, 2015 | (DE) | ............................. | 102015106551 |
| Apr. 30, 2015 | (DE) | ............................. | 102015106821 |
| Jun. 10, 2015 | (DE) | ............................. | 102015109198 |
| Jun. 24, 2015 | (DE) | ............................. | 102015110156 |
| Jun. 26, 2015 | (DE) | ............................. | 102015110355 |
| Aug. 28, 2015 | (DE) | ............................. | 102015114383 |
| Jan. 25, 2016 | (DE) | ............................. | 102016101257 |

(51) Int. Cl.
*A61F 2/74* (2006.01)
*A61F 2/78* (2006.01)

(52) U.S. Cl.
CPC . *A61F 2002/505* (2013.01); *A61F 2002/5052* (2013.01); *A61F 2002/5053* (2013.01); *A61F 2002/74* (2013.01); *A61F 2002/7818* (2013.01); *A61F 2002/7875* (2013.01)

(58) Field of Classification Search
CPC .......... A51F 2002/74; A51F 2002/7818; A51F 2002/7875
USPC ........................................................ 264/222
See application file for complete search history.

(56) References Cited

U.S. PATENT DOCUMENTS

| | | | |
|---|---|---|---|
| 3,962,395 A | 6/1976 | Hagglund | |
| 4,735,754 A | 4/1988 | Buckner | |
| 4,923,474 A | 5/1990 | Klasson et al. | |
| 5,314,497 A | 5/1994 | Fay et al. | |
| 5,503,543 A | 4/1996 | Laghi | |
| 5,507,836 A | 4/1996 | Pohlig | |
| 5,718,925 A * | 2/1998 | Kristinsson | A61F 2/80 425/2 |
| 5,728,165 A | 3/1998 | Brown, Sr. | |
| 5,971,729 A | 10/1999 | Kristinsson et al. | |
| 5,993,400 A | 11/1999 | Rincoe et al. | |
| D429,335 S | 8/2000 | Caspers et al. | |
| 6,136,039 A | 10/2000 | Kristinsson et al. | |
| 6,231,617 B1 | 5/2001 | Fay | |
| 6,706,364 B2 | 3/2004 | Janusson et al. | |
| 6,709,617 B2 | 3/2004 | Wu | |
| 6,923,834 B2 | 8/2005 | Karason | |
| 6,991,444 B1 | 1/2006 | Laghi | |
| 7,105,122 B2 | 9/2006 | Karason | |
| 7,410,350 B2 | 8/2008 | Horiguchi et al. | |
| 7,427,297 B2 | 9/2008 | Patterson et al. | |
| 7,655,049 B2 | 2/2010 | Phillips | |
| 8,052,760 B2 | 11/2011 | Egilsson et al. | |
| 8,317,873 B2 | 11/2012 | Doddroe et al. | |
| 8,597,368 B2 | 12/2013 | Bergmann et al. | |
| 9,050,202 B2 | 6/2015 | Bache et al. | |
| 9,283,093 B2 | 3/2016 | Alley | |
| 9,468,542 B2 | 10/2016 | Hurley et al. | |
| 9,486,333 B2 | 11/2016 | Wang et al. | |
| 9,486,334 B2 | 11/2016 | Tompkins | |
| 9,504,585 B2 | 11/2016 | Cornell | |
| 9,572,691 B2 | 2/2017 | Pacanowsky et al. | |
| 9,956,094 B2 | 5/2018 | Mahon | |
| 2001/0039159 A1 | 11/2001 | Janusson et al. | |
| 2002/0043738 A1 | 4/2002 | Wu | |
| 2004/0137178 A1 | 7/2004 | Janusson et al. | |
| 2005/0267599 A1 | 12/2005 | Bjarnason | |
| 2009/0036999 A1 | 2/2009 | Egilsson et al. | |
| 2010/0249949 A1 | 9/2010 | Bjarnason et al. | |
| 2012/0095571 A1 | 4/2012 | Gunnarsson et al. | |
| 2013/0053982 A1 | 2/2013 | Halldorsson | |
| 2014/0288668 A1 | 9/2014 | Gottlieb et al. | |
| 2015/0118338 A1 | 4/2015 | Galfione et al. | |
| 2015/0250624 A1 | 9/2015 | Mosler et al. | |
| 2015/0352775 A1 | 12/2015 | Geshlider et al. | |
| 2015/0359644 A1 | 12/2015 | Sanders et al. | |
| 2016/0166411 A1 | 6/2016 | Kelley et al. | |
| 2016/0324666 A1 | 11/2016 | Barberio | |
| 2016/0331563 A1 | 11/2016 | Kane et al. | |
| 2017/0216057 A1 | 8/2017 | Egilsson et al. | |
| 2018/0036152 A1 | 2/2018 | Klutts | |
| 2018/0235784 A1 | 8/2018 | Halldorsson et al. | |
| 2018/0296372 A1 | 10/2018 | Johnson | |

FOREIGN PATENT DOCUMENTS

| | | |
|---|---|---|
| DE | 29506829 U1 | 8/1995 |
| DE | 102006048451 A1 | 4/2008 |
| DE | 102010019405 A1 | 8/2011 |
| DE | 10 2011 117 801 A1 | 5/2013 |
| DE | 19549477 C5 | 2/2015 |
| DE | 202015100025 U1 | 2/2015 |
| DE | 102013223572 A1 | 5/2015 |
| DE | 102014011034 A1 | 1/2016 |
| DE | 102014011374 A1 | 2/2016 |
| DE | 102015106821 A1 | 9/2016 |
| DE | 102016113590 A1 | 2/2017 |
| DE | 102016107074 A1 | 10/2017 |
| DE | 202016008363 U1 | 10/2017 |
| DE | 102016110445 A1 | 12/2017 |
| DE | 102016118765 A1 | 4/2018 |
| DE | 102017106903 B3 | 7/2018 |
| DE | 102017114001 A1 | 12/2018 |
| DE | 102018128231 A1 | 5/2020 |
| EP | 0392025 B1 | 1/1994 |
| EP | 736294 A2 | 10/1996 |
| EP | 650708 B1 | 6/2000 |
| EP | 989833 B1 | 11/2003 |
| EP | 868158 B1 | 1/2005 |
| EP | 1265564 B1 | 11/2005 |
| EP | 1843291 A1 | 10/2007 |
| EP | 954258 B1 | 1/2008 |
| EP | 2705810 A1 | 3/2014 |
| EP | 2501344 B1 | 2/2015 |
| EP | 2815728 B1 | 1/2016 |
| EP | 2873393 B1 | 5/2017 |
| GB | 267988 A | 3/1927 |
| GB | 2149309 A | 6/1985 |
| GB | 2232598 A | 12/1990 |
| WO | 2004041013 A2 | 5/2004 |
| WO | 2004041132 A2 | 5/2004 |
| WO | 2008005331 A2 | 1/2008 |
| WO | 2010141960 A2 | 12/2010 |
| WO | 2011106258 A2 | 9/2011 |
| WO | 2013136284 A2 | 9/2013 |
| WO | 2014032815 A1 | 3/2014 |
| WO | 2016135320 A1 | 9/2016 |
| WO | 2017151577 A1 | 9/2017 |

OTHER PUBLICATIONS

Torres-Moreno, R. et al., "Computer-aided design and manufacture of an above-knee amputee socket," J, Biomed. Eng., 1991, vol. 13, Jan. 1991, pp. 3-9.

Tantua, Audrey T., et al., "Reduction of residual limb volume in people with transtibial amputation," JRRD, vol. 51, No. 7, 2014, pp. 1119-1126.

Sanders, Joan E., et al., "Residual limb volume change: Systematic review of measurement and management," JRRD, vol. 48, No. 8, 2011, pp. 949-986.

Zheng, YP et al., "State-of-the-art methods for geometric and biomechanical assessments of residual limbs: a review," Journal of

(56) References Cited

OTHER PUBLICATIONS

Rehabilitation Research and Development, vol. 38, No. 5, Sep./Oct. 2001, pp. 487-504.
Murdoch, George, "The "Dundee" Socket—A Total Contact Socket for the Below-Knee Amputation", Orthopedic & Prosthetic Appliance Journal, Sep. 1965, pp. 231-234.
Lee, Peter Vee Sin; et al., "Pressure casting technique for transtibial prosthetic socket fit in developing countries", JRRD, vol. 51, No. 1, 2014, pp. 101-110.
Klasson, et al., "Open Learning 94 912 Advanced Prosthetic Science (Manual 3)", University of Strathclyde Engineering, Nov. 2006.
Price, Howard L., "Molecular Orientation and Mechanical Anisotropy in Polyethylene, polypropylene, and poly (ethylene terephthalate) films", NASA Technical Note, Aug. 1969.
Bes, Femke Madelinde, Thesis for Higher Vocational Training Orthopaedic Technologist "Measurement without hands—A practical study of measurement techniques for lower leg prostheses", Fontys University of Applied Scines, Eindhoven, Sep. 1, 2005, pp. 40-45.

\* cited by examiner

APPARATUS, SET AND METHOD FOR CREATING A PLASTER IMPRESSION OF A LIMB STUMP OF A PATIENT FOR MANUFACTURING A PROSTHESIS SHAFT AND ADAPTOR

The present invention relates to an apparatus according to the preamble of claim 1. It further relates to a set according to the preamble of claim 18, method according to the preambles of claims 19, 22 and 23, further a calculation device according to the preamble of claim 24, a unit according to the preamble of claim 25, a pressurization control device according to the preamble of claim 26, an adapter according to the preamble of claim 27, a digital storage medium, a computer program product and a computer program.

Leg amputees may recover mobility using leg prostheses. Modern leg prostheses include various modules (prosthesis shaft, knee, lower leg and foot modules), which may be combined to meet the various needs of the prosthesis wearer (hereinafter referred to as wearer or patient) in terms of fundamental mobility, sport activities and aesthetic perceptions.

Some of the aforementioned modules may be standardized and possibly be provided in different sizes, lengths or other configurations, from which the respective suitable module is selected.

However, this is generally not true for the prosthesis shaft, the module of the prosthesis, which represents the connection between the mechanical replacement of the extremity and the residual limb stump (in short also referred to as stump) of the prosthesis wearer, e.g. a lower leg stump, a thigh stump or an arm stump.

In the state of the art, the prosthesis shaft is individually adapted to the stump of the eventual wearer. For this purpose, firstly, a plaster impression is produced by means of a moist plaster bandage, which will be the basis of the prosthesis shaft and determines its shape substantially.

Making the shaft of a prosthesis requires skilled craftsmanship; the question of how convenient the shaft is going to be when worn later, significantly depends on the dexterity and experience of the orthopedic technician and the further circumstances under which the plaster impression has been made.

The question as to how suitable the shaft is when worn later, also depends on the extent to which the conditions under which the plaster impression was made coincide with those under which the shaft is worn later. In practice, it is usual to take the plaster impression of the stump while the patients is standing. Thereby, the patient, being usually one-legged, stands most of the time, wherein he must regularly be o supported. The orthopedic technician can form the still moist plaster bandage around the stump of the standing patient by using his hand. In this way, he has the possibility to visualize, through touching the anatomical conditions and the situation of the relevant bone structures with regard to the stump, and to model the moist plaster bandage or the slowly drying plaster impression accordingly.

The present invention relates to the technical field of producing a plaster impression as a copy, template or model for the later prosthesis shaft of a prosthesis, preferably for the lower extremities, i.e. for a leg prosthesis, in particular a lower leg prosthesis.

An object of the present invention may be to provide an apparatus, a system and a method for use in making a plaster impression for a prosthesis shaft, or at least for an outer shaft thereof, in particular for the lower extremity.

The object according to the present invention may be achieved by an apparatus with the features of claim 1. It may also be achieved by a set with the features of claim 18, by a method with features of claim 19, 22 or 23, also by a calculation device with the features of claim 24, a unit with the features of claim 25, a pressurizing control device with the features of claim 26 and an adapter with the features of claim 27. It may also be achieved by the herein-described digital storage medium, the computer program product and the computer program.

A medical apparatus (in short: apparatus) is thus provided by the present invention which may be used in the production of a plaster impression of a limb stump, in particular a lower leg stump. This may, for example, be used as a basis for producing a lower leg prosthesis shaft, on the, only preferably standing, patient.

Thereby, the apparatus comprises a fluid container or a pressure vessel with exactly or at least one fluid chamber. This may receive or store an optionally pressurized fluid. Thereby, the pressure is above the atmospheric pressure. The fluid is a gas or a liquid, preferably air or water, since the latter two are respectively cheap and easily available.

The pressure vessel comprises a wall, which is made of at least or exactly one first material, or comprises at least one first material.

The wall of the pressure vessel limits its interior. According to the present invention, the interior of the pressure vessel is understood to be the space or volume defined by the geometry of the pressure vessel or encompassed or circumscribed by an outer wall of the pressure vessel. If the pressure vessel is, for example, cylindrical, the interior of the pressure vessel is the space delimited by the cylindrical shell surface and the two end sides or planes. If the pressure vessel is, in another example, rectangular, the space of the interior is defined by the result of the multiplication of the height, width and depth of the rectangle. In determining the interior, it is irrelevant whether or not the space corresponding to the interior is fluid-tight. The interior does not describe a fluid-tight closed space but a volume circumscribed by the wall. The space which does not belong to the interior of the pressure vessel is referred to herein as its exterior.

The pressure vessel comprises an insertion opening through which the limb stump which may in this respect, herein also be understood as the distal end of the stump instead of the whole stump, may be inserted into the interior of the pressure vessel The insertion opening may, for example, be an open end side or end plane, a passage through-opening in the wall or an opening which breaks through or interrupts the wall. In the area of the insertion opening, the interior of the pressure vessel is thus not separated from the exterior by a section of the wall. The insertion opening may lie in an insertion opening or in an insertion plane, through which the limb stump is inserted into the interior of the pressure vessel.

Furthermore, the pressure vessel comprises at least one or exactly one fluid-tight membrane. Alternatively, the pressure vessel does not have such a membrane as described further below, but only correspondingly suitable and/or provided receiving device (such as the connectors described in the following as optional) for receiving the membrane on/at the pressure vessel.

The membrane is made of or comprises a second material. The first and the second material differ from each other.

The wall is designed as a single-piece or optionally as a multiple-piece.

A multi-piece wall may comprise a plurality of moveable/displaceable sections, in order to achieve a small packaging volume of the device for transport purposes, by way of example. The medical apparatus according to the present invention with the multi-piece wall may be referred to as a mobile medical apparatus.

The adapter according to the present invention is provided and/or prepared for use in the production of a plaster impression or a data model of a limb stump, in particular a lower leg stump. The adapter comprises at least one release unit and/or a device for transmitting tensile forces, which is connected to an adherent stocking in traction closure connection or in form-fit connection, and the adherent stocking. The release unit may advantageously protect sensitive soft parts in the area of the distal end of the limb stump.

In certain exemplary embodiments according to the present invention, the adapter comprises a traction device, in particular a belt, and/or a fixing device, in particular a fixing ring, for connecting the adapter to the traction device.

The set according to the present invention, comprises at least one medical apparatus according to the present invention. It also comprises at least two membranes which differ in at least one property from one another and/or at least one weight to effect a temporary increase of the body weight of the patient or increase of the weight applied by the patient on the membrane or on a scale. The pressure vessel of the apparatus according to the present invention may thus be adapted to different body parts, patients, patient weights, patient heights, etc. by simply exchanging the membrane against another membrane. The weight, for example in the form of a belt, suspenders, backpack or the like being weighted with one weight or several partial weights, may be attached to the patient during the production of a plaster impression by the apparatus according to the present invention. It makes him "heavier" on a scale, like the weight which is attached to a diver, with the result that the limp stump penetrates deeper into the apparatus due to the increased weight applied to the membrane. It has been found out that even more precise fits for the manufactured/made plaster impression may be achieved. The weight attached to the patient may be individually determined and, for example, may amount to between 5 kg and 25 kg or between 10 kg and 20 kg. A number of partial weights of 3 kg, 4 kg, 5 kg or the like may be provided.

The adherent stocking according to the present invention, is provided and/or prepared to be pulled over a limb stump (KS) during the production of a plaster impression or of a data model of the limb stump (KS). The adherent stocking connected to the limb stump is tractionally, in particular frictionally, engaged to a surface, in particular to the surface of a membrane, at or in a pressure vessel in order to produce the plaster impression or the data model.

The set according to the present invention may at least comprises one medical apparatus according to the present invention and at least one contact surface. The apparatus is, in relation to the contact surface and when it rests on the contact surface, preferably during the production of a plaster impression or a data model of a limb stump tiltable, twistable and/or movable/displaceable.

A method according to the present invention, serves for adjusting a plaster impression to a limb stump of a patient or measuring the dimensions of the limb stump, e.g. its volume, its geometry, its surface and/or a combination thereof. Thereby, a medical apparatus according to the present invention is provided.

In addition, optionally, the pressure chamber will be or is filled with a liquid, a balloon-like closed membrane is provided inside the pressure vessel or the liquid level within the pressure chamber is adjusted or changed in such a way that the membrane is covered by liquid at least in sections thereof around the entire circumference of these sections or is convexly curved beyond the insertion opening into the exterior of the pressure vessel.

A second method according to the present invention, serves adapting a plater impression to a limb stump of a patient. In this, a moist plaster bandage wrapped around the limb stump is subjected to constant pressure per area unit until the plaster bandage is at least partly dried.

A third method according to the present invention serves for fixing the limb stump in the pressure vessel. In this the limb stump is optionally wrapped with a moist plaster bandage, wherein the wrapping, which may be referred to as a sheath, is connected to the adapter. Subsequently, the limb stump, which is optionally wrapped with a moist plaster bandage, is inserted with the adapter into the insertion opening or into the membrane. Then, the inserted limb stump is conducted or held by a holding or adjusting device connected to the adapter, in particular by a traction force. The control is effected in particular from outside the pressure vessel and/or the pressure chamber. Finally, the limb stump connected to the adapter is fixed in the pressure vessel by the adjusting device such that the limb stump is prevented, or is at least to a large extent prevented, from moving out of the insertion opening or from moving outwards. Following this fixing, the pressure chamber is filled with fluid, preferably water. In this, preferably a predetermined pressure may preferably be specifically adjusted. The predetermined pressure may be determined or may have been determined as described herein.

A further method according to the present invention serves for fixing or holding the limb stump in the pressure vessel. In this, an adherent stocking according to the present invention, is pulled over the limb stump or slid over the latter. Subsequently, the limb stump, being coated with an adherent stocking, is inserted into the pressure vessel. In the following method step, a force-closure connection, in particular a frictional-closure connection of the adherent stocking with a surface, in particular with the upper surface of the membrane, takes place in the pressure vessel. A frictional-closure connection may be an adhesion in the form of a resilient and reversible connection of the adherent stocking to a surface in the pressure vessel.

A digital, in particular a non-volatile, storage medium according to the present invention, in particular a machine-readable wearer, in particular a diskette, CD, EPROM or DVD, with electrically readable control signals may interact with a programmable computer system such that the machine-induced steps of at least one or all the method(s) according to the present invention, may be prompted.

Thereby all, some of or specific machine-induced steps of the method(s) according to the present invention may be prompted, in particular in interaction with a computer system and an apparatus according to the present invention.

A computer program product according to the present invention comprises a program code that is volatile or saved on a machine-readable medium for prompting the machine-induced steps of one or all method(s) according to the present invention when the computer program product runs on a computer. According to the present invention a computer program product can be understood as, for example, a computer program which is stored on a storage medium, an embedded system as a comprehensive system with a computer program (e.g. an electronic device with a computer program), a network of computer-implemented computer programs (e.g. a client-server system, a cloud computing system, etc.), or a computer on which a computer program is loaded, executed, saved or developed.

The term machine-readable medium as used herein denotes in certain embodiments of the present invention a medium containing data or information which is interpretable by software and/or hardware. The medium may be a data medium, like a disk, a CD, DVD, a USB stick, a flashcard, an SD card or the like.

A computer program according to the present invention comprises a program code for prompting the mechanical steps of a method(s) according to the present invention when the computer program runs on a computer. A computer program according to the present invention can be understood, for example, as a physical, ready-for-distribution software product which comprises a computer program.

It also applies for the computer program product according to the present invention and the computer program according to the present invention that all some or several of the machine-induced steps of the method(s) according to the present invention are prompted, in particular in interaction with a computer system and an apparatus according to the present invention.

The present invention also relates to a medical apparatus for use in manufacturing a plaster impression or a data model of a limb stump, in particular a lower leg, wherein the apparatus comprises a fluid container or a pressure vessel for receiving a fluid having a wall or made of a first material, wherein the fluid is water, wherein a first end side of the wall is closed, in particular fluid-tightly closed, wherein a second end side of the wall is fluid-tightly closed with a membrane made of or having a second material, wherein the fluid container or the pressure vessel, in particular in its wall, has at least one outlet for the fluid, optionally having a valve or a stopcock for opening and closing the outlet, wherein the membrane is bag-like (i.e. having a dead end, as opposed to a tube open at the top and bottom), wherein at least one, in particular central or middle, section of the membrane is preferably releasably fixed to a section of the wall by at least one connector, wherein the membrane is preferably made of or comprises a material which comprises no elasticity or, preferably, no extensibility in a first direction of the material.

The present invention also relates to a medical apparatus for use in the manufacturing of a plaster impression or a data model of a limb stump, in particular of a lower leg stump, wherein the apparatus comprises a fluid chamber (may be a pressure vessel) for a liquid, e.g. water. The fluid chamber comprises, during use of the apparatus, an upper, or first, end side and, during use, a lower, or second, end side. In the area of the second end side, the fluid chamber can be fluid-tightly closed, for example by a bottom area. The apparatus comprises a film or membrane for receiving a section of the limb stump. The membrane is fluid-tightly connected to the chamber and/or closes the latter at least at the top or at the first end side, at least in a section, fluid-tightly. The fluid chamber may optionally comprise a pressure chamber. The fluid chamber comprises optionally at least one fluid outlet, which is optionally provided with a valve or a stopcock for opening and closing the outlet. The membrane is preferably bag-like (i.e. with a dead end like a bag, as opposed to a tube open at the top and at the bottom). At least one, preferably central or middle, preferably lower or distal section of the membrane is fastened directly or indirectly, preferably releasably, by at least one connector at or to a section of a wall of the fluid chamber, for example a bottom plane thereof. The membrane is preferably made of, or comprises a material which has no (or only little) elasticity, or preferably no (or only little) extensibility, at least in a first direction of the material, preferably in a longitudinal direction of the chamber or in an inlet direction of the limb stump. Instead of having the aforementioned membrane and/or the connector, the apparatus may be designed or configured to be connected to a membrane and/or to a connector. Suitable connecting devices, e.g. at a bottom plane, may be provided.

The present invention also relates to a method for determining an additional weight when adjusting a plaster impression to a limb stump or when measuring the dimension of the limb stump of a patient. The method encompasses at least providing patient-related data once; input of the patient-related data into a determining device; determining an additional weight (in short: weight) once, with which the patient whose limb stump is inserted into the medical apparatus must be weighted, so that a pressure present/existing on the membrane, in the pressure chamber, on a section of the surface of the limb stump covered by the membrane during use of the apparatus, and/or between the membrane and the limb stump, lies in a predetermined target value range.

The present invention further relates to a computing device which is programmed, configured and/or set or installed to carry out the method according to the present invention for determining an additional weight when adjusting a plaster impression.

Embodiments according to the present invention of each of the aforementioned subject-matter may comprise one or several of the following features in any combination unless the person skilled in the art recognizes a concrete combination as technically impossible. Also the subject-matter of the dependent claims indicate embodiments according to the present invention are In all of the embodiments herein, the use of the expression "may be" and "may have" etc. is synonymous to "is preferably" or "has preferably," etc. respectively, and is intended to illustrate an embodiment according to the present invention.

Whenever numerical words are mentioned herein, the person skilled in the art will recognize or understand them as indications of numerical lower limits. Unless it leads the person skilled in the art to an evident contradiction, the person skilled in the art will comprehend the specification for example of "one" encompassing "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

In case of doubt, the person skilled in the art will understand the spatial information like "top", "bottom", "upper" or "lower", whenever they are herein mentioned, as a spatial indication with reference to the alignment in the figures appended hereto and/or of the arrangement of the medical apparatus(es) according to the present invention when used as intended.

In specific exemplary embodiments according to the present invention, the pressure chamber is a locked and/or lockable space in which the fluid may be subjected to pressure above the atmospheric pressure (in short: atmosphere) without being able to escape from this space.

In some exemplary embodiment according to the present invention, the membrane is arranged to form the pressure chamber or alternatively to delimit it, e.g., by being part, in particular by being elastic or only in one direction elastic part, of the wall of the pressure chamber.

In specific exemplary embodiments according to the present invention, the membrane serves for building, by itself (e.g. a balloon) or alternatively together with sections of the wall, a fluid-tight fluid chamber of the pressure vessel which chamber lies at least partially or completely in the interior of the pressure vessel. Since it can receive and/or hold fluid under a pressure which is above atmospheric pressure, this fluid chamber is designated herein as pressure chamber.

The terms "fluid chamber" and "pressure chamber" are interchangeable in certain exemplary embodiments according to the present invention and/or in those embodiments in which the person skilled in the art does not object thereto. What is said herein about the "pressure chamber" may also be applicable to a "fluid chamber".

In some exemplary embodiments according to the present invention, the pressure chamber then lies inside the pressure vessel when the pressure existing in the pressure chamber does not exceed a certain pressure. Deviating from this, in some embodiments according to the present invention, the pressure chamber extends also to the exterior of the pressure vessel when the pressure present/existing in the pressure chamber pressurizes the membrane such that the latter projects outwards, for example through the insertion opening, i.e. into the exterior of the pressure vessel. The pressure chamber may thus have a variable volume, which depends on the pressure present/existing in the pressure chamber. The latter does not apply to the constant inside the pressure vessel.

In some exemplary embodiments according to the present invention, a fluid may be maintained in the pressure chamber under a pressure above the atmosphere, regardless of the insertion opening penetrating through the wall.

In specific exemplary embodiments according to the present invention, the pressure chamber serves for receiving or supporting the distal end of the patient's limb stump which is inserted into the interior of the pressure vessel. Due to the fluid contained in the pressure chamber, the membrane nestles laterally or circumferentially to the distal end of the limb stump or to the entire limb stump. In this way, it may be possible to pressurize the limb stump in the area of the entire plaster bandage through the membrane with the— referring to an area unit—preferably unchanged or same pressure. The latter may be an advantageous contribution of the present invention, since the even pressurization may lead to an even modeling of the moist plaster bandage. Placing the membrane under the fluid stored in the pressure chamber may advantageously make manual modeling unnecessary or significantly reduce the necessary effort. The plaster bandage may be a standard one.

In some exemplary embodiments according to the present invention, the pressure chamber is a fluid-tight closed space which is entirely, or among others, formed or limited by the wall of the pressure vessel and the membrane. In some exemplary embodiments according to the present invention, the term "pressure chamber" may be replaced by the definition above. In some exemplary embodiments according to the present invention, a tubing section, described below, see also FIG. 17, lies thereby on the wall or covers the wall completely or at least partially towards the interior. This tubing section may be included or ranked among the wall.

In some exemplary embodiments according to the present invention, the pressure vessel is the vessel or space in which the pressure chamber is arranged.

In some exemplary embodiments according to the present invention, the pressure vessel is a water vessel.

In so some exemplary embodiments according to the present invention, the term "pressure vessel" may be replaced by the term "fluid vessel" or "water vessel".

In specific exemplary embodiments according to the present invention, the pressure vessel has a cylindrical form.

In some exemplary embodiments according to the present invention, the pressure chamber is designed and/or arranged in such a way that the pressure existing therein depends, inter alia or exclusively, on the insertion depth of the limb stump into the interior of the pressure vessel, in any case during the intended use of the apparatus and with closed inlets and outlets, if present.

In certain exemplary embodiments according to the present invention, the membrane is arranged in the area of the insertion opening and is optionally there directly or indirectly connected to the wall in a releasable or non-releasable manner, preferably fluid-tightly. It covers the insertion opening preferably similar to a cap, insofar the pressure present in the pressure chamber does not deviate significantly from the atmospheric pressure.

In some exemplary embodiments according to the present invention, the membrane is arranged to prevent a fluid or material exchange in the interior of the pressure vessel in its axial direction.

In some exemplary embodiments according to the present invention, the membrane is always arranged in a single layer in axial and/or radial direction.

In some exemplary embodiments according to the present invention, the membrane is directly or indirectly connected to the pressure vessel on a first end side of the pressure vessel, but not also to a second end side facing the first end side.

In certain exemplary embodiments according to the present invention, the membrane is flat or balloon-like (i.e. open at one end), but not tube-like (i.e. open at both ends).

In some exemplary embodiments according to the present invention, the membrane is, at least partially, designed as a sealing element, preferably at its edge, e.g. as a sealing ring. In these embodiments, for example in the area of the insertion opening, the membrane is arranged around the limb stump. It optionally prevents the fluid, which is present in the pressure chamber, from losing pressure along the limb stump. It may advantageously prevent an outflow of fluid into the exterior of the pressure chamber and thus prevent a pressure drop inside the pressure chamber.

In some exemplary embodiments according to the present invention, the membrane is, at least during use of the apparatus (i.e. when the limb stump of the patient is inserted in the interior of the pressure vessel) and at least in sections thereof arranged inside the pressure vessel. Preferably, it is present only and/or always in the interior of the pressure vessel. Alternatively or additionally, it is connected directly or indirectly in fluid-tight connection to sections of the wall of the pressure vessel.

In some exemplary embodiments according to the present invention, the membrane is also present exclusively inside the pressure vessel during use of the apparatus (i.e. when the limb stump of the patient is inserted in the interior of the pressure vessel).

In some exemplary embodiments according to the present invention, the membrane does not protrude from the interior of the pressure vessel, in particular not in the area of a second end side or in the area of the bottom plane.

In some exemplary embodiments according to the present invention, the membrane is permanently connected to the apparatus. In certain embodiments according to the present invention, permanently means that the membrane cannot be detached from the pressure vessel without the use of tools or only destructively; for example, it can be permanently and yet releasably connected to the wall by a clamping ring or by clamping rings and one or more screws. A releasability using a tool may advantageously be provided in order to enable replacing the membrane, e.g., due to abrasion after a plurality of uses. In these embodiments, however, the membrane is not intended to be releasable from the pressure vessel by simple pulling over, pulling down or the like. At the same time, the permanent fastening may advantageously ensure that the forces which are transmitted in the pressure vessel by the fluid to the membrane during use of the apparatus cannot release the membrane from the pressure vessel or from its wall.

In some exemplary embodiments according to the present invention, at least one surface of the membrane is, at least in one section, coated with or consists of or carries friction-reducing material, for example applied by lubrication, spraying, or the like on the membrane). This allows the patient to insert the limb stump sufficiently deep through the insertion opening into the interior of the pressure vessel. In this way, it is advantageously ensured that the membrane is not or is not excessively laterally proximally displaced along the limb stump. In turn this advantageously ensures that the membrane does not protrude proximally.

In some exemplary embodiments according to the present invention, the apparatus comprises no other axial reception for the free stump end than the membrane and/or no "axial reference compliant means". The stump contacts preferably only the membrane. In other embodiments according to the present invention this may be different.

In some exemplary embodiments according to the present invention, the apparatus according to the present invention comprises no, in particular circular, disk-shaped cover of the insertion opening, which is made, e.g., of rubber and/or which is optionally a single-piece with an integral central hole.

In some exemplary embodiments according to the present invention, the apparatus according to the present invention, comprises, in particular during its use, no sand, no plaster material, no curing material, in particular not in the pressure chamber or between wall and membrane.

In certain exemplary embodiments according to the present invention, the fluid is not sand, non-solid particles nor balls, in particular not polystyrene balls, or does not comprise suchlike.

In certain exemplary embodiments according to the present invention, the membrane is not made of, or comprises no, polyethylene.

In some exemplary embodiments according to the present invention, the apparatus according to the present invention, comprises no device, such as an elastic ring or a rubber ring, and in particular no rubber ring which is provided for fixing the membrane to an outer wall of the pressure vessel. In other embodiments according to the present invention this may be different.

In some exemplary embodiments according to the present invention, the apparatus according to the present invention comprises no vacuum source (in particular no vacuum source which is operated electrically or hydraulically) or is not connected to such in fluid communication.

In certain exemplary embodiments according to the present invention, the apparatus according to the present invention comprises no pressure source and/or no, in particular inflatable, expansion devices or other "expander means" or is not connected to such.

In some exemplary embodiments according to the present invention, the apparatus according to the present invention comprises no vacuum connection.

In certain exemplary embodiments according to the present invention, the apparatus according to the present invention comprises no air chamber.

In some exemplary embodiments according to the present invention, the apparatus according to the present invention comprises no feedscrews.

In some exemplary embodiments according to the present invention, the apparatus is designed to manufacture a negative impression of the limb stump. The negative impression has a wall thickness of preferably 2 to 8 mm, particularly preferred 3 to 6 mm.

In some exemplary embodiments according to the present invention, the apparatus is not designed to manufacture a positive impression of the limb stump.

In certain exemplary embodiments according to the present invention, the apparatus comprises a swivel device by means of which the apparatus according to the present invention or its pressure vessel may be swiveled such that the angle between the longitudinal axis of the pressure vessel of the apparatus being placed on the ground changes relative to a horizontal line. The swivel angle may be adjustable; the apparatus is lockable in the reached swivel angle. This advantageously allows to manufacture a plaster impression even for patients who are unable to push straight into the insertion opening due to contractures.

In certain exemplary embodiments according to the present invention, the pressure vessel comprises the insertion opening and optionally one or more inlets and/or outlets which, however, are all, or each, provided with one closure device for closing them in a fluid-tight manner. Otherwise, the wall of the pressure vessel or of the pressure chamber is fluid-tight in these embodiments.

In some exemplary embodiments according to the present invention, the inlets and/or outlets which are provided with a closure device are part of the wall.

In certain exemplary embodiments according to the present invention, the pressure chamber is designed exclusively by the membrane and parts or sections of the wall, or exclusively by the membrane and parts or sections of the wall and fluid-tight connections between membrane and wall.

In some exemplary embodiments according to the present invention, an end side of the pressure vessel belongs to the wall, in particular the end side denoted herein as second end side.

In some exemplary embodiments according to the present invention, the pressure vessel is locked or lockable in a fluid-tight manner at its second end side.

The pressure vessel may comprise a first and a second end side. The insertion opening may be an opening on an end side. Preferably, it is situated on the first end side or in the area of the first end side.

The membrane may be connected releasably or non-releasably to the wall or to another section of the pressure vessel.

The pressure chamber may be a space of the pressure vessel which is closed by the wall and the membrane. The pressure chamber is partially or completely inside the pressure vessel. A fluid stored in the pressure chamber may be trapped alone by the combination between the wall (as long as possibly provided openings are closed by the provided closures, valves, stopcocks, etc., each according to the present invention) and the membrane.

In some exemplary embodiments according to the present invention, the multi-part wall of the medical apparatus comprises a plurality of wall part sections or consists thereof, which are arranged to be movable relative to each other.

In certain exemplary embodiments according to the present invention, wall part sections are releasably connected to each other.

In some exemplary embodiments according to the present invention, the wall part sections are designed as, or comprise, cylindrical sections which are concentric to each other.

In specific exemplary embodiments according to the present invention, the wall part sections are designed as, or comprise polyhedral sections, In contrast to round cylinder sections, polyhedral sections comprise planes which—in cross section perpendicular to the longitudinal axis—are, define or comprise a polygon. For example, the cross section may be a square or a rectangle with four corners, likewise a polygon, in particular a regular polygon with equal sides on the circumference, with for example, six, eight, twelve, sixteen or more corners. By using a polyhedral wall part sections, relative rotation, of the multi-part wall sections towards each other perpendicular to the longitudinal axis may be prevented in particular when said multi-part wall sections are telescoped completely or partially along a longitudinal direction of the medical device. Moreover, bodies with a polyhedral cross section are dimensionally more stable than, for example, bodies with a round cross section.

In some exemplary embodiments according to the present invention, the at least two wall part sections are arranged to be at least partially telescopable or movable to be pushed together and in particular accordingly coordinated. For example, concentric cylinder sections may have different diameters for this purpose so that the wall sections may slide along each other or past one another and may still be pushed into each other. For this purpose, a minor difference in diameter can already suffice.

In certain exemplary embodiments according to the present invention, the wall part sections are arranged to be at least partially telescopable by or along at least one guide pin which is arranged on or in the wall part sections.

The at least one guide pin may be arranged, for example, on or in an inner or an outer wall part section. The guide pin may be arranged in an elongated hole which is, for example, connected to a wall part section. The guide may be a releasable tongue and groove connection.

In some exemplary embodiments according to the present invention, the medical apparatus according to the present invention comprises a locking device for releasable fixing the relatively displaceable wall parts. A locking device may comprise a hook, a snap-in lock, a securing pin, or the like. A securing pin may be inserted for example into openings or bores provided for this purpose, wherein the opening are arranged vertically or otherwise in a manner not parallel to the direction of movement of the displaceable wall sections and/or are arranged in these wall sections. Furthermore, a locking device may comprise the guide pin described above. For example, the guide pin may be arranged, in particular in predetermined positions, to be turnable or tiltable, for example, such that the guide pin has the function of a securing pin. The guide pin may be inserted or plugged into elongated holes arranged at a predetermined angle to the direction of movement of the displaceable wall sections. The angle may be arranged perpendicular to the movement direction of the displaceable wall sections. A locking of the wall sections may take place in the extended state, so that an unwanted collapse of the wall sections can be prevented. A locking of the wall sections may however also take place in the collapsed state, or in the partially collapsed state.

In some exemplary embodiments according to the present invention, the locking device comprises one or more clamping screws by means of which the wall part sections can be locked, fixed or set in extended, collapsed or partially collapsed state. The clamping screw may be a knurled screw.

In specific exemplary embodiments according to the present invention, the pressure vessel comprises a first end side and a second end side.

In certain exemplary embodiments according to the present invention, the apparatus according to the present invention comprises at least one tubing section for covering the fluid chamber or pressure chamber against the multi-part wall. The tubing section may be a tubular membrane. The tubular membrane may be fluid-tight. The tubing section may limit the fluid chamber or pressure chamber against the multi-part wall.

The tubing section may allow the multi-part wall to be telescoped into each other without the fluid chamber or the pressure chamber or the fluid contacting the wall part sections moving relative to each other. Thus, damage to the fluid chamber or the pressure chamber or the membrane caused by the wall part sections may advantageously be avoided. Damage could otherwise be caused by protruding edges, by pinching/trapping the membrane between adjacent wall part sections as they move relative to each other, etc.

In certain exemplary embodiments according to the present invention, the tubing section is provided in addition to the herein described membrane which forms or takes part in forming the pressure chamber.

In some exemplary embodiments according to the present invention, the tubing section is fixed at least to the first end side (or to a top wall part section) and to the second end side (or to a bottom wall part section) of the pressure vessel. A fixation may be a clamping, an adhesive or another releasable or non-releasable connection.

In certain exemplary embodiments according to the present invention, the tubing section covers the wall part sections which move relative to each other. Furthermore, the material may additionally or exclusively comprise or be made of silicone or a silicon-like material.

In some exemplary embodiments according to the present invention, the length of the at least partially telescopable multi-part wall in the fully telescoped or collapsed state has less than 50% of the initial length of the fully extended wall. For example, the length of the completely collapsed wall which has three equally long wall part sections is approximately one third of the length in the fully extended state.

In certain exemplary embodiments according to the present invention, the tubing section and/or the membrane may be adjusted in length and may thus be used for apparatuses of different heights.

In some exemplary embodiments according to the present invention, the medical apparatus comprises at least one outlet which is, or enables, a fluid connection between the pressure chamber and the exterior of the pressure vessel. Further, it comprises a stopcock or other closure device for reversibly closing the outlet or the fluid connection.

The outlet may advantageously be used to lower the pressure present in the pressure chamber by discharging fluid from the latter. This may be necessary or helpful for inserting the limb stump or for adjusting the insertion depth of the stump.

In certain exemplary embodiments according to the present invention, the medical apparatus comprises or is connected to a reservoir having an interior and an exterior. Furthermore, it comprises a fluid connection, whereby the interior of the reservoir and the outlet are in contact and/or in fluid communication. Instead of the reservoir, a fluid source or fluid pressure source may be connected to the medical apparatus or to the fluid connection, or may be intended to be connected thereto.

The fluid present in the pressure chamber may be taken from a reservoir. The latter may, e.g., receive the fluid when fluid is discharged from the pressure chamber, as described supra. The orthopedic technician may thus advantageously change the fluid level or the fluid pressure within the pressure chamber without the need to deal with the question of fluid supply. Likewise, the discharged fluid received by the reservoir may be stored or kept therein until its next use. Using the apparatus with a reservoir advantageously makes the orthopedic technician independent of an external fluid source.

In some exemplary embodiments according to the present invention, the interior of the pressure vessel and the interior of the reservoir are thus in fluid communication via the outlet. This however may be interrupted/stopped by the valve.

In certain exemplary embodiments according to the present invention, the reservoir is a bellows. In others, it is, when empty, a flat film bag (similar to a fluidic-sealed plastic shopping bag with an inlet and/or an outlet. In the latter embodiment, it is easily rolled up or folded thinly when empty and may be transported saving space. An opening or a handle may be provided for holding, lifting or hanging.

In some exemplary embodiments according to the present invention, the pressure vessel is at least partially arranged in an interior of the reservoir. This advantageously allows a displacement of fluid between the pressure chamber and the reservoir without requiring a line hereto.

In some exemplary embodiments according to the present invention, the pressure vessel comprises a first and a second end side. In this, the outlet of the pressure vessel is arranged in the area of the second end side or in the area of an end side of the pressure vessel. It is thus sufficient to place the standing pressure vessel only with its lower area inside the reservoir.

In certain exemplary embodiments according to the present invention, the reservoir is liquid-tight against an exterior. This embodiment may result in a loss-free and spill-free use of the apparatus even when the fluid is exchanged between the pressure chamber and the reservoir.

In some exemplary embodiments according to the present invention, the pressure vessel and/or the reservoir comprise a pressure source, which is used to pressurize the pressure chamber of the pressure vessel and/or the interior of the reservoir, or are connected to the pressure source in fluid communication.

In some exemplary embodiments according to the present invention, the pressure vessel via the outlet or with an inlet, which is separated therefrom, is connected to the pressure source. There may thus be two passages in the wall, namely, outlet and inlet.

In some exemplary embodiments according to the present invention, the pressure chamber of the pressure vessel and/or the reservoir comprise water or another fluid in the interior or they are filled with them. Due to its lack of compressibility, a liquid leads to more reproducible results in the production of the plaster impression. Thereby, water is the cheapest and most-easily available variant.

In certain exemplary embodiments according to the present invention, the wall of the pressure vessel and/or the reservoir is transparent in at least sections thereof. This may allow visual monitoring of the insertion depth and other aspects during the manufacture of the plaster impression by the orthopedic technician in a simple manner.

In some exemplary embodiments according to the present invention, the pressure vessel and/or the reservoir comprise one or more markings in the area of at least one transparent section of them. The insertion depth of the limb stump may be read based on said markings.

In some exemplary embodiments according to the present invention, the pressure vessel comprises a multi-part sealing ring, in particular an upper-thigh sealing ring, wherein in other embodiments, it comprises no such ring. If said ring is provided, it can be detachably connected, for example screwed, to the pressure vessel in the area of the insertion opening or of a clamping ring or a fastening ring carrying the membrane. Said ring can prevent or limit the floating of the membrane in an exterior of the pressure vessel due to the pressure present across the membrane. This can lead to more correct pressure conditions and results of the impression. In addition, the membrane may be protected from a shearing off, for example at the edge of the insertion opening or from another injury to the membrane, for instance in the gap between the limb stump and the edge of the insertion opening.

In certain exemplary embodiments according to the present invention, the pressure vessel comprises a first and a second end side.

The reservoir or the pressure vessel comprises in some exemplary embodiments according to the present invention, a support device by means of which the device is maintained in a use or operating position. In this concrete use position, the first end side is on top and the second end side is at the bottom.

In certain exemplary embodiments according to the present invention, the apparatus according to tale present invention is suitable also for treating patients who require thigh prosthesis. The apparatus according to the present invention may comprise a support device for treating such patients. This may allow the patient to sit down or to support himself with bony pelvic structures at least in the horizontal direction.

The support device may be releasably or permanently connected to a section of the apparatus or the fluid reservoir, e.g. to its wall, e.g., by plugging on, clamping, screwing or the like.

The support device may have the form of a saddle or a section thereof.

The support device may correspond to the support device, or to a, in particular front, section thereof, as it was filed on 16 Feb. 2015 with the DPMA by the present applicant DE 10 2015 102 185.4 entitled "Aufsitzvorrichtung and Sitzmöbel zum Erstellen eines Gipsabdrucks am sitzenden Patienten zum Fertigen eines Prothesenschafts für die untere Extremität" (Support device and seating furniture for creating a plaster impression on a sitting patient for manufacturing a prosthesis for the lower extremity). The disclosure of this application is hereby incorporated in its entirety by reference.

In a certain exemplary embodiment according to the present invention, the support device extends in a longitudinal and in a cross-section direction thereof. It comprises at least one seat section which extends in the longitudinal direction. The patient may bestride said seat section, i.e. sit as if on a saddle so that the seat section extends between the thighs from front to rear. It further optionally comprises at least one stopper or a stop element extending in a cross section direction which is adapted to limit the slipping of the patient bestriding the seat section along the support device or along the seat section. This optional limitation is such that the patient may possibly freely slide along the seat section namely in one direction (posteriorly, relative to the patient sitting as intended) along the longitudinal direction or the longitudinal axis of the seat section. In the opposite direction (ventrally, relative to the patient sitting as intended), said patient may however slide only against the stopper. The stopper is optional. Thus, it does not have to be provided by the present invention. For example, the hand of the orthopedic technician may perform or replace the function of the stopper. Since the stopper may, however, substantially simplify the manufacturing of the plaster impression, a stopper is preferably comprised by or included in the support device. The longitudinal direction may be the direction which, when the patient has taken place or has been placed on the support device as intended, extends, relative to the patient, ventrally or posteriorly or from front to rear or through the thighs. The cross-section direction may be the direction which, when the patient has taken place or has been placed on the support direction, extends, relative to the patient, from caudal to cranial or from the pelvis to the head.

In some exemplary embodiments according to the present invention, the pressure chamber is formed or limited by at least a portion of the wall and by the membrane. The membrane is connected to the section of the wall, preferably in the area of the second end side of the pressure vessel, in a material connection, force-closure connection and/or form-fit connection. There may be a connector, or a connecting device, provided for this purpose. By means of the connector, an undesirable bulging, moving, floating or stretching of the membrane towards the top or in the exterior of the pressure vessel, in which the membrane—unlike in the interior of the pressure vessel—is not laterally supported by the wall, may in some embodiments according to the present invention be prevented or limited to an acceptable dimension. The connector thus holds the membrane, at least substantially, optionally inside the pressure vessel. The latter, or the connector, may counteract an undesirable floating of the limb stump. The floating may have an unfavorable influence on the pressure prevailing in the pressure chamber by the membrane, in that the membrane no longer contacts the stump with uniform pressure in all sections in which it surrounds the stump. Therefore however, there are no optimal pressures at the stump which results in that the produced plaster impression has not been produced under subsequent loads, which occur when walking with the prosthesis to be produced. Furthermore, reduced or prevented floating may contribute to protecting the membrane which is protected against damage in the interior of the pressure vessel through the wall of the latter. There is advantageously no need for any other limitation of the floating of the membrane, e.g. by ring which engages tightly on the thigh, when the connector is provided by the present invention. Since such a ring would have to be provided in a plurality of sizes in order to be able to manufacture plaster models for a plurality of differently thick limb stumps, the skilled person is offered a simplicity that is easy to understand. In addition to simplifying the use of the device, it also means saving in material for rings, costs and the like.

In some exemplary embodiments according to the present invention, the connector is connected to the membrane in a section of the membrane which does not lie in the area of the insertion opening.

In certain exemplary embodiments according to the present invention, the membrane is connected to the pressure vessel in the area of the insertion opening or of the first end side of the pressure vessel, and additionally in a second area or section of the pressure vessel which is different therefrom. The second area may preferably be in the interior of the pressure vessel and/or in the pressure chamber. The membrane may preferably be connected to the second area by the connector. The membrane may preferably be in contact only indirectly with the second area, namely optionally by the connector, i.e. preferably not having, itself, a direct contact with the second area, preferably not touching the latter.

In some exemplary embodiments according to the present invention, the second area is a central section or the middle of the bottom area or of the second end surface or end side.

In some exemplary embodiments according to the present invention, the connector is an elastic spring or comprises an elastic element.

In some exemplary embodiments according to the present invention, the connector is not elastic nor stretchable.

In some exemplary embodiments according to the present invention, the connector is length-adjustable. Said length may be adjusted by a corresponding adjusting device, which may preferably be adjusted from the outside of the pressure vessel. As a result, the distance between the distal end of the membrane and, for example, the bottom area, the lower end side or end surface of the pressure vessel is changed. This allows to adjustably arrange the membrane within the pressure vessel which in turn may allow an optimal adjustment of the apparatus according to the present invention onto the specific limb stump regardless of its length.

In some exemplary embodiments according to the present invention, the connector directly or indirectly connects the membrane to the end side of the pressure vessel which lies opposite to the end of the pressure vessel comprising the insertion opening, i.e. connecting it in particular to a lower end side, end surface or bottom area.

In some exemplary embodiments according to the present invention, the connector connects the membrane to a middle or central area of the end surface, end side or bottom area. This allows or supports a comparatively straight arrangement of the limb stump inserted into the membrane within the pressure vessel. This may prevent wrinkles from building up in the membrane and may allow a uniform pressurization. Preventing wrinkles may further be advantageous, since wrinkles may impede a—in particular digital and/or automatic—measurement of the dimension of the limb stump inserted into the pressure vessel or vessel.

In some exemplary embodiments according to the present invention, connecting is to be understood as form-fit connection and/or force-closure and/or material connection.

In some exemplary embodiments according to the present invention, the connector is arranged to connect a lowest section of the membrane, during use, or a central section of the membrane.

In some exemplary embodiments according to the present invention, the connector is arranged to keep a space or distance within the specified limits between the section of the membrane connected to the connector on one side and the section of the bottom area/lower end side/end surface, likewise connected to the connector, on the other side. The space may be, e.g., constant or straight by a non-elastic connector.

In some exemplary embodiments according to the present invention, the membrane is connected to a central area of the bottom area, bottom side or lower end side. The connector may hereby be the result of a joining process e.g. an adhesive strip, a rivet or the like In some exemplary embodiments according to the present invention, the membrane touches, in the area of its connection, the bottom area, bottom side or lower end side; in other embodiments the membrane or material thereof does not touch the aforementioned.

In some exemplary embodiments according to the present invention, the membrane comprises a support device or is connected thereto in a material connection and/or force-closure connection and/or form-fit connection. The support device is further connected to the pressure vessel, its wall or to another section of the apparatus according to the present invention in a material connection and/or force-closure connection and/or form-fit connection. It may, just as the aforementioned connector, preferably prevent the membrane from floating. The support device may therefore be understood or considered as a supplement or an alternative to the connector. It may be a bar. It may be arranged to be activated by a push or pressure, but possibly not by pulling.

In certain exemplary embodiments according to the present invention, the membrane is made of or comprises material which comprises in a first direction of the material another elasticity or extensibility than in a second direction which is different from the first direction, wherein the second direction may optionally be vertical to the first direction.

In this or in other exemplary embodiments according to the present invention, the specific elasticity or stretchability in the first and/or second direction, respectively, is achieved through fibers, which the membrane comprises, which are e.g. embedded in silicone, a silicone matrix or another material, preferably a fluid-tight material. Such fibers may extend in the first and/or second direction of the membrane, substantially extend in the first and/or second direction and/or substantially work in the first and/or second direction. In this or in other embodiments according to the present invention the different elasticities or stretchabilities may be additionally or alternatively achieved through other designs.

The first direction may, when the membrane is ready for use or is fixed as intended on the pressure vessel, be an insertion direction of the limb stump or a longitudinal direction of the pressure vessel. The second direction may be in the angle, e.g. in the right angle, relative to the first direction.

Fibers which extend or effect in the first direction are optionally not stretchable; or are stretchable only to a limited extent. Optionally, they are less stretchable than optionally provided fibers which extend or effect in the second direction. Fibers which extend or effect in the second direction may, if present, be stretchable, they may be more stretchable or more elastic than the fibers of the first direction; their extensibility may optionally correspond to that of the fibers which extend in the first direction. The fibers extending in the first direction are optional, so are the fibers extending in the second direction. The extensibility or elasticity of the fibers may correspond or correlate to that of the membrane. The fibers may be made of or comprise nylon. They may be made of tension-proof material, in particular of material which is more tension-proof than the material embedding it. Such a design, which e.g. prevents, or significantly limits, a longitudinal stretching (which may optionally be the first direction), allowing at the same time a stretching of the membrane in the circumferential or radial direction for adapting it to the limb stump, may also advantageously counteract an undesired floating of the limb stump. In addition, the relationship between the depth of the pressure chamber and the insertion depth within the membrane may advantageously remain the same. Also, the a.m. multiple piece sealing ring or thigh sealing ring may optionally be omitted. Further, it may be possible to produce, using only one membrane, plaster impressions according to the present invention at a whole row of limb stumps which are differently thick in the cross section. The membrane advantageously fits sufficiently tightly on thick as well as on thin stockings in order to prevent the creasing of the membrane described herein. The cross-section/circumferential extensibility which the membrane may comprise in some embodiments according to the present invention even when the longitudinal extensibility is prevented or limited, advantageously contributes thereto.

Optionally, the membrane is advantageously selected and arranged such that the membrane, due to its extensibility, allows an insertion opening for introducing the stump into the interior of the tube, which in some embodiments is formed by the membrane, in a range of 3 cm diameter to approximately the inner diameter of the wall or of the pressure vessel.

In some exemplary embodiments according to the present invention, the medical device comprises a heating device. It may be arranged to heat or in a regular way heat the fluid present in the pressure chamber. If for example water is used as a fluid, the introduction of the limb stump into the membrane may be more comfortable for the patient if the temperature of said limb stump, which corresponds approximately to the water temperature, is for example 30° C. or has the body temperature, than when the water is for example at room temperature or has the temperature with which it has been removed out or from a water tab. In addition, a warm fluid may contribute to a faster drying of the plaster bandage than cold fluid.

In some exemplary embodiments according to the present invention, the medical apparatus comprises a roller arrangement for rolling the apparatus on an underground, i.e. for moving in a rolling manner, with the known advantages. The roller arrangement may be releasably provided.

In some exemplary embodiments according to the present invention, the medical apparatus comprises a support on/with which the standing patient may support himself, with the limb stump inserted into the interior through the insertion opening.

In some exemplary embodiments according to the present invention, the medical apparatus comprises a suspension device. It allows to hang up the device, for example for making the plaster impression for a sub-arm prosthesis, for example on the wall. The patient can press the arm against the membrane in a specified way.

In certain exemplary embodiments according to the present invention, the support can be folded, telescoped and/or pivoted. It may be configured such that it can be moved vertically and/or from a use position to a non-use position.

The apparatus may thus be easily adapted to the specific patient, is easier to transport and can be stowed away using a comparatively small space until its next use.

In some exemplary embodiments according to the present invention, the wall of the pressure vessel limits the pressure chamber. Furthermore, it comprises an inlet which serves to introduce fluid for increasing the pressure prevailing in the pressure chamber of the pressure vessel. The inlet may be the a.m. outlet or may be a separate device.

In some exemplary embodiments according to the present invention, the membrane is partially, in at least one section thereof or completely or as a whole less than 2 mm thick, preferably less than 1 mm thick. At this thickness, it distorts the difference between the actual geometry of the limb stump and the plaster in a negligible manner, at most.

In certain exemplary embodiments according to the present invention, the pressure vessel and/or the reservoir comprise a closable air release opening with corresponding closure device. Air can escape from it, in its non-closed state, out of the pressure chamber and/or out of the interior of the reservoir. This is advantageous when filling the pressure chamber with liquid for the first time; the apparatus, if it is intended to be filled with liquid, does not have to be purchased or delivered filled with liquid. It can be air-filled and therefore remarkably lighter for transportation. The air present may be released out of the closable air release opening when filling with liquid.

In some exemplary embodiments according to the present invention, the reservoir comprises a spring device and a space of variable/adjustable size for receiving the fluid. The spring device may be arranged to reduce the space by a spring force (e.g., by subjecting a movable wall of the space to a spring pressure). The spring force may be adjusted, or adjustable using a provided mechanism, in order to maintain a fluid pressure in the space, which fluid pressure allows, limits or secures a desired insertion depth of the limb stump. Further or alternatively, the spring force may cause the pressure chamber to be automatically refilled after the treatment of a patient, for the purpose of which some fluid has been discharged from the pressure chamber and has been filled or transferred into the reservoir. Hence, the pressure chamber is automatically filled for the treatment of the next patient. Furthermore, a tube connection between the pressure chamber and the reservoir may be omitted in such configurations.

In certain exemplary embodiments according to the present invention, pressure vessels and reservoirs are designed in one-piece or integrally. This may advantageously effect a reliable seal between pressure vessel and reservoir.

In some exemplary embodiments according to the present invention, the medical apparatus comprises a device by means of which at least the pressure vessel is vertically adjustable relative to an underground on which the apparatus rests or on which the patient is standing with his healthy leg.

In certain exemplary embodiments according to the present invention, the interior and the exterior of the pressure vessel or of the reservoir may be respectively separated from each other through a wall.

In certain exemplary embodiments according to the present invention, the wall of the pressure vessel and/or the wall of the reservoir is made of plastic, for example Plexiglas or polycarbonate, or comprises one or more of these materials.

In some exemplary embodiments according to the present invention, the wall of the reservoir is made of aluminum, an alloy, stainless steel or comprises one or more of these materials.

In some exemplary embodiments according to the present invention, the wall of the reservoir is made of PVC (polyvinylchloride), while in others it is not.

In certain exemplary embodiments according to the present invention, the apparatus does not comprise an edge or ring with an opening for the patient's thigh, which edge or ring is designed to be releasably connected to the pressure vessel and/or the wall.

In certain exemplary embodiments according to the present invention, the pressure vessel and/or the wall comprise no air opening.

In some exemplary embodiments according to the present invention, the pressure vessel comprises in its interior no struts which are spaced apart from the wall, in particular none which are connected to the membrane and/or in particular none which extend in the longitudinal direction of the pressure vessel.

In certain exemplary embodiments according to the present invention, at least one, preferably central or middle, section of the membrane is attached, preferably releasably, to a section of the wall through at least one connector.

In certain exemplary embodiments according to the present invention, at least one, preferably central or middle, section of the membrane is fixed, preferably releasably, preferably directly, to a bottom area or to a second end side of the pressure vessel, preferably in a middle or central area of said second end side.

In certain exemplary embodiments according to the present invention, the connector, the membrane and/or the bottom area comprises at least one thread for directly or indirectly screwing the membrane or a component connected therewith to the pressure vessel.

In certain exemplary embodiments according to the present invention, the connector limits a floating of the membrane caused by the fluid in the pressure chamber such that a contact point surface between limb stump and membrane is at the same height level as the transition section, in which section the pressure chamber isn't anymore formed by the wall (or by a component, e.g. a clamping ring, connected thereto) rather by the membrane and/or the membrane is not supported anymore, in particular not radially or laterally, by the wall (or by a component, e.g. a clamping ring, connected thereto).

In certain exemplary embodiments according to the present invention, the membrane is made of or comprises a material which comprises, in a first direction and/or in a second direction thereof, fibers embedded in a matrix or otherwise connected thereto.

In certain exemplary embodiments according to the present invention, the membrane, which optionally comprises a matrix, or its matrix is made of, or comprises, silicone.

In certain exemplary embodiments according to the present invention, some or all of the fibers have a wavy, curvy or zig-zag pattern.

In certain exemplary embodiments according to the present invention, the membrane is non-stretchable or non-elastic in a first and/or second direction thereof.

In certain exemplary embodiments according to the present invention, the method encompasses adapting a length of the connector such that a floating of the membrane which is caused by the fluid in the pressure vessel is in such a way that a contact point area between limb stump and membrane is at the same height level as the transition section in which the pressure chamber is no longer formed by the wall but by the membrane.

In certain exemplary embodiments according to the present invention, "non-stretchable" or "non-elastic" means that the modulus of elasticity of the respective component (connector, membrane, fibers, etc.) is at least above $700 \text{ N/mm}^2$, preferably above $1000 \text{ N/mm}^2$, especially preferably above $2000 \text{ N/mm}^2$.

In certain exemplary embodiments according to the present invention, non-stretchable or non-elastic means that a extensibility of the respective component (connector, membrane, fibers, etc.) is not more than 20%, preferably not more than 10%, preferably not more than 5%, particularly preferably not more than 2% of its length before the component tears or breaks.

In certain exemplary embodiments according to the present invention, the membrane, fibers thereof and/or the connector has a modulus of elasticity such as nylon.

In some exemplary embodiments according to the present invention, the method encompasses introducing the limb stump, which is wrapped with a wet plaster bandage, into the membrane such that the limp stump is surrounded by the membrane, at least in sections thereof, around its entire circumference.

In certain exemplary embodiments according to the present invention, the method encompasses providing an adherent stocking pulled over or covering the wet plaster bandage, prior to introducing the limb stump into the interior of the pressure vessel. The adherent stocking is air-permeable and allows a release/escape of air, which may be present in the membrane prior to the introduction, along the limb stump towards the exterior of the pressure vessel. In this way, one can advantageously avoid that the distal end of the limb stump rests on an air pocket/cushion during the manufacturing of the plaster impression, which air pocket/cushion could distort the shape of the plaster impression in the area of the distal stump end as an artifact. A tube or the like may be provided instead or in addition to the adherent stocking for discharging the a.m. air. The free end of the tube may be guided back along the limb stump to the insertion opening (on any side of the membrane, i.e. through the fluid or on the plaster bandage). This end may however be also the end of a blind tube which is e.g. in the fluid.

In some exemplary embodiments according to the present invention, introducing/introduction is carried out while the patient is standing.

In certain exemplary embodiments according to the present invention, the wet plaster bandage lies on the naked skin of the limb stump. This also advantageously contributes to the fact that the difference between the actual geometry of the limb stump and the plaster is reduced to a negligible extent by the present invention.

In some exemplary embodiments according to the present invention, the method encompasses regulating how deep the limb stump is introduced into the pressure vessel. This is regulated by opening and/or closing the outlet or the valve of the stopcock. Ideally, the valve or the stopcock or another stop-device is closed, before the distal end of the limb stump comes into contact with the second end side. In these embodiments, it is therefore ensured that fluid is continuously present under the distal stump end. This allows the limb stump to remain in and on the fluid as desired. The latter presses thereby on or across the entire surface of the plaster bandage.

In some exemplary embodiments according to the present invention, the method encompasses an increase of the pressure prevailing in the pressure chamber of the pressure vessel, in particularly by 0.05 bar and 0.5 bar, more particularly by 0.2 to 0.3 bar, in particular with the patient standing with his limb stump in the pressure vessel. The increase of pressure allows to obtain a plaster impression formed under a higher pressure than usual. The shaft produced based on the aforementioned may accommodate patients which stress the shaft in an above-average manner for example because of sport, due to the fact that said shaft is also prepared to carry a corresponding higher pressure.

In some exemplary embodiments according to the present invention, the pressure vessel and/or line communicating herewith comprise a pressure gauge which determines or measures the pressure present in the pressure chamber. The orthopedic technician may, for example, orientate himself according to the measured pressure for the a.m. pressure increase.

In certain exemplary embodiments according to the present invention, the pressure increase is achieved by introducing further liquids or further gases into the pressure chamber of the pressure vessel.

In some exemplary embodiments according to the present invention, the pressure increase is achieved by decreasing the volume of the interior or of the pressure chamber of the pressure vessel.

In certain exemplary embodiments according to the present invention, the method comprises waiting, while the limb stump of the patient continues to rest in the interior of the pressure vessel, until the plaster bandage is at least partly dried, alternatively waiting for 2 to 10 minutes, particularly preferably between 3 and 6 minutes, more particularly preferably 5 minutes.

In some exemplary embodiments according to the present invention, this method is carried out on a standing patient. This leads to particularly good results in the preparation of the impression for a limb stump of the lower extremity.

In some exemplary embodiments according to the present invention, the fluid is a non-compressible fluid, in some exemplary embodiments according to the present invention, the fluid is a liquid, e.g. water.

In some exemplary embodiments according to the present invention, the membrane is deformable to the inside or to the outside, preferably elastically extensible. In others, it is elastic in one direction; but it is not elastic or comparatively or substantially less elastic in a direction which is particularly perpendicular thereto.

In some exemplary embodiments according to the present invention, the membrane is arranged such that it can be pushed by the fluid that fills the pressure chamber, through the insertion opening into an exterior of the pressure vessel.

In certain exemplary embodiments according to the present invention, the membrane is extensible, however it remains closed, except for one opening, similar to a finger of a rubber glove or an air balloon in the stretched state.

In some exemplary embodiments according to the present invention, the membrane is arranged on the pressure vessel in order to seal it on the end side.

In some exemplary embodiments according to the present invention, the apparatus has no opening of a connecting tube in an annular or cylindrical space between the, preferably elastically stretchable membrane and the wall of the pressure vessel.

In some exemplary embodiments according to the present invention, the apparatus comprises a fastening ring or stump seal which for example comprises or consists of at least two half-shells or part-shells (in short: shells). The fastening ring may be placed on the end side of the pressure vessel (and, for example, may be connected thereto by means of suitable connecting elements such as, purely exemplarily, screws, building the insertion opening for the stump. The fastening ring prevents a floating of the membrane during the use of the apparatus.

In some exemplary embodiments according to the present invention, the apparatus comprises at least one, preferably two or more cameras, image acquisition systems, surface scanners, magnetic or laser scanners, 3D scanners, infrared scanner, or other scanners, ultrasound devices, or other devices that are suitable and/or configured to capture or measure the limb stump, which is inserted into the membrane and is pressurized and/or to determine the volume and/or the geometry (e.g. length, width, surface, outer contour, radii, curvatures, dimples, edges, angles etc.) of the limb stump and/or to scan the surface of the latter. Based on these measurements, detections, sensing and the like, it may be possible to manufacture a shaft for the limb stump without having made a plaster impression using the apparatus according to the present invention. Using this procedure according to the present invention, there is advantageously no need to make a plaster impression. In certain exemplary embodiments according to the present invention, determining or measuring is a scanning of the stump and/or a scanning of the surface thereof.

In certain embodiments according to the present invention it is thereby intended to provide devices for a purely external scanning or measuring or imaging. These devices may optionally allow no 3-dimensional imaging and are therefore substantially less complex to handle and less expensive to purchase.

In other exemplary embodiments according to the present invention, the device for measuring or determining or scanning of the limb stump is selected from the set consisting of a computer tomography, a magnetic resonance tomography and an ultrasonic scanning device.

The device for measuring, determining or scanning the limb stump may be configured to obtain a three-dimensional representation of the limb stump or of a section thereof.

The aforementioned devices for measuring, determining or scanning the limp stump, such as cameras, imaging systems, scanners, ultrasound devices or other devices, may be provided distributed over the circumference of the pressure vessel or pressure chamber, distributed at identical or different distances on the pressure vessel or at its circumference. They may be integrated into the wall of the pressure vessel. They may be provided to be movable relative to the wall of the pressure vessel, for example in that they can rotate about the pressure vessel or in its interior, along a circumference and/or along a longitudinal direction of the pressure vessel.

In certain exemplary embodiments according to the present invention, the apparatus comprises a rotatable device which can carry and rotate the aforesaid devices for measuring, determining or scanning the limb stump.

The aforesaid devices for measuring, determining or scanning the limb stump may also include a light source. Thus, for example a light source, which is directed towards the limb stump and illuminates it, and a camera may be rotated together about the limb stump; said light source and said camera preferably being at a fixed distance to each other, (e.g. 10 to 20 cm, e.g. 15 cm).

In some exemplary embodiments according to the present invention, the apparatus comprises at least one device for measuring or scanning the limb stump, which device is configured to prepare or calculate a data model of the limb stump or a data model of the shaft to be produced.

The data model, also referred to herein as a model, is preferably three-dimensional. It is preferably continuous.

In some exemplary embodiments according to the present invention, the apparatus comprises a shaping device or is connected thereto in signal communication. The shaping device is arranged and/or configured to manufacture the prosthesis shaft based on the data model of the limb stump or on the data model of the shaft to be produced for the limb stump.

In some exemplary embodiments according to the present invention, the shaping device is a CNC milling device, a rapid prototyping device or a 3D printer (abbreviation for: three-dimensional printer)

The membrane has a top and a bottom. In the use of the apparatus according to the present invention, the top faces the limb stump, the bottom limits the pressure chamber. In certain exemplary embodiments according to the present invention, the membrane comprises, at least on its bottom, a marking which is recognizable or identifiable as such through the device for measuring, determining or scanning the limb stump. The marking serves as an orientation when calculating the volume or the surface of the limb stump or of the plaster impression.

This marking may be an optical and/or haptic marking. It may be an elevation, a contrast, a color marking, a coding, a color pattern, a bar code or the like. It may be symmetric or asymmetric. It is preferably applied by the manufacturer on the membrane or integrated therein. It serves to be recognized and/or evaluated by one of the devices of the apparatus. The software used for this purpose may be programmed to identify the marking and/or to evaluate its spatial position.

In some exemplary embodiments according to the present invention, the apparatus comprises no push rod protruding from the pressure vessel, which push rod comprises a coaxial anti-compression cup having an annular wall.

In some exemplary embodiments according to the present invention, the apparatus comprises no carriage on which the pressure vessel would be mounted.

In some exemplary embodiments according to the present invention, the apparatus comprises no device for generating pressure, which device is electrically and/or hydraulically operated; in particular no device which is arranged for generating pressure on the membrane or is not connected to the latter.

In some exemplary embodiments according to the present invention, the method encompasses placing the patient, optionally wearing a wet plaster bandage around his limb stump, on the apparatus such that the limb stump is or will be inserted through the insertion opening into the interior of the pressure vessel.

In some exemplary embodiments according to the present invention, the method encompasses the preparation of a model based on data acquired by the device for determining, scanning or measuring the limb stump.

The model is preferably a steady model. It is preferably a three-dimensional model.

In some exemplary embodiments according to the present invention, scanning is done using ultrasound.

In some exemplary embodiments according to the present invention, scanning encompasses a 3D-scanning.

In some exemplary embodiments according to the present invention, the method encompasses manufacturing the prosthesis shaft based on the model. It uses a shaping process for this purpose.

In some exemplary embodiments according to the present invention, the method does not encompass determining and/or using a value of the weight of the patient.

In certain exemplary embodiments according to the present invention, the method does not encompass preparing and/or calculating cross-sections through the limb stump or cross-section data.

In some exemplary embodiments according to the present invention, the method does not encompass specifying or considering a target compression.

In some exemplary embodiments according to the present invention, the method does not contemplate covering the distal stump with a cap.

In some exemplary embodiments according to the present invention, the method comprises the following steps of introducing and increasing pressure, wherein the increase follows the introduction. Inserting is the insertion of the limb stump, which is optionally wrapped with a wet plaster bandage (or of the distal part thereof), into the membrane or the fluid chamber or pressure chamber, for example such that the limb stump is, at least in sections thereof, surrounded by the membrane about its entire circumference. The subsequent increase in the pressure prevailing in the fluid chamber or pressure chamber by introducing further liquid or further gases into the fluid chamber or pressure chamber serves to acquire or generate the fluid pressure required or predetermined for manufacturing the plaster bandage, as herein described. Since the final pressure is not generated until after the patient has introduced his limb stump, at a comparatively low pressure in the fluid chamber or pressure chamber, into the membrane until reaching a sufficient or desired depth, there is advantageously not cranial or proximal massaging or displacement of soft tissue of the limb stump direction. The latter occurs, according to observation made by the inventor, when the limb stump is inserted into the membrane at final pressure and can be disadvantageous, since through friction forces, which may counteract the direction of the movement when entering the membrane, the displacement of soft tissue during the process of manufacturing the plaster impression or the measuring of the limb stump may lead to results, dimensions or findings which do not match with the conditions or circumstances of the limb stump in the shaft—manufactured after the plaster impression. The shaft may, in other words, turn out to not be optimal. Introduction at low pressure or atmospheric pressure does not lead to a displacement of soft tissue. This does not change even if the fluid pressure is later applied around the membrane and the limb stump by introducing fluid. The sequence first introducing then pressure build-up may therefore advantageously lead to more correct or accurate plaster impressions.

In certain exemplary embodiments according to the present invention, the method further encompasses loading or maximum loading of the limb stump through the patient and/or through weighting the patient with weight. To this end, this step preferably follows the steps of insertion and increase of pressure. Loading of the limb stump first after building up the required or desired pressure or target pressure may promote the stability of the soft tissue in place, achieving the a.m. advantages.

In some exemplary embodiments according to the present invention, the membrane is not tubular, i.e. not open at both ends thereof.

In certain exemplary embodiments according to the present invention, the membrane is made of fluid-tight, in particular water-tight, material. It can be made of or comprise silicone. It can be made of or comprise fiber-reinforced silicone. A co-polymer or a rubber may be provided instead of silicone.

In some exemplary embodiments according to the present invention, compressed air is not applied to the plaster bandage.

In some exemplary embodiments according to the present invention, the medical apparatus comprises at least one pressure sensor, one pressure measurement device or another device for detecting or determining pressure, or is connected thereto in signal communication. The pressure sensor or the like may thereby be arranged, configured and/or incorporated to measure a pressure prevailing at the membrane, in the pressure chamber, at a section of the surface of the limb stump which section is covered by the membrane during use of the medical apparatus and/or between membrane and limb stump.

In some exemplary embodiments according to the present invention, the sensor is a pressure sensor, an array of several pressure sensors (wherein the pressure value detected by them may for example be averaged) or the like. The sensor may be wireless, wired, etc. It can be designed as a RFID or sender.

In some exemplary embodiments according to the present invention, the medical apparatus comprises a display, is connected thereto and/or is used therewith, which display is configured to receive and display a signal from the pressure sensor or the pressure measuring device or from an evaluation device which signal corresponds to the defected pressure or a pressure signal.

In some exemplary embodiments according to the present invention, the medical apparatus comprises a detection device or is connected thereto and/or is used therewith. The detection device is configured to determine, based on, or considering a pressure value detected or determined by a pressure measuring device, e.g. the pressure sensor, the weight with which the patient, whose limb stump is inserted into the medical apparatus, should be weighted with so that the measured pressure detected by the pressure measuring device lies in a predetermined target range or moves within said range.

A predetermined target range for the fluid pressure or pressure may be between 250 mbar and 550 mbar, preferably between 350 mbar and 450 mbar and most preferably between 380 and 420 mbar. These values have resulted in particularly suitable shafts which have been produced from the plaster model produced as described herein.

In some exemplary embodiments according to the present invention, the medical apparatus comprises a display which is configured to display the weight with which the patient, whose limb stump is inserted into the medical apparatus, should be weighted with so that the pressure measured via the pressure measuring device lies in a predetermined target range.

In some exemplary embodiments according to the present invention, the weight the patient should be weighted with is determined, for example based on at least the measured pressure and/or, for example a formula (in which, for example the sine of the circumference of the limb stump, the weight of the patient, the insertion depth of how deep the limb stump is introduced through the insertion opening into the medical apparatus).

Such a formula could be:

$$P=(m*9.81*4*\Pi)/U^2$$

where P is the target pressure, m is mass of the patient, Π is a circle number and U is circumference of the limb stump in the area of the insertion opening. This formula results in a first approximation of sufficiently good results. It can however be modified. It is also possible to use other sizes which are mentioned herein.

In some exemplary embodiments according to the present invention, the method encompasses the following steps for adapting a plaster impression to a limb stump or to measure the volume of the limb stump of the patient.

providing a medical apparatus having a membrane and a pressure chamber, preferably as herein described;

optionally pulling an adherent stocking on the limb stump, wherein the adherent stocking is smooth on the side which is oriented toward the limb stump (or smoother than the side also oriented to the outside). The adherent stocking is rough on the side oriented to the outside or it comprises a surface structure (or rougher or comprises more surface structure than the side also oriented towards the limb stump) wherein the side oriented to the outside may be connected to a plaster bandage in force closure and/or form-fit manner.

inserting the limb stump which is optionally wrapped with a wet plaster bandage into the membrane;

detecting the pressure which prevails on the membrane, in the pressure chamber, on a section of the surface of the limb stump which surface is covered by the membrane and/or between membrane and limb stump;

Detecting a weight by which the patient should be weighted or relieved (for example, by being supported) so that the pressure measured or measurable by the pressure measuring device lies in a predetermined target range or moves within the latter.

In some exemplary embodiments according to the present invention, the adherent stocking may be a liner. A liner can be a textile stocking which in practice is usually pulled over the limb stump, wherein in practice this has so far been done in that the side oriented towards the limb stump is less smooth than the side oriented to the outside. The prosthesis shaft may be pulled over the liner.

In certain exemplary embodiments according to the present invention, the adherent stocking is pulled over a liner which liner is preferably directly pulled over the limb stump and abuts the same. The liner usually comprises, on the side facing the limb stump, a soft and structured surface, so as to increase the wearing comfort of further components which are pulled over the liner (in particular the prosthesis shaft). Furthermore, the liner can have a smooth surface on its outer side in order to achieve a high adhesive or friction force with respect to the prosthesis shaft. The adherent stocking may be pulled on the first liner, in particular in the form of an additional liner. The rougher or more structured surface of the outer side of the adherent stocking can advantageously allow a bond and force closure connection with a wet plaster bandage. In addition, it can advantageously "bake" with the latter during the drying of the plaster bandage and thus become part of the plaster impression. The plaster impression connected in this way to the adherent stocking obtains a comparatively smoother inner surface, which can help to reduce or avoid the effort for finishing the surface structure of the inner surface of the plaster impression.

In some exemplary embodiments according to the present invention, the method encompasses that the patient is weighted by means of the determined weight.

In some exemplary embodiments according to the present invention, the patient-related data encompasses at least one element from the following group consisting of:
  weight of the patient;
  circumference of the limb stump of the patient;
  circumference of the limb stump of the patient in the area of insertion opening;
  average of the circumference of the limb stump of the patient as far as inserted or to be inserted in the apparatus;
  volume of the limb stump inserted or to be inserted into the limb stump;
  surface of the inserted or to be inserted limb stump;
  cross-sectional area of the limb stump, in particular in the area of the insertion opening;
  compressibility of the limb stump;
  length of how much of the limb stump is inserted or is to be inserted into the apparatus.

The compressibility can be determined by measuring a force or a pressure which is or should be applied to effect a predetermined impression in the limb stump.

In some exemplary embodiments according to the present invention, the bottom area of the medical device according to the present invention comprises at least in sections a curved shape of tilting, twisting and/or displaceably moving the apparatus on a contact surface.

A curved form may for example comprise a concave form curved inwards in the direction of the pressure chamber. An apparatus with a concavely curved bottom surface can be rotated or tilted on a spherical base or on a spherical or cylindrical rolling element. The form of the support may also be parabolic or may have a different form. The movement of the apparatus on the support may be a rolling or sliding movement.

The curved form may alternatively comprise a convex curved shape directed outwards, away from the pressure chamber. An apparatus having a convex bottom area may preferably be moved or rolled on a flat surface. The convex form may e.g. have a hemispherical form, a spherical segment form, a paraboloid form, a partial cylindrical form or another curved convex form.

The system according to the present invention having a medical apparatus and at least a contact surface may in some embodiments according to the present invention be tilted, twisted and/or displaced relative to the contact surface during the production of a plaster impression of a limb stump. The movement of the apparatus relative to the contact surface may be a rolling movement, a sliding movement or a combined movement of rolling and sliding. The movement may be initiated and carried out by or supported by the prosthesis wearer himself. With the aid of this movement, not only a static load but also a muscular and/or bone movement and load may be moulded as it occurs later when moving while wearing the prosthesis. This additional dynamic load may improve or increase the accuracy, the wearing comfort, the avoidance of possible pressure points between the limb stump and the prosthesis. The impression method, as described supra, can basically be the same when applying the system according to the present invention.

In some exemplary embodiments according to the present invention, the contact surface comprises a planar or curved surface. A curved surface may be or may comprise a curved form, a hemispherical form, a spherical segment or section, a paraboloid form or another form.

In certain exemplary embodiments according to the present invention, the contact surface forms a rolling element. In other words, the contact surface may be imaged on the surface of a rolling element. A rolling element may for example be a ball, a roller, an ellipsoid.

In certain exemplary embodiments according to the present invention, the contact surface is movable, with the aid of a guiding device and/or of rolling elements, relative to the apparatus and/or to a fixed bottom. A guiding device may be a carriage.

The carriage may have on its bottom side rollers or wheels for moving on an underground. It may have rollers which permit movement in only one direction (similar to a ratchet).

The carriage may optionally be guided using rails along a specified path. A specified path may thereupon be optimized or advantageous in that a dynamic loading of the limb stump during a plaster impression is simulated, using the specified path of the guiding device, with regard to a muscular and/or bone movement during walking.

In some exemplary embodiments according to the present invention, the contact surface can be connected and/or connectable to the second end side and/or to the bottom area of the apparatus, preferably releasably. The contact surface connected to the apparatus may be referred to as a support device.

In certain exemplary embodiments according to the present invention, the system according to the present invention comprises a securing sleeve which is connected and/or connectable to the pressure vessel in order to fix the limb stump to the apparatus during the manufacturing of a plaster impression or of a data model. This fixing may, at least in one spatial direction, secure the limb stump against slipping or displacement in the pressure chamber during movement and during the plaster impression.

In some exemplary embodiments according to the present invention, the securing sleeve is pressure-tight. The term pressure-tight is to be understood with respect to the accuracy of measurement of a pressure drop during plaster impression. Preferably, a vacuum is applied or built up in the space between the securing sleeve and the limb stump so that the latter is stabilized during movement on a contact surface and cannot slip out of the pressure chamber. An apparatus for generating the vacuum may be provided for example as an air pump.

In some exemplary embodiments according to the present invention, the medical apparatus according to the present invention comprises a release unit for releasing pressure of the distal area of the limb stump. The release unit is preferably arranged within the pressure vessel and/or within a space formed by the membrane. The release unit may advantageously protect delicate soft parts in the region of the distal end of the limb stump against a pressure built up by the fluid.

In some exemplary embodiments according to the present invention, the release unit is a hollow vessel with at least one opening or recess.

The hollow vessel may have a cup-like form. It may optionally comprise cylindrical walls and/or a conical cross-section.

The conical form with a tapering cross-section may have a larger diameter at the opening or at the opening cross-section (with an exemplary round and circular cross-sectional form) for introducing the limb stump. The diameter may taper towards the bottom of the hollow vessel.

The opening or recess is preferably open towards the distal region of the limb stump or towards the upper end side of the apparatus and can thus protect this delicate area of the limb stump from a possible pressure load. The limb stump, which may be wrapped with a wet plaster bandage when inserted, does not come, in distal sections thereof, into contact with the membrane, depending on the form of the opening. For this purpose, the distal region of the limb stump may rest on the side walls, on the upper edge or on the upper circumference of the release unit which unit is designed as hollow vessel by way of example.

The release unit is preferably arranged within the pressure vessel, on the membrane, outside of the pressure chamber and is associated therewith. The release unit is preferably kept dry, i.e. without having contact to fluid.

In certain exemplary embodiments according to the present invention, the opening of the release unit comprises, or is covered by, a membrane. The membrane may cover or protect to the outside an inner material of the release device which device may be designed as a hollow vessel. An inner material with which the hollow vessel may be substantially or partially filled is for example a soft compressible material.

A release unit which is filled as a hollow vessel with soft material and is covered by a membrane, may advantageously be used as pressure release unit for the distal end of the limb stump. As a result, direct contact of the distal end of the limb stump with the membrane of the pressure chamber may be avoided.

In certain exemplary embodiments according to the present invention, the release unit integrated into the membrane and/or is an integral component of the membrane. For example, the membrane in the distal area of the limb stump may be designed as two-ply or double-walled. The release unit may be introduced or integrated between an inner and an outer layer of the doubled-wall membrane.

The release unit may be introduced or placed in the double-walled membrane, wherein the release unit may move or align within the double-walled membrane.

The release unit may also be connected to one or both layers of the double-walled membrane in material connection. A material connection can be an adhesive bond, a weld or a different type of material connection.

A release unit integrated into the membrane may, with the aid of a medical apparatus according to the present invention, simplify the manufacturing of a plaster impression or of a data model of a limb stump, in particular a lower leg stump. A separate alignment of the release unit in the membrane may advantageously be omitted. With the release unit being integrated into the membrane, said release unit cannot be positioned independent of the membrane and thus cannot be arbitrarily displaced as desired, rather only in predetermined regions or limits.

In some exemplary embodiments according to the present invention, the release unit is a section of the membrane. The membrane forms the release unit in the distal region of the limb stump. The connection of the membrane area having the release unit with the remaining, elastic membrane area may be a material connection, e.g. an adhesive bond or a weld.

In certain exemplary embodiments according to the present invention, the apparatus comprises an adapter for the connection with the pressure vessel, wherein the adapter is provided for the releasable connection with the limb stump. The adapter comprises or is at least an adherent stocking and a release unit and/or a device for transmitting tensile forces, which is connected, for the transmission of tensile forces, to the adherent stocking in force-closure and/or form-fit connection.

In some exemplary embodiments according to the present invention, the device for transmitting tensile forces being connected to the adherent stocking in force-closure and/or form-fit connection is a Velcro fastener, a material integrally connected to the adherent stocking, for example a plastic or a composite material welded or glued to the adherent stocking, an area or section, which is incorporated into the adherent stocking or which is material-reinforced, for transmitting tensile forces, e.g. multilayer woven layers of the adherent stocking, or any other suitable embodiment for transmitting tensile forces.

In some exemplary embodiments according to the present invention, the set comprises at least one medical apparatus according to the present invention and at least one stocking to be pulled over (pulling over also means imposing) the limb stump, wherein the stocking connected to the limb stump is connected to the surface of the membrane at or in the pressure vessel in a force-closure connection, in particular a frictional connection.

In some exemplary embodiments according to the present invention, the stocking comprises at its outer side, i.e. not the inner side oriented towards the limb stump, a frictional surface. A frictional surface is for example a rough surface. The surface can be structured. The surface may be coated and/or chemically or physically treated to provide a frictional surface. In particular, a frictional surface prevents the limb stump from slipping out of the stocking, without additional force. As a result, a plaster impression or a data model of a limb stump, in particular a lower leg, can advantageously be produced without the patient causing unforeseen or unintended movements during the plaster impression or during the production of a data model. Such movements can adversely affect the production of the plaster impression or data model. Alternative methods to avoid such unforeseen or unwanted movements of the patient can advantageously be avoided by means of the stocking according to the present invention.

In some exemplary embodiments according to the present invention, the medical apparatus comprises a form body arranged inside the pressure vessel. The form body is designed and prepared for receiving and/or supporting and/or releasing pressure from the distal region of the limb stump. The form body is arranged within the pressure vessel and/or within an area formed by the membrane, in particular an inner area, in which area also the limb stump is inserted. The outer surface of the form body lies, preferably at least partially, at the surface of the membrane—directly or indirectly—frictionally.

In some exemplary embodiments according to the present invention, the form body is shell-shaped. The form body may be made of, or comprise, a thermoplastic. Likewise, the form body may be made of another material, for example of fiber-reinforced, composite material or of metal or may comprise same.

In certain exemplary embodiments according to the present invention, the form body is constructed as multiple-part and/or as module-form. The multiple-part and/or module-form form body parts may be assembled, or joined or connected in form-fit connection and/or force-closure connection. At least one shell-formed basic module or base module may be used as form body. The basic module may be connected or connectable to one, two or more segments of the multiple-part and/or module-formed form body.

In certain exemplary embodiments according to the present invention, the form body encloses a compressible material or comprises the latter. The compressible material may be foam. The compressible material may for example be placed in or bonded to the form body.

The unit according to the present invention comprises a pressurization/control unit for the pressure chamber of the medical apparatus according to the present invention and a medical apparatus according to the present invention.

The pressurization/control unit comprises at least one pressure reservoir connection, one pressure-limiting valve and at least one connection at the pressure chamber with a regulating valve for pressure increase and/or a regulating valve for pressure decrease in the pressure chamber.

The regulating valve may be a control valve.

In some exemplary embodiments according to the present invention, the pressure reservoir connection is a connection to a pressure source, in particular to a water line. By means of the pressure reservoir, fluid, in particular water, may be supplied form a water line or from another reservoir to the pressure chamber.

In certain exemplary embodiments according to the present invention, the pressure-limiting valve limits the pressure of the fluid line at the pressure reservoir connection to a value between 0.7 bar and 0.9 bar, in particular to maximum 0.8 bar.

In certain exemplary embodiments according to the present invention, the unit, in particular the pressure pressurization/control device, comprises a pressure display. The pressure display may be a pressure gauge. By means of the pressure display, the pressure in the pressure chamber may be checked and/or monitored. The pressure display may have a redundancy function or a safety function against a further pressure display which may be directly arranged on the pressure chamber.

In some exemplary embodiments according to the present invention, the unit, in particular the pressure pressurization/control unit comprises an emergency shutdown device. By means of this emergency shutdown device the pressure reservoir connection may be closed or blocked. For example, unforeseen pressure peaks or a sudden pressure rise or pressure drop may occur in the supply line to the pressure reservoir connection, which is to be quickly interrupted for safety reasons, in particular for protecting the limb stump. This may advantageously be done simply and quickly by actuating the emergency shutdown device.

In some exemplary embodiments according to the present invention, the unit, in particular the pressure pressurization/control unit, comprises a suction nozzle. The suction nozzle may be arranged downstream of the regulating valve for pressure decrease of the pressure in the pressure chamber. There may be vacuum present at the suction nozzle or vacuum may be generated by the latter. For example, a suction pump or a vacuum pump may be connected to the suction nozzle. Likewise, a so-called venturi nozzle or a venturi tube may be connected to the suction nozzle. The suction nozzle may be a venturi nozzle or a venturi tube by means of which a fluid, in particular water, may be sucked off or vacuumed out of the pressure chamber of the apparatus according to the present invention.

In certain exemplary embodiments according to the present invention, the unit, in particular the pressurization/control device, comprises no electrical components. The pressurization/control unit may preferably not comprise any current connection, in particular no electrical components and/or any current connection which would be used for pressure variation within the pressure chamber connected to the pressurization/control device.

Some or all of the embodiments may comprise one or several of the advantages mentioned supra or in the following.

It is obvious that the prosthesis shaft is useful to the patient due to the recovered mobility, especially when standing and walking. When standing and walking, when the shaft is loaded according to its intended purpose, the shaft must therefore sit especially comfortably. The methods known so far for producing the plaster impression or for measuring the dimensions of the stump do not adequately comply with or meet or fulfill this, since they do not take into account the soft tissue displacement in the stump, as they occur later when the shaft is subjected to stress, e.g. relative to the bony portion of the stump, due to lack of stressing the stump during measuring or plastering. The result may lead to inaccuracy in the manufacturing of the shaft, which even by determining the body dimensions at precisely defined heights and ranges lies in the cm-range. This is advantageously not the case when the apparatus according to the present invention is used while the patient is standing; the stump undergoes almost identical loads and soft tissue displacement as in the later load in the shaft.

By means of the present invention, it is advantageously possible for the first time to reliably and above all reproducibly produce a plaster impression of the patient's stump or to measure the dimensions of the stump, during the manufacturing of the plaster impression or the measuring of the patient who is standing with the stump, in order to obtain a data model which reflects or mirrors the stump.

Thus, the present invention allows to make a plaster impression or to obtain a stump model as a base for a shaft that is conveniently fitting the person wearing it, especially when walking and standing. Less skill is needed than hitherto required.

Thus, the present invention enables the manufacturing of shafts for prosthesis of human upper and lower extremities in an objective manner based on directly obtained measurements data. The present invention thus enables the production of a well-adapted prosthesis, wherein however the expensive activities, which are executed purely subjectively and manually which activities are required in the methods of the state of the art, may be avoided.

Thereby, it is advantageously possible in the present invention and in certain embodiments intended to utilize a purely external scanning or measuring or imaging. This is considerably less complex, both in terms of the evaluation of their measuring and costs of acquiring the required devices.

By means of the present invention, during the manufacturing of the plaster impression of a standing patient and thereby having an almost realistically loaded stump, it is possible for the first time to obtain already during the manufacturing of the plaster impression or during the measurements a feedback from the patient concerning tight or painful areas or points. Using the apparatus according to the present invention, the condition or situation of the shaft when worn later is so to say already felt "in advance" by the patient during the production of the plaster impression or during the measurements; unsatisfactorily fitting sections of the shaft worn later are recognized or anticipated. In this way, desired changes or upholstering may be recorded and prepared by the orthopedic technician already during the manufacturing of the plaster impression and the measuring of the patients. This may, over the time which passes until the final, fitting shaft is present, (help) saving significant amount of work and time.

In many exemplary embodiments according to the present invention, there is advantageously no need for an access to a source of electrical voltage, compressed air or water line. The apparatus may therefore be used self-sufficiently and transportably or in a mobile manner. This applies in some exemplary embodiments according to the present invention to the entire apparatus. In other exemplary embodiments according to the present invention, the pressure vessel comprises no access to a source of electrical voltage, certain devices of the apparatus, e.g. the devices for measuring, scanning etc., are however embodied with an access to a voltage network.

The patient may possibly independently execute the method according to the present invention without having expertise or support. No medically trained staff is required to carry out said method.

Since the patient is able to use the apparatus while standing and thereby stressing the membrane with parts of his body weight, there is no need for precautionary measure to protect the limb stump from being displaced by axial reaction forces which may act on the limb stump through the pressure chamber and may push the limb stump out of the interior of the pressure vessel. In other words, there is no need for the patient to be held in position—relative to the pressure vessel. His body weight may fulfill this.

The present invention allows, in contrast to the conventional methods of the state of the art, to produce shafts for prostheses in an objective manner. This ensures a better supply thanks to an improved fitting form and may reduce the production costs by requiring no or only a small expensive manual processing and adaptation. In addition, the patient care can be accelerated since the time-consuming adaptation steps may, at least in number, be greatly reduced, or even be completely eliminated.

By means of the method according to the present invention, transparency may be achieved since the plaster impression, the data model, prosthesis shaft takes place on verifiable bases.

The present invention is exemplarily explained with regard to the accompanying drawings in which identical reference numerals refer to the same or similar elements. The following applies in the, partly, highly simplified figures.

Figure 6:
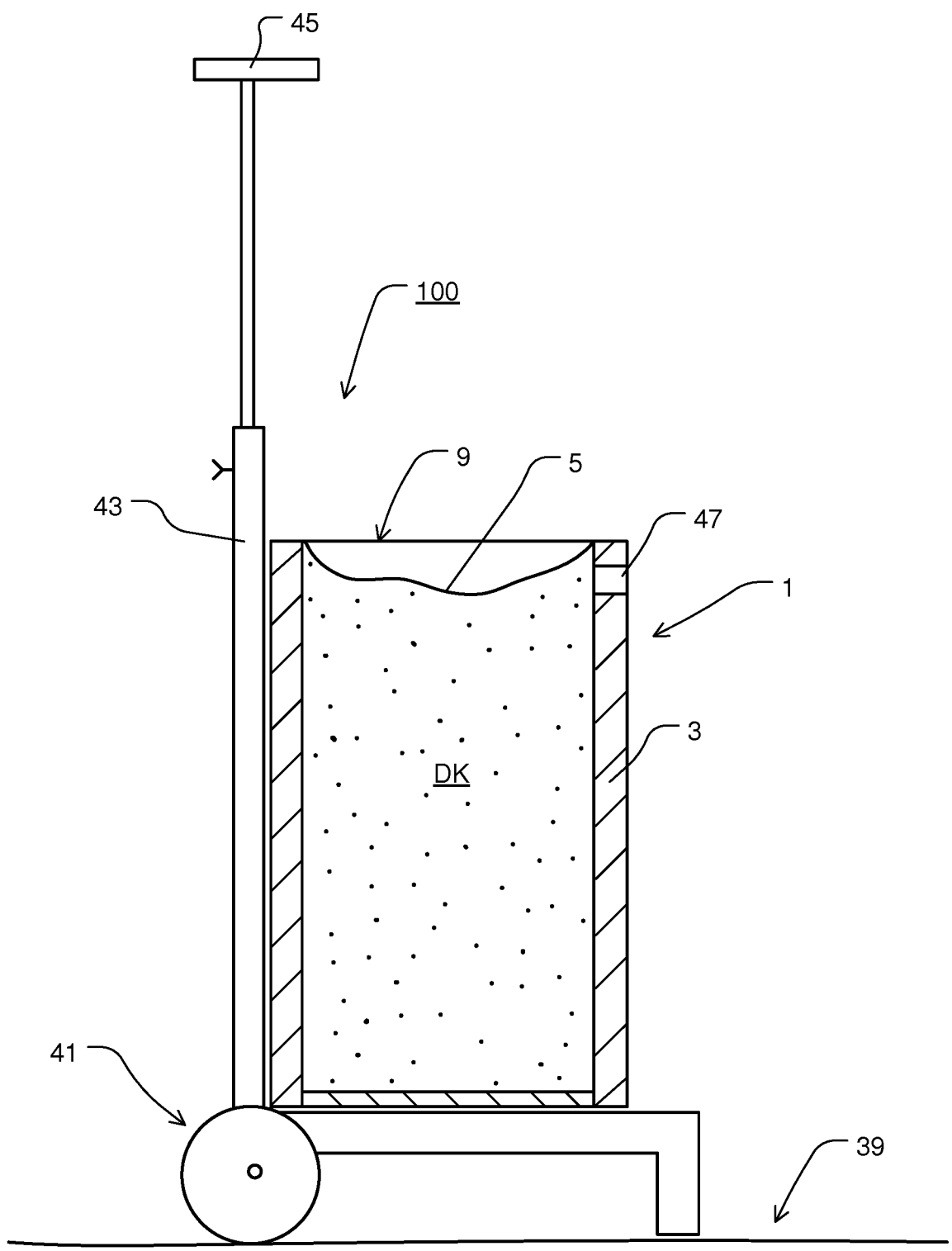
Figure 7:
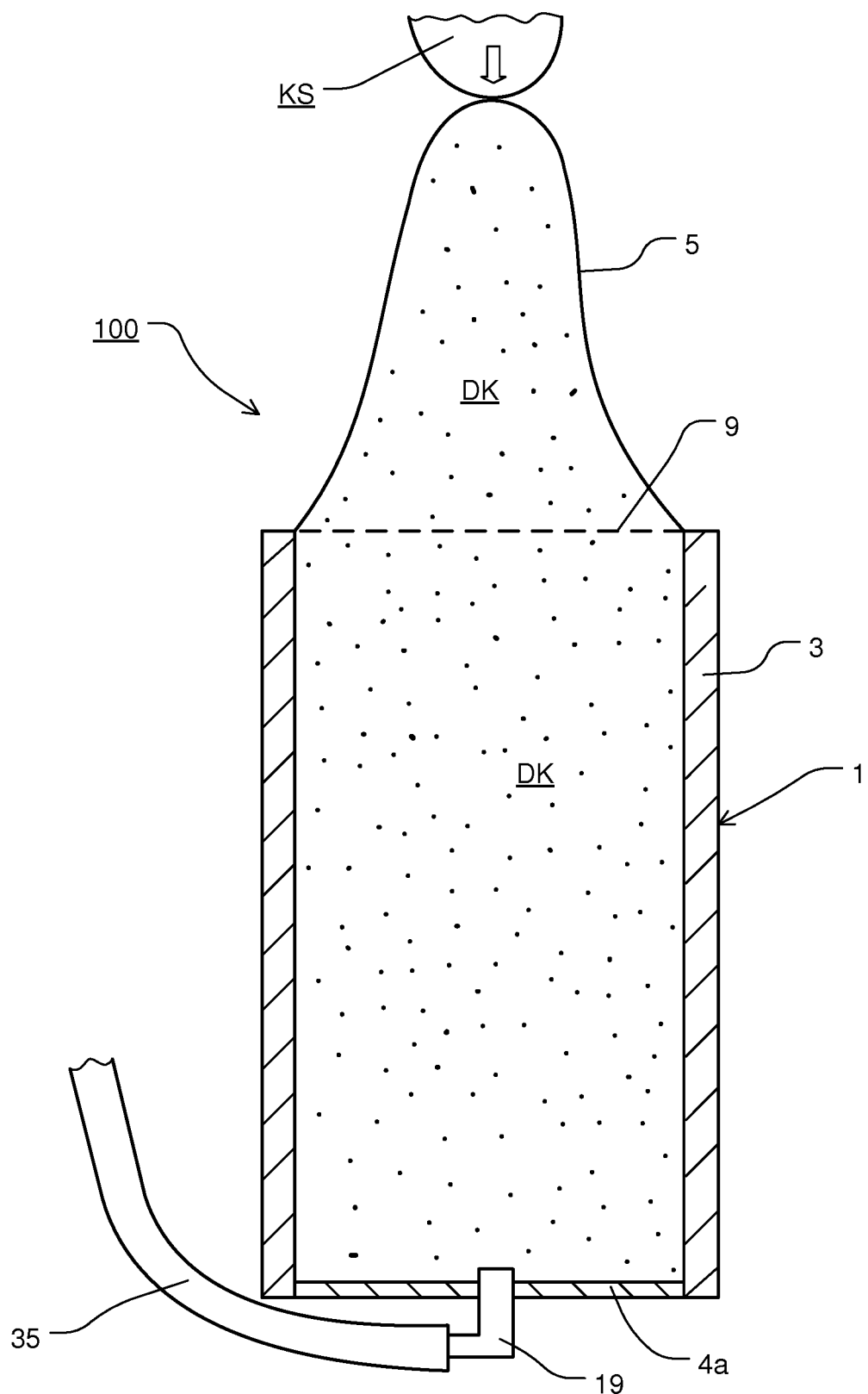
Figure 8:
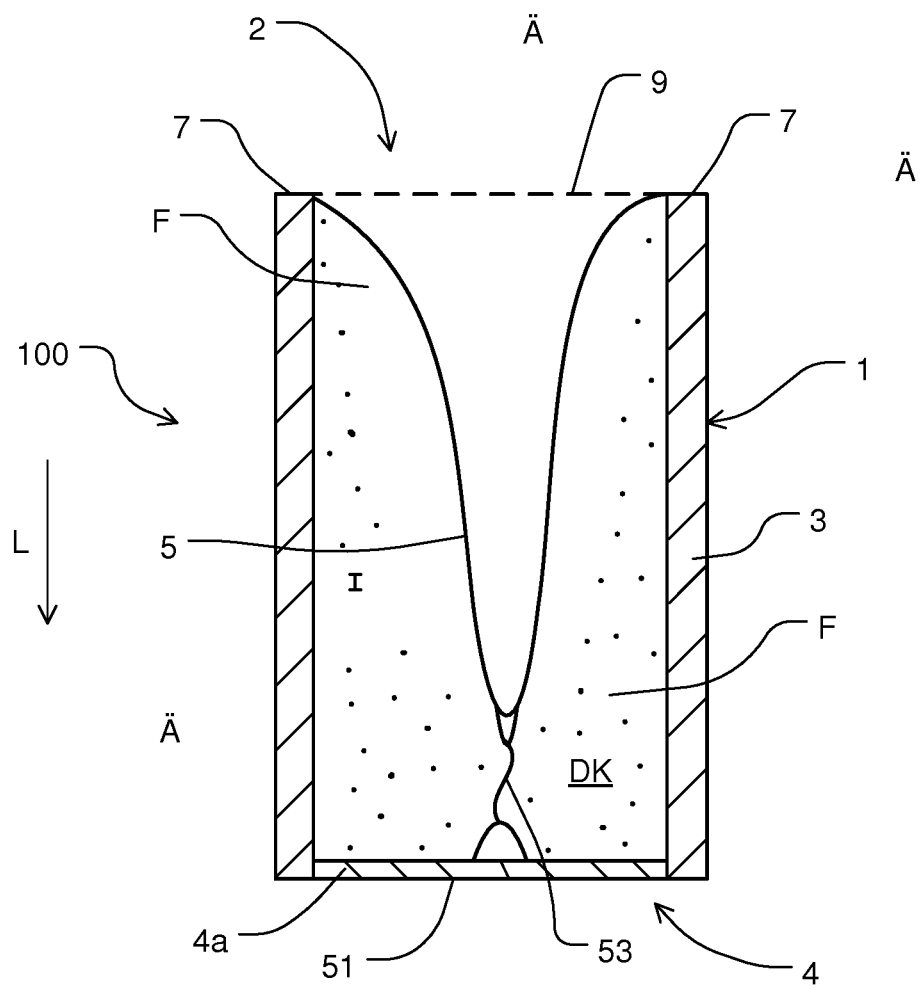
Figure 9:
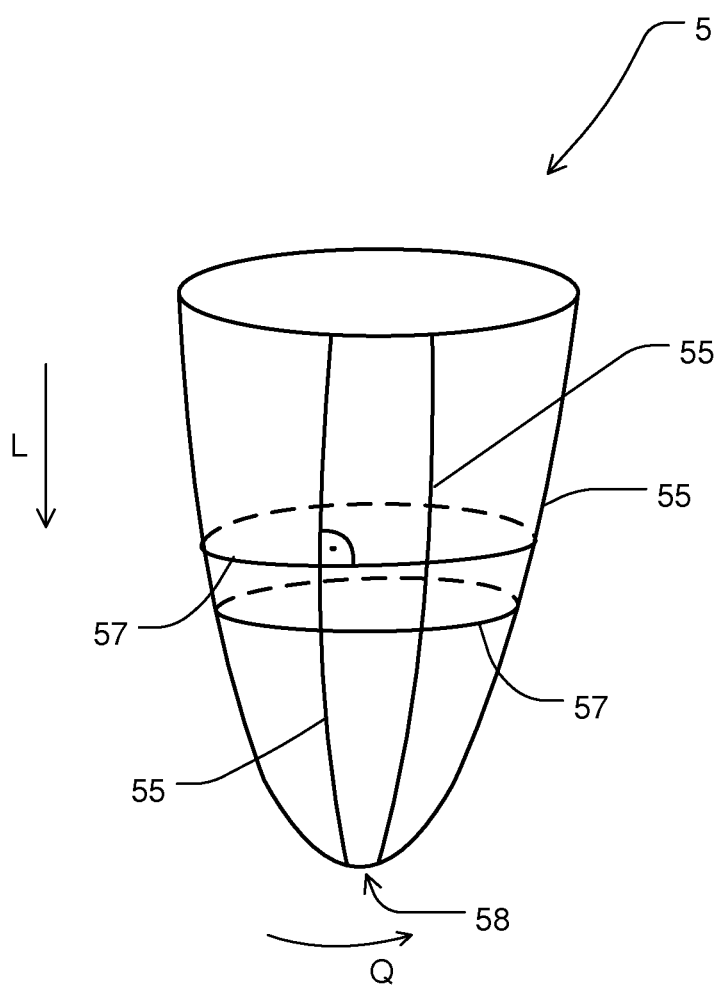
Figure 10:
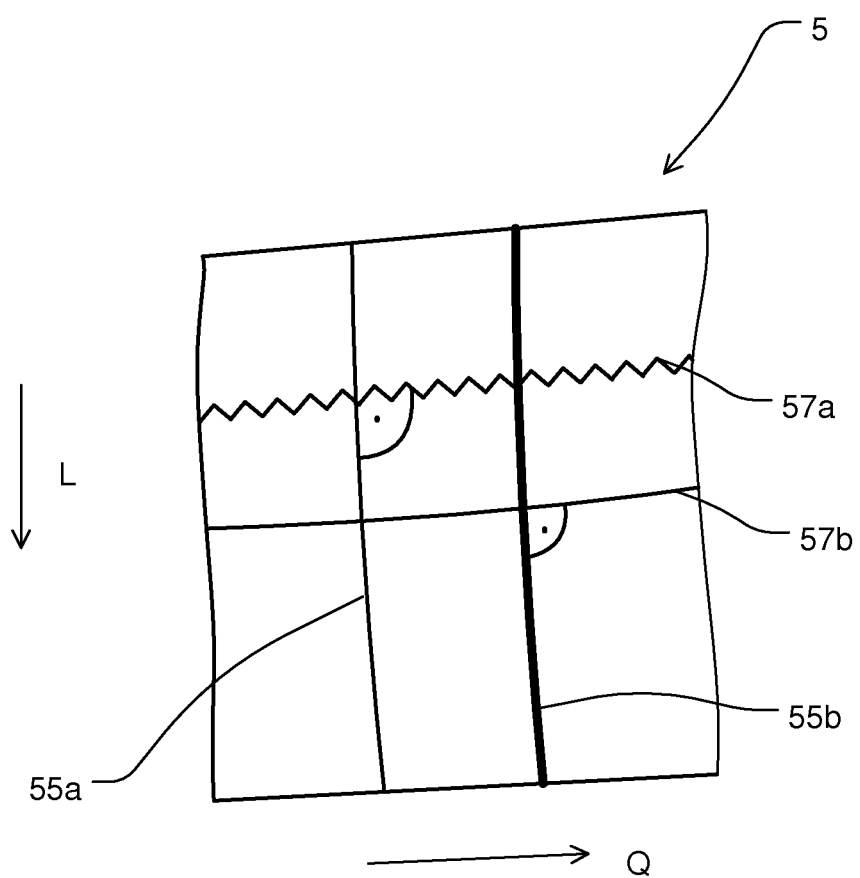
Figure 10A:
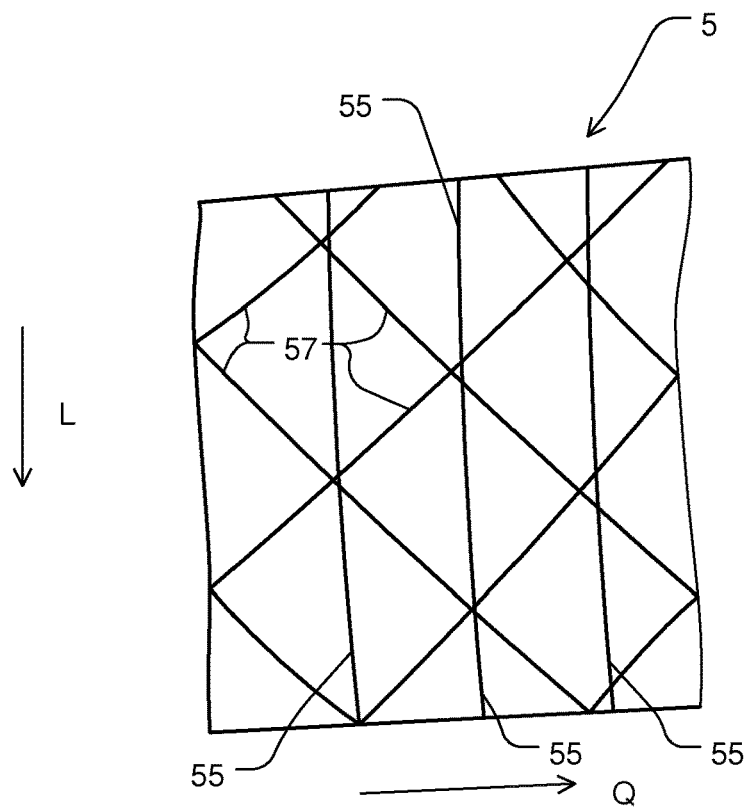
Figure 10B:
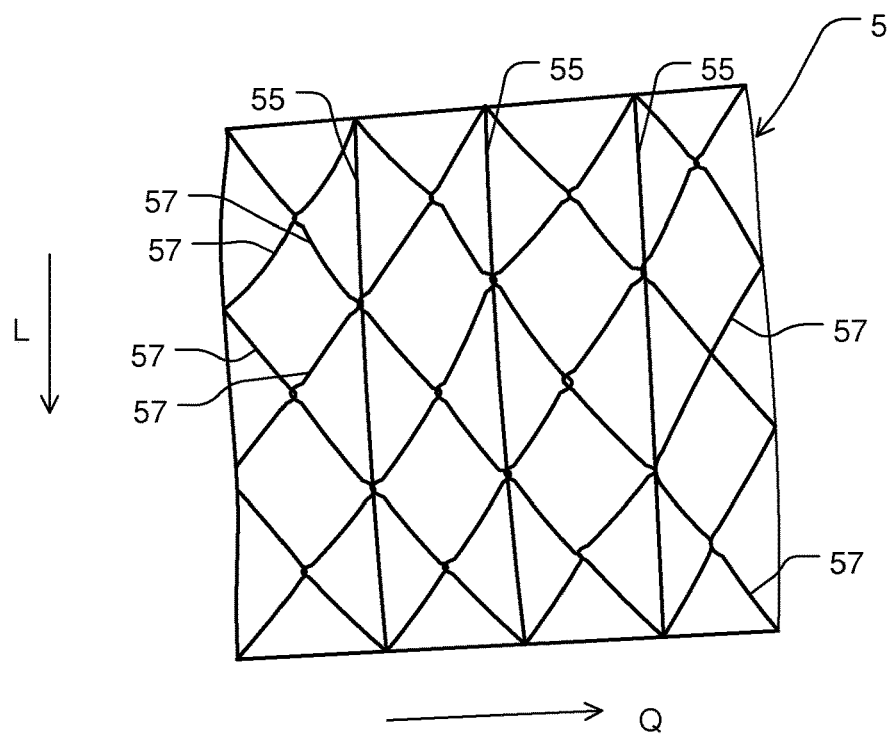
Figure 11:
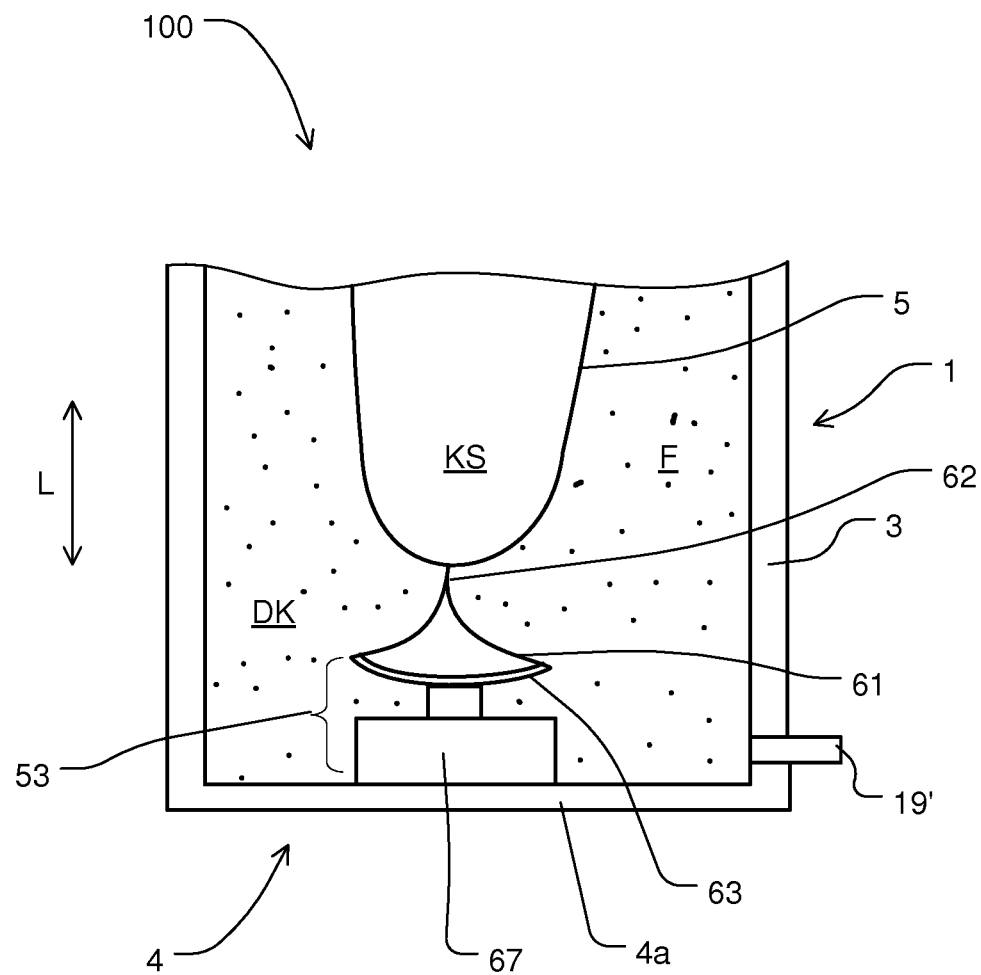
Figure 12:
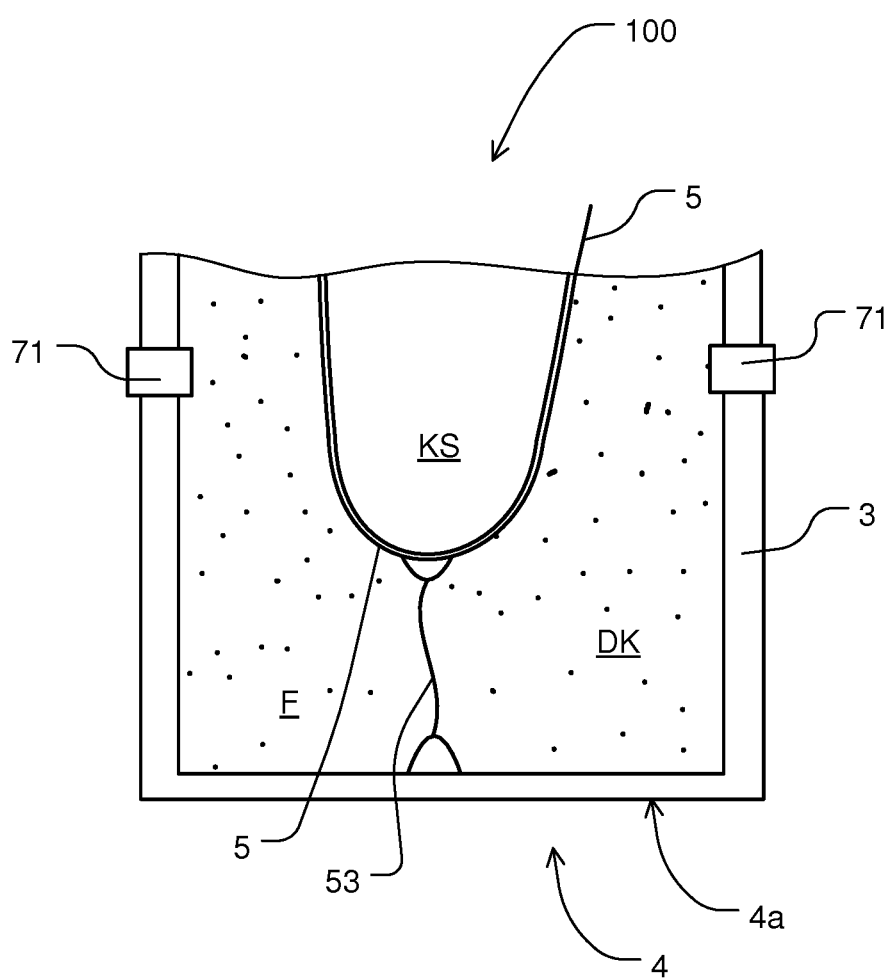
Figure 13:
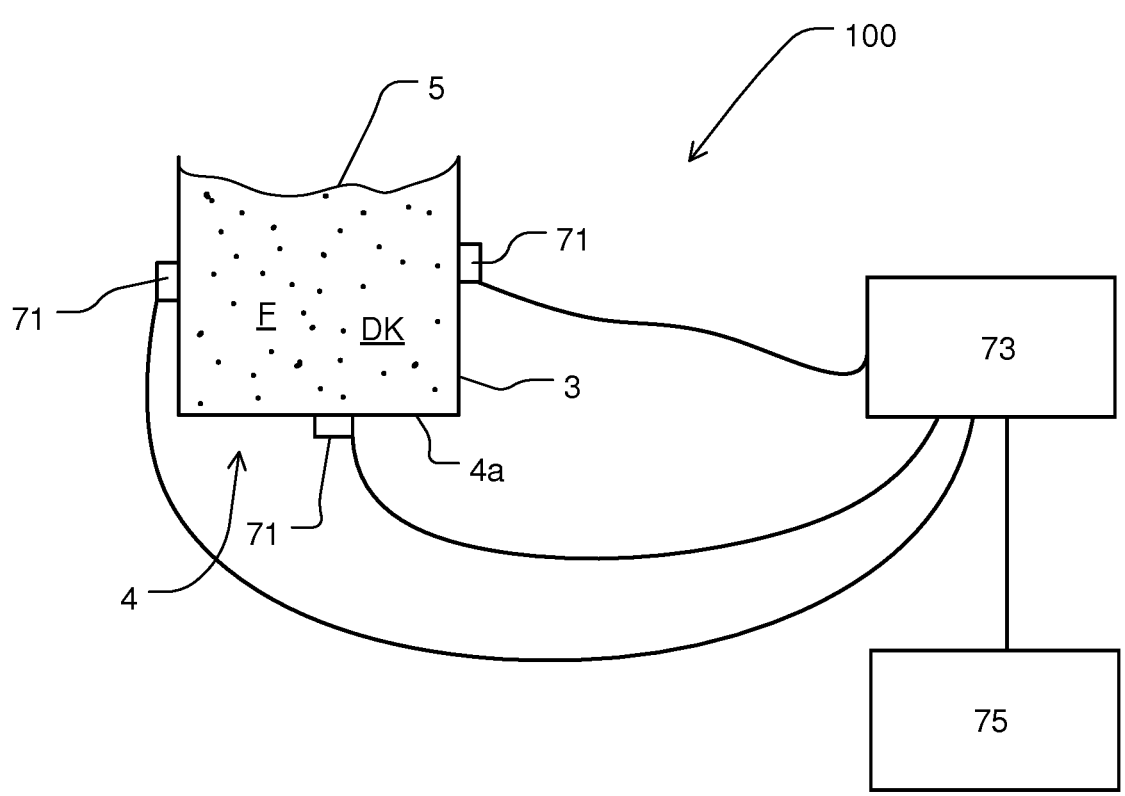
Figure 14:
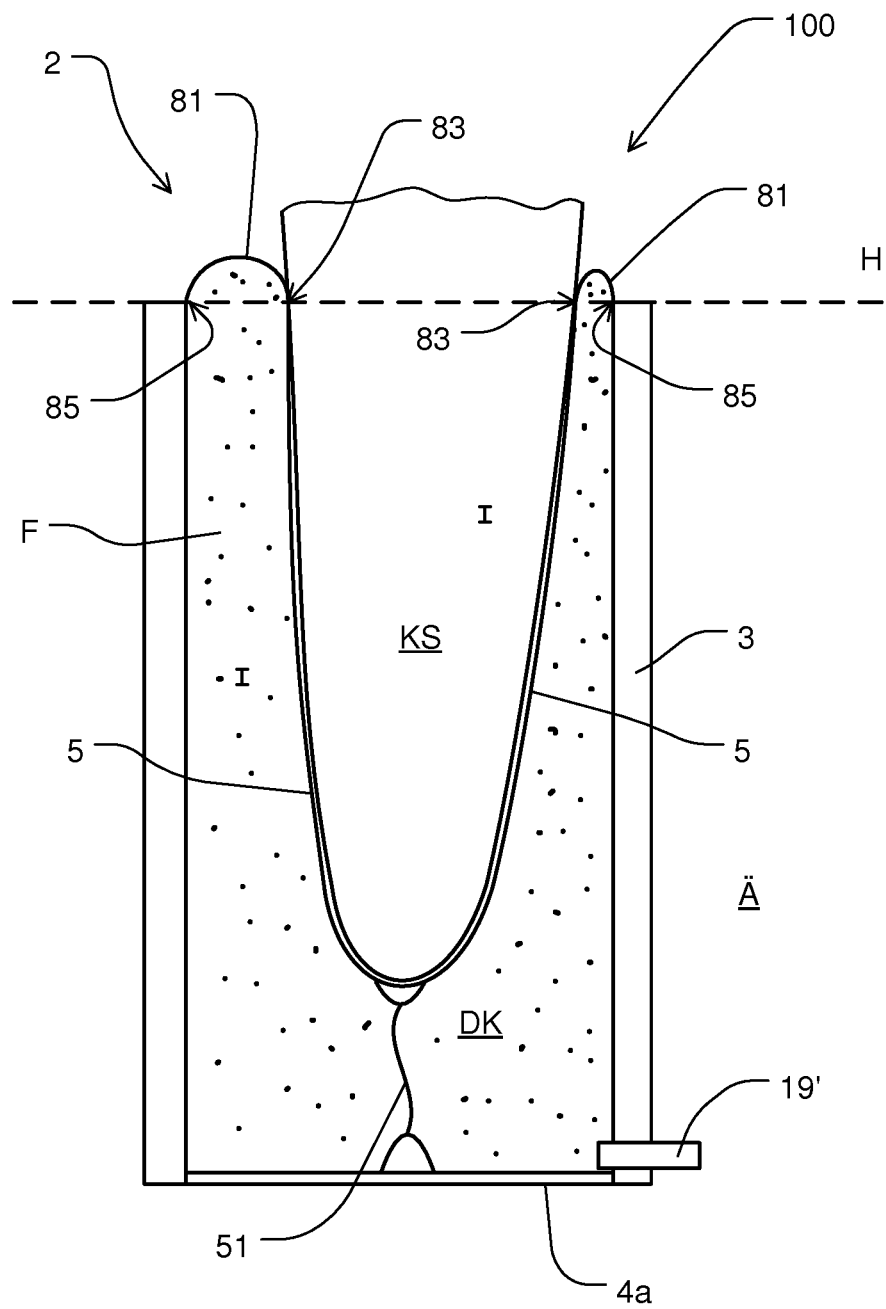
Figure 15:
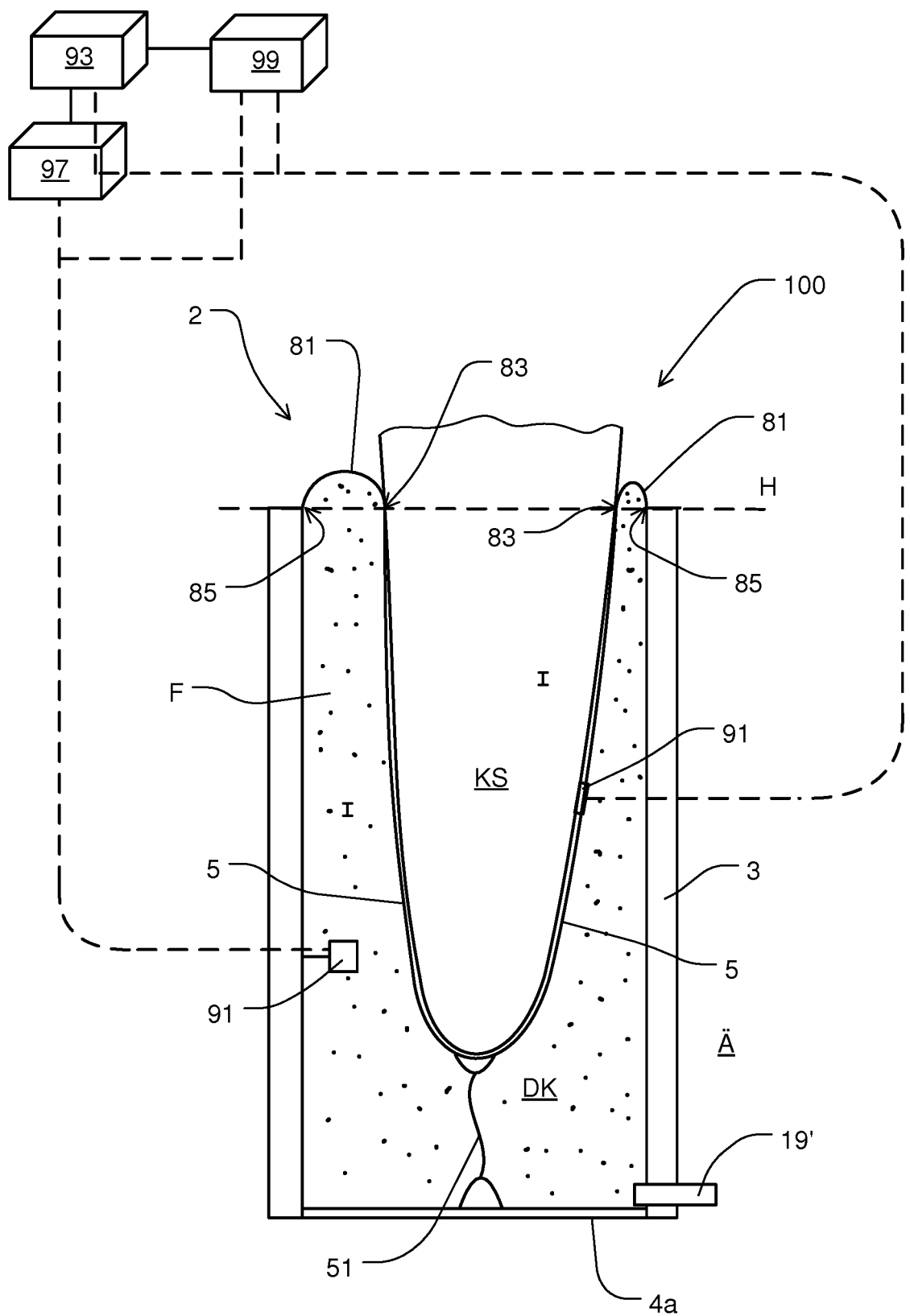
Figure 16:
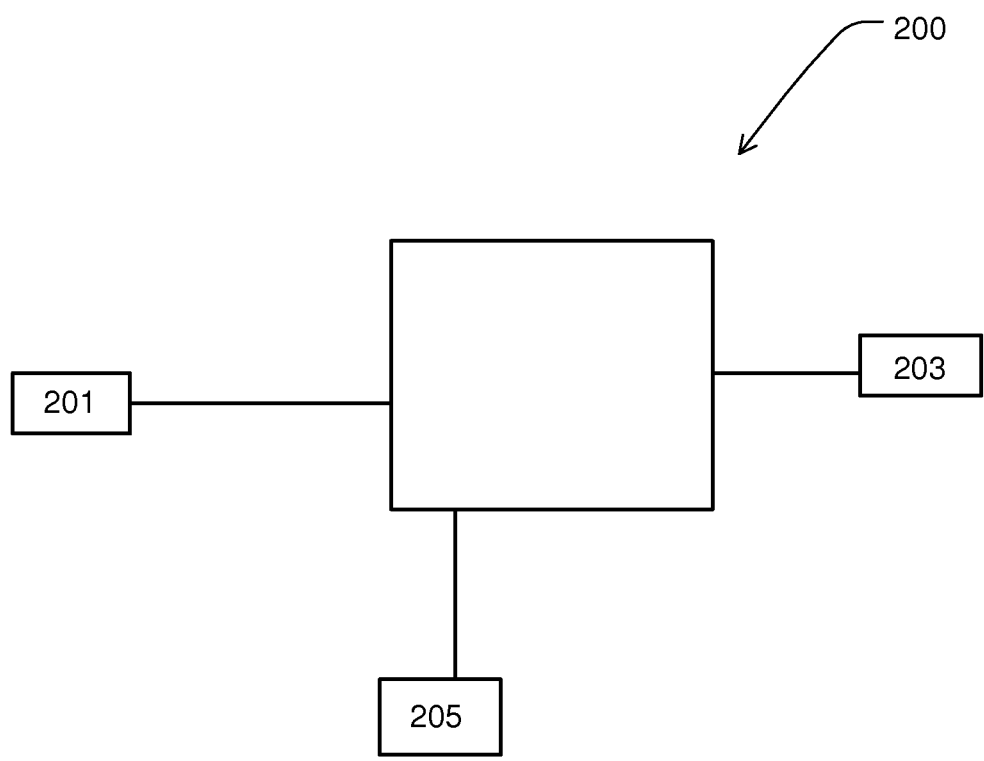
Figure 17:
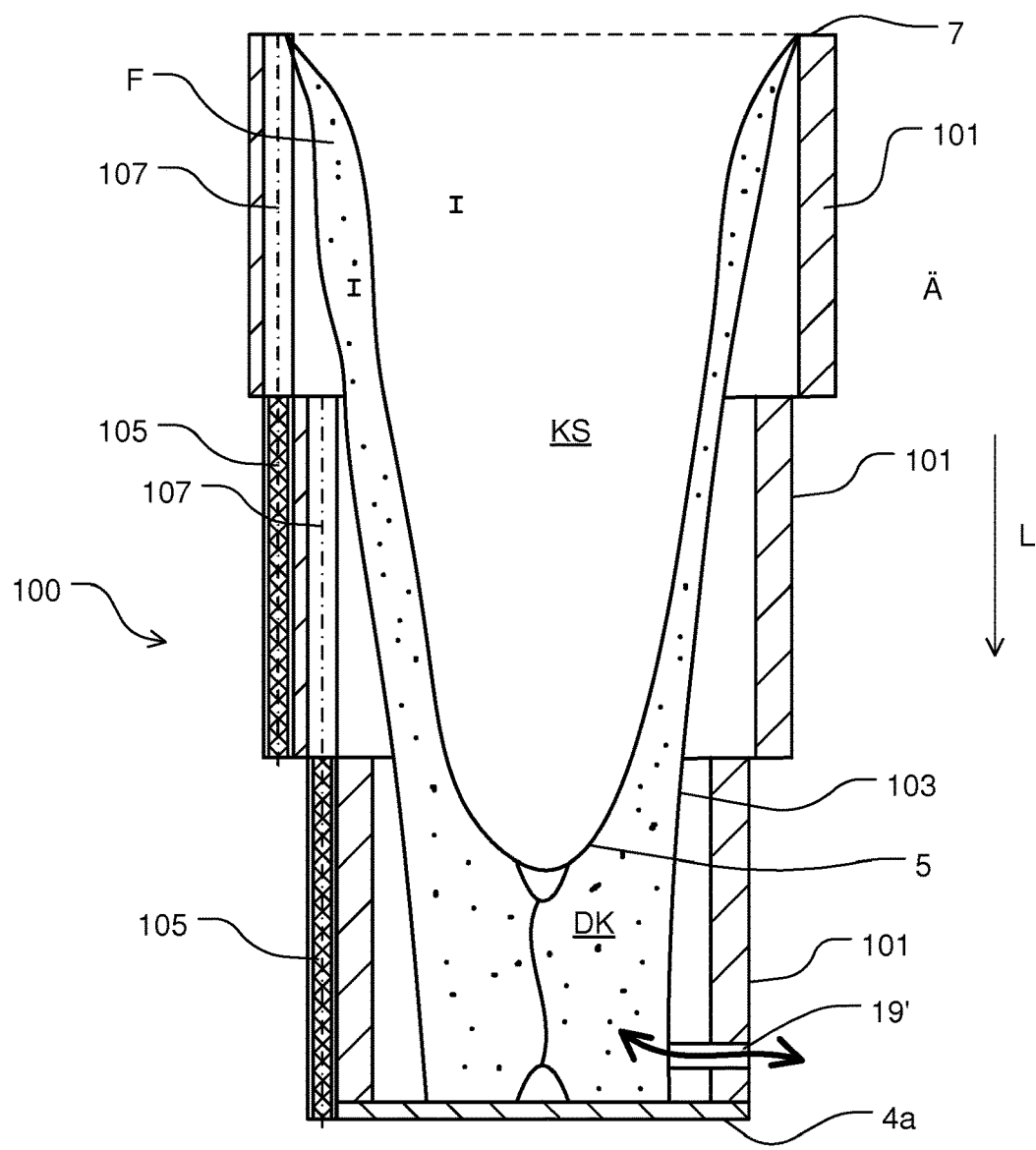
Figure 18:
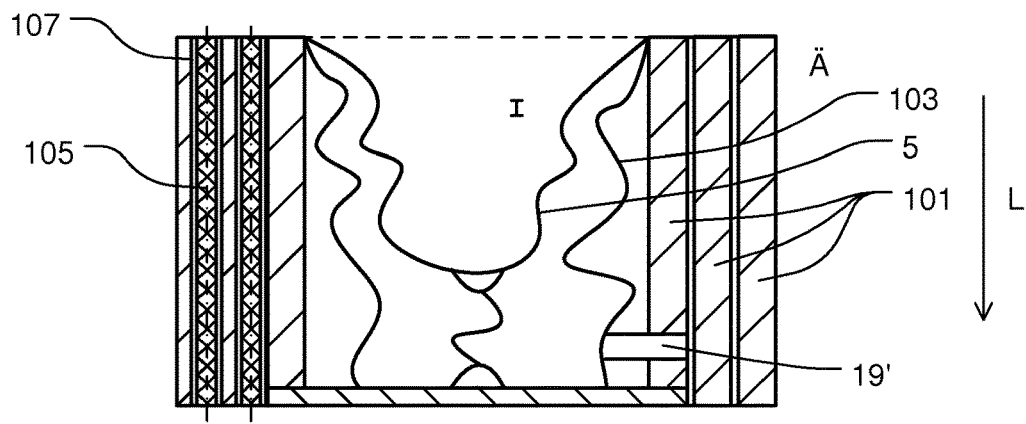
Figure 19:
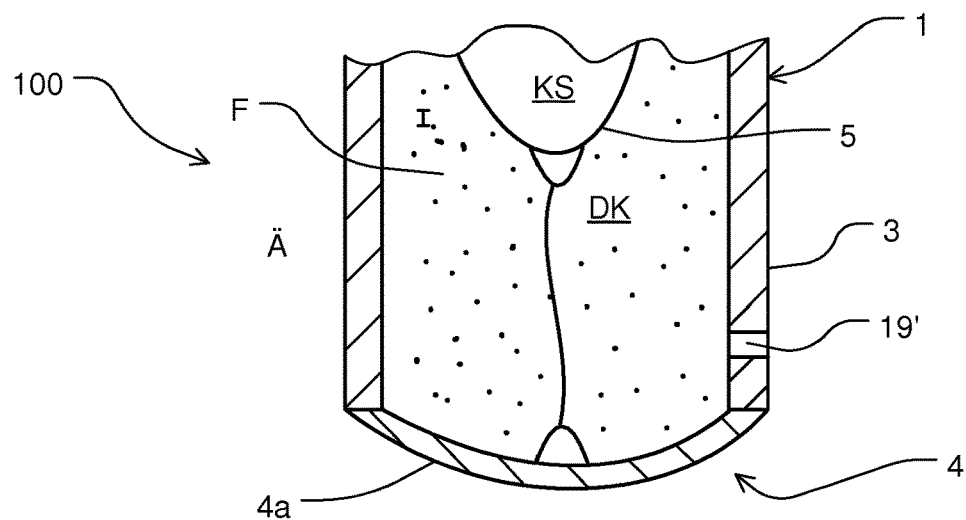
Figure 20:
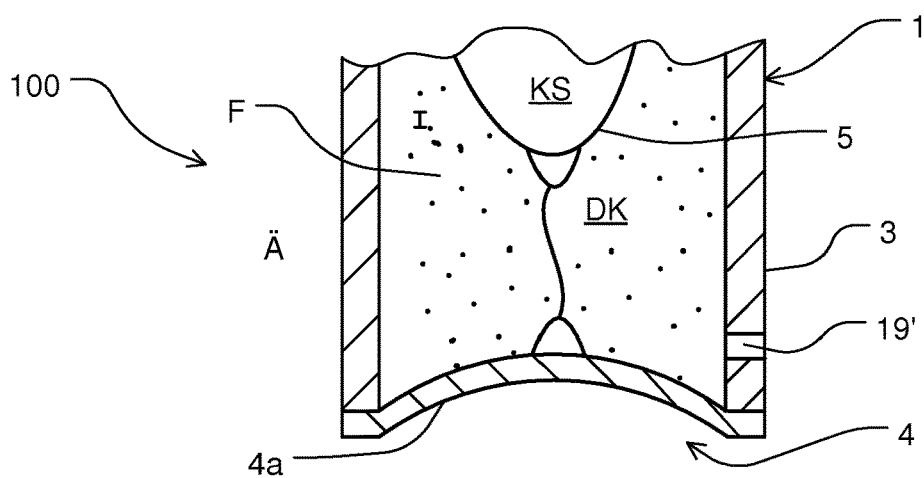
Figure 21:
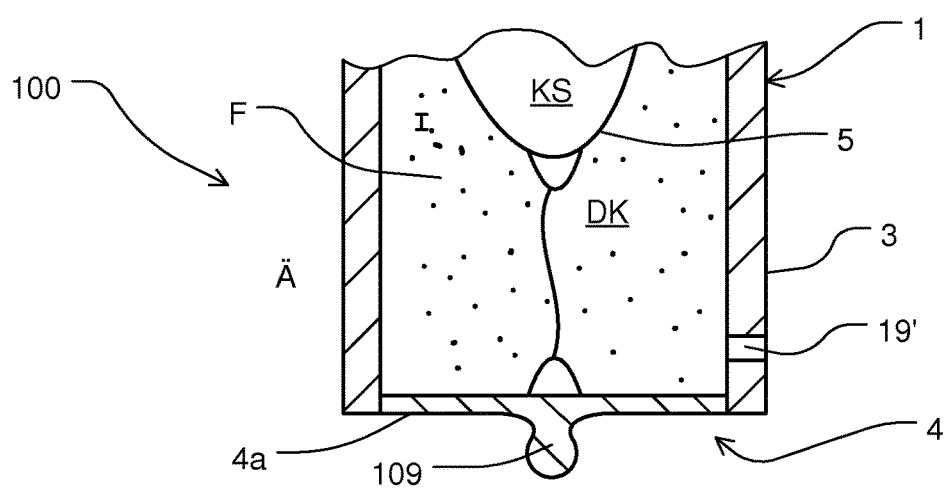
Figure 22:
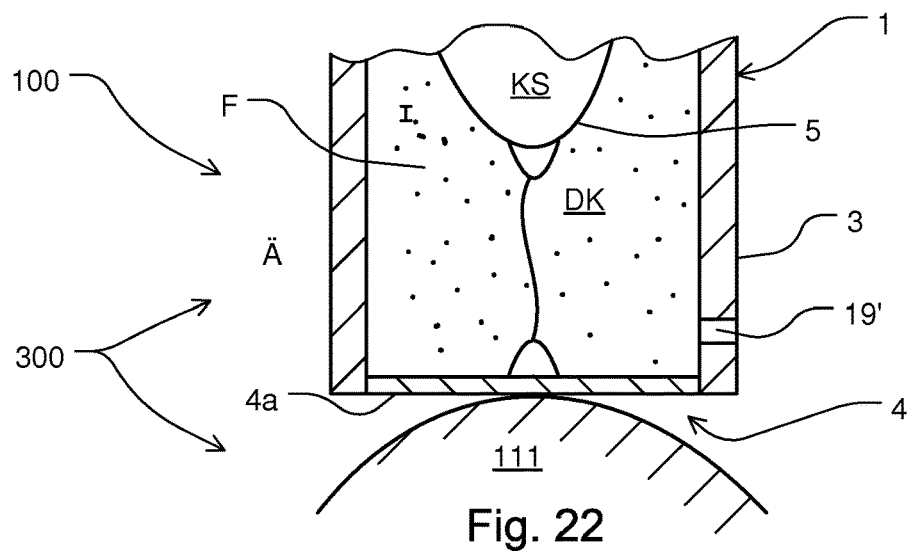
Figure 23:
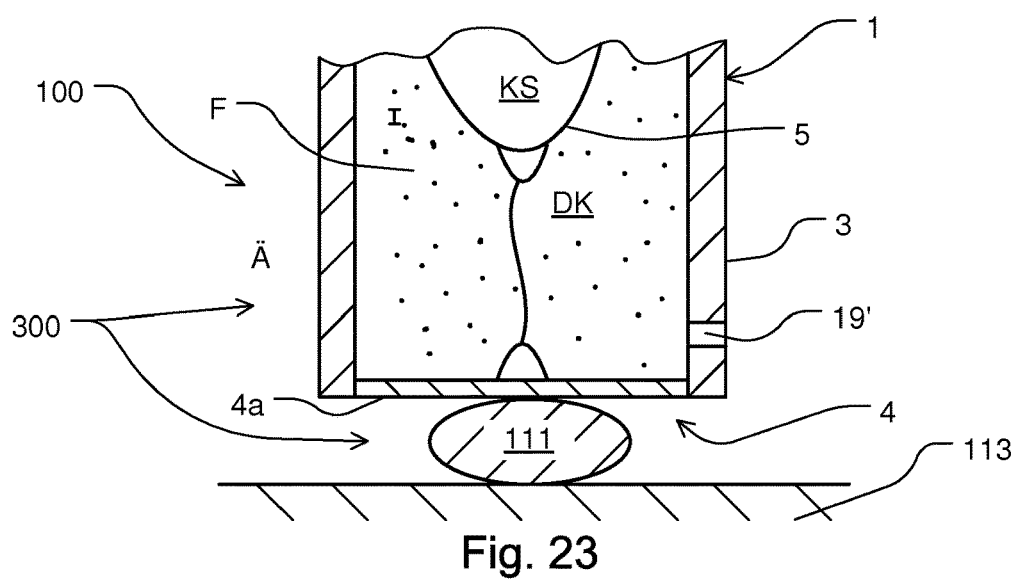
Figure 24:
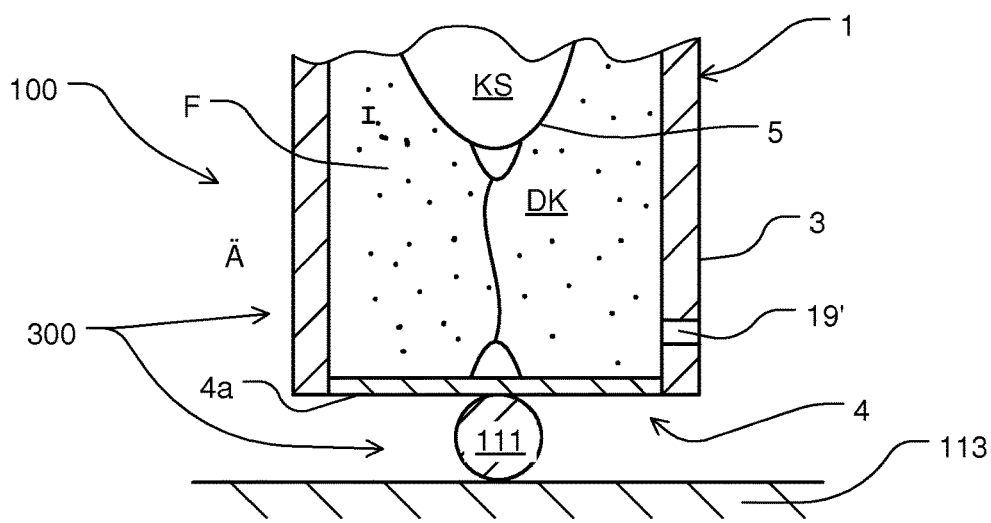
Figure 25:
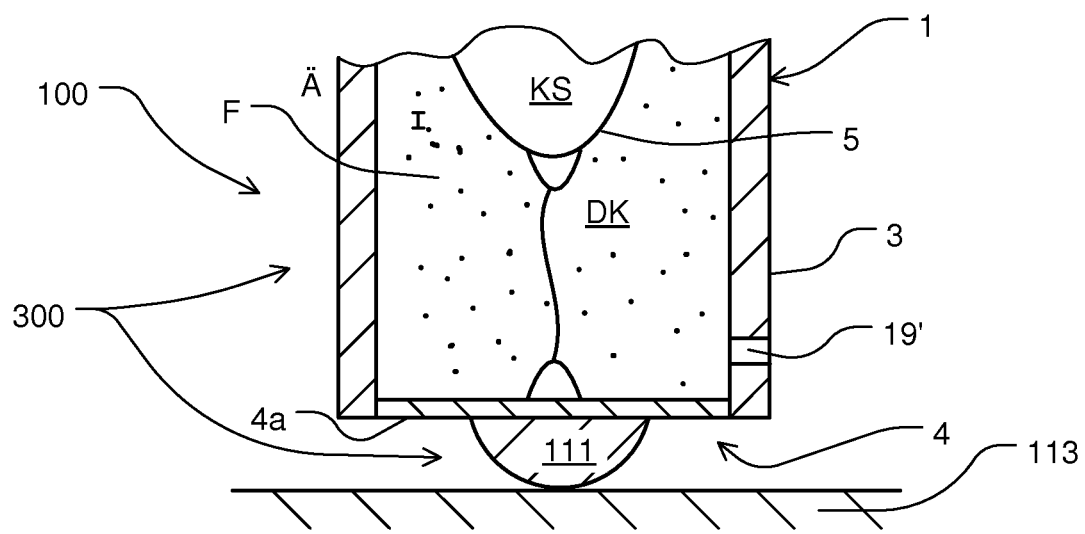
Figure 26:
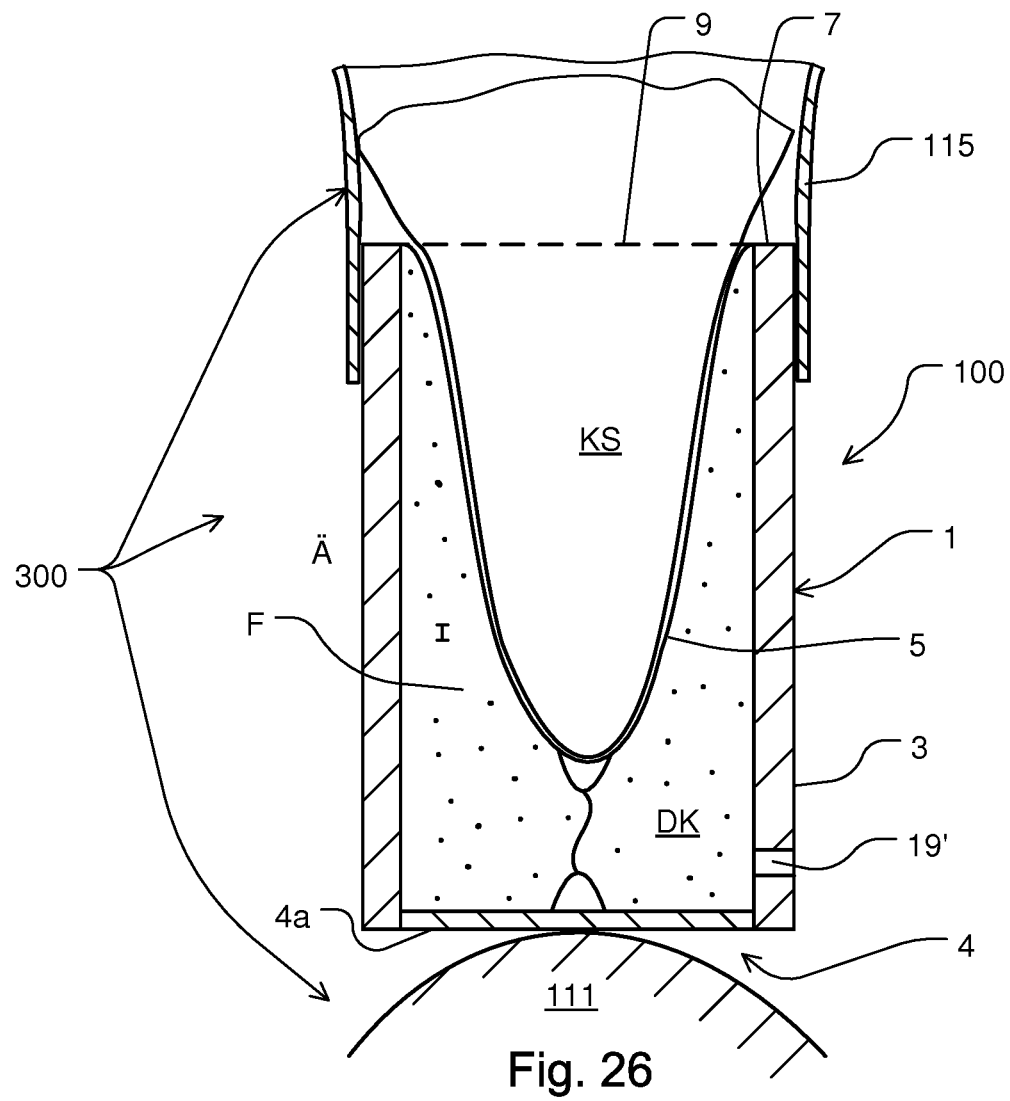
Figure 27:
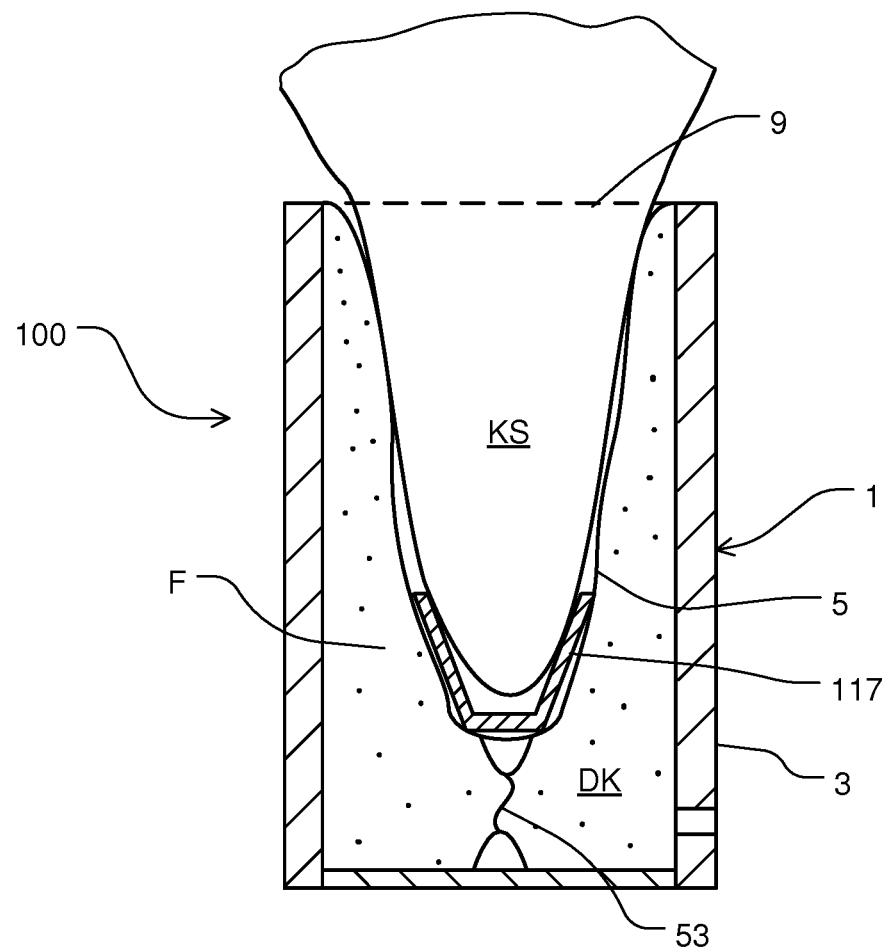
Figure 28:
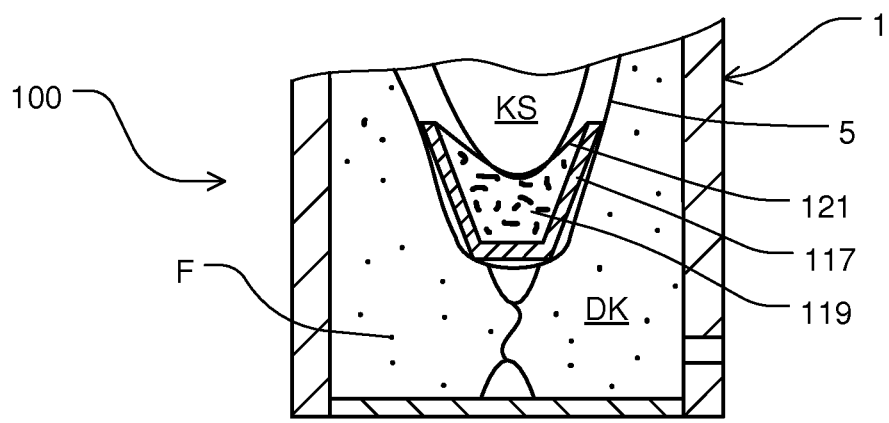
Figure 29:
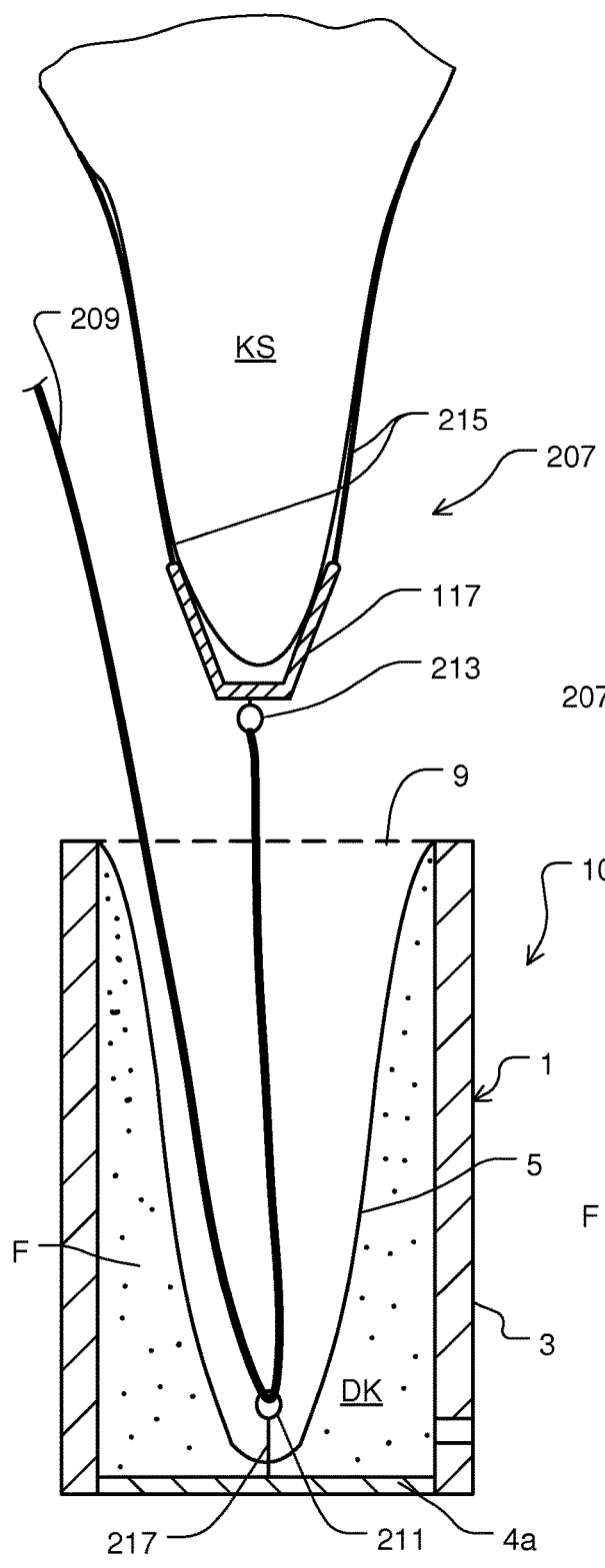
Figure 30:
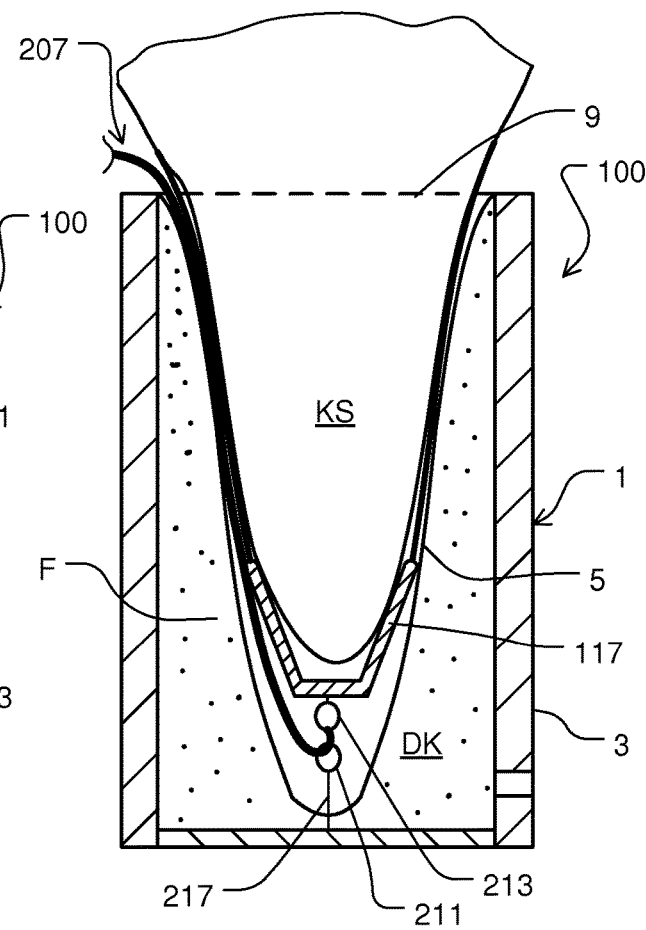
Figure 31:
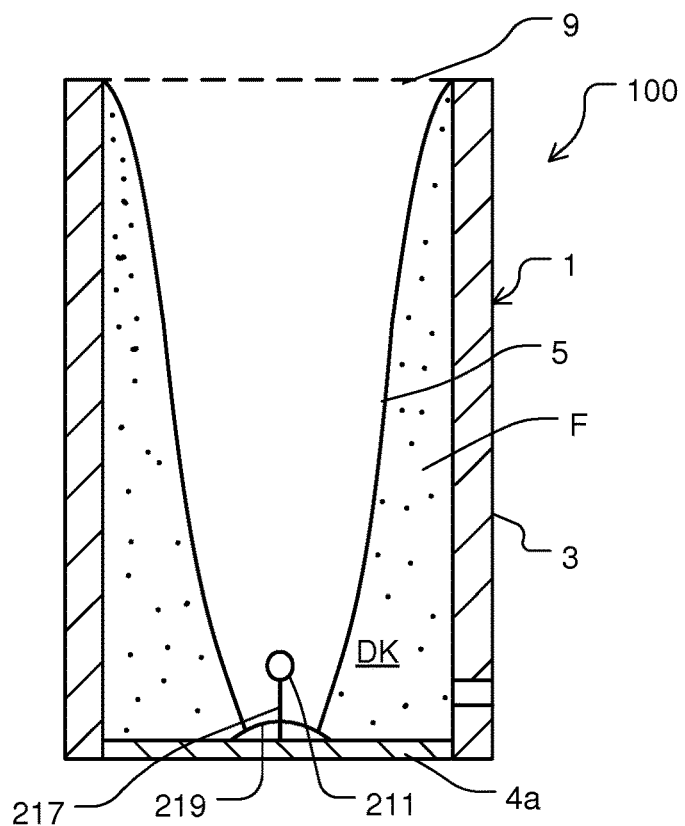
Figure 32:
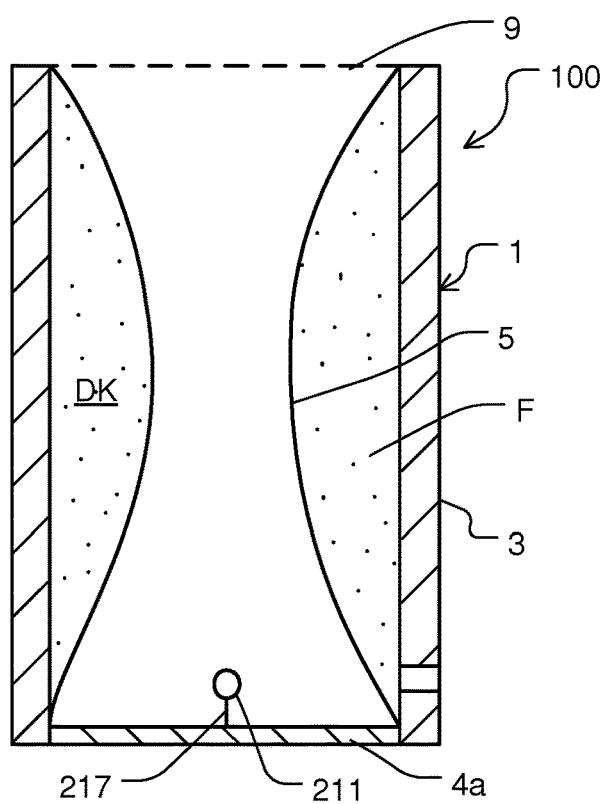
Figure 33:
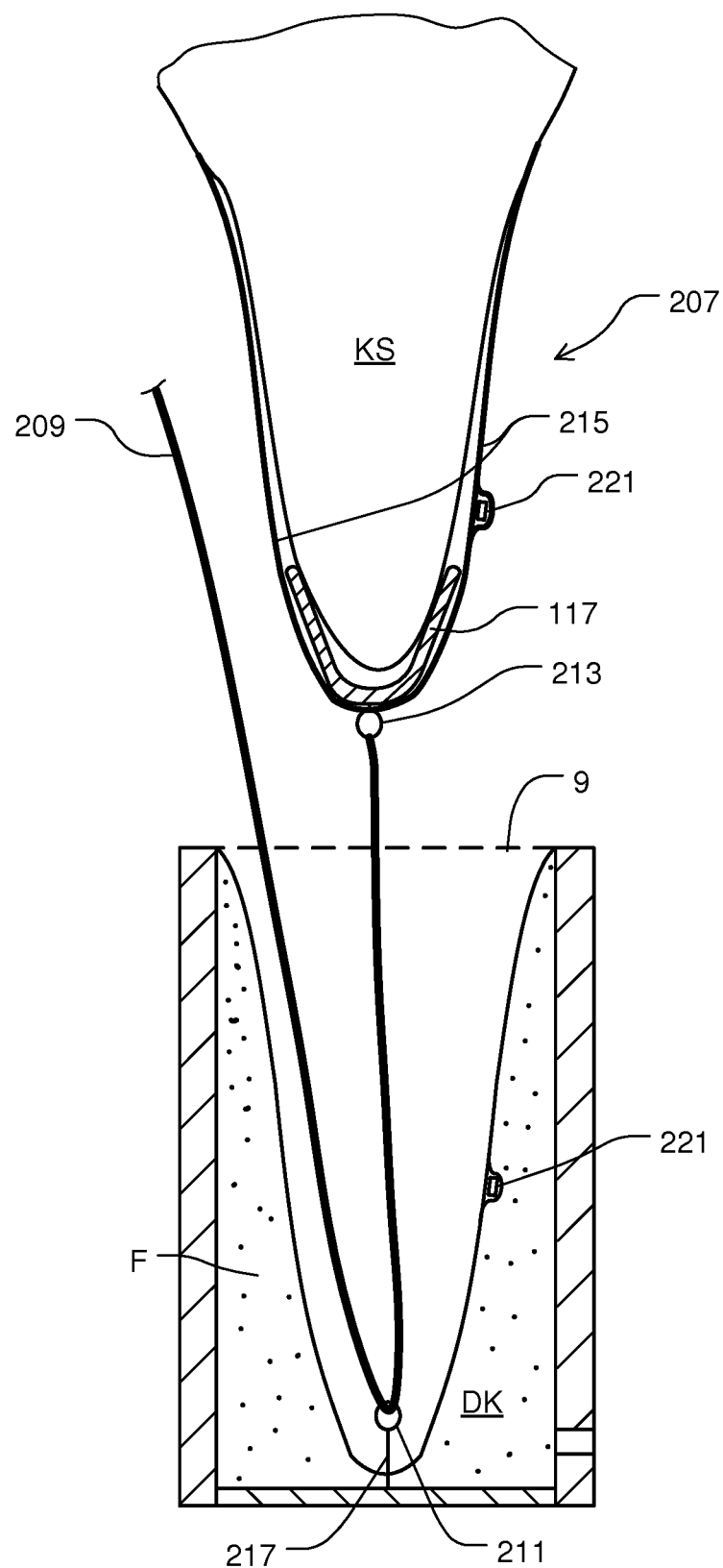
Figure 34:
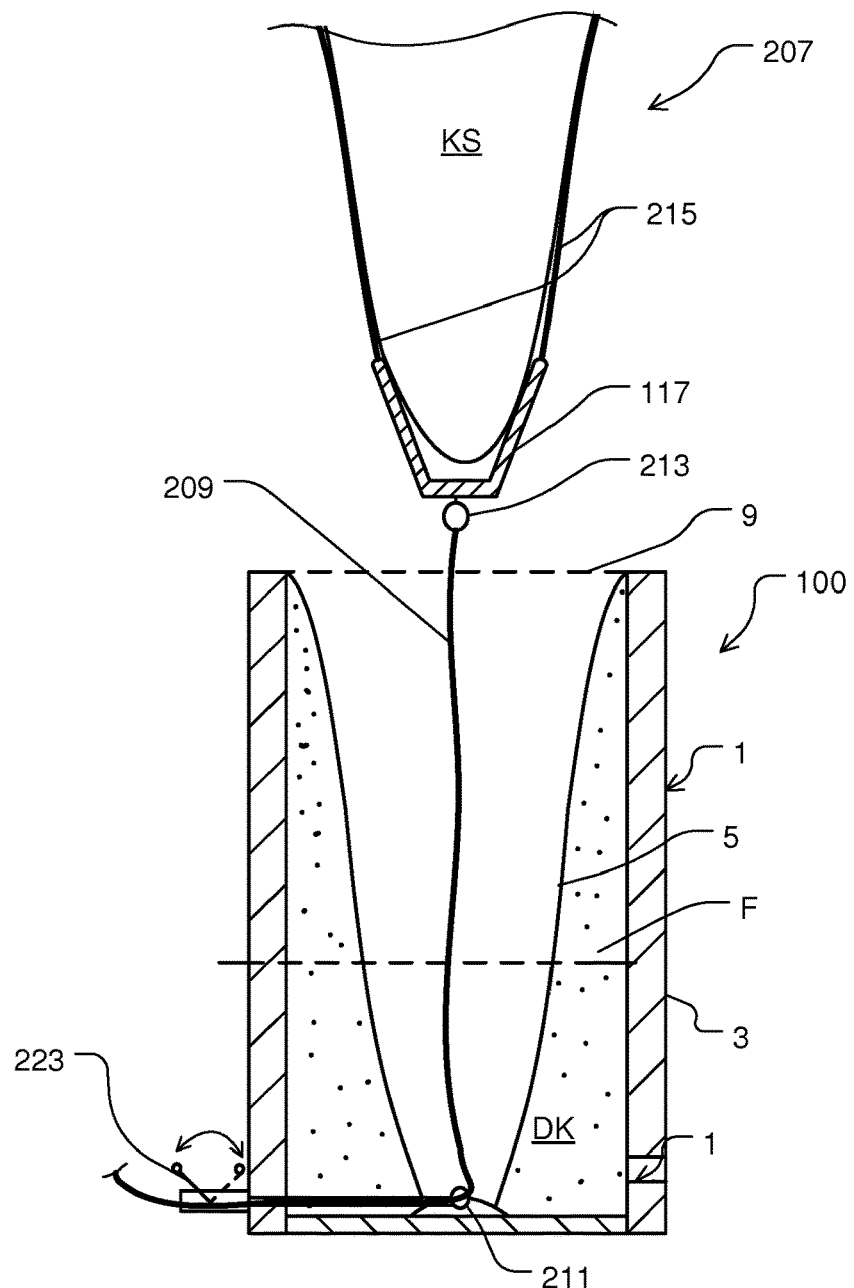
Figure 35:
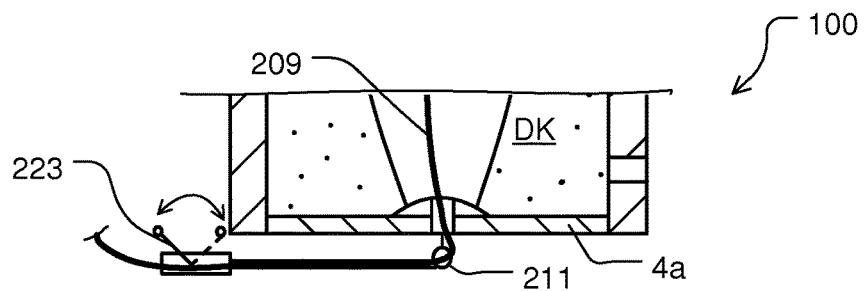
Figure 36:
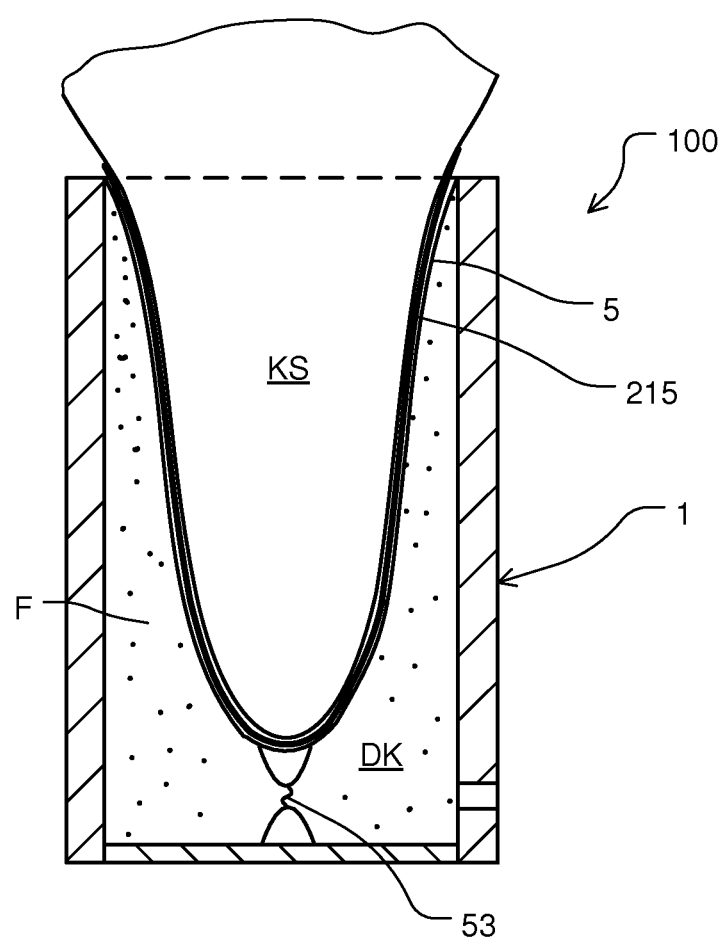
Figure 37:
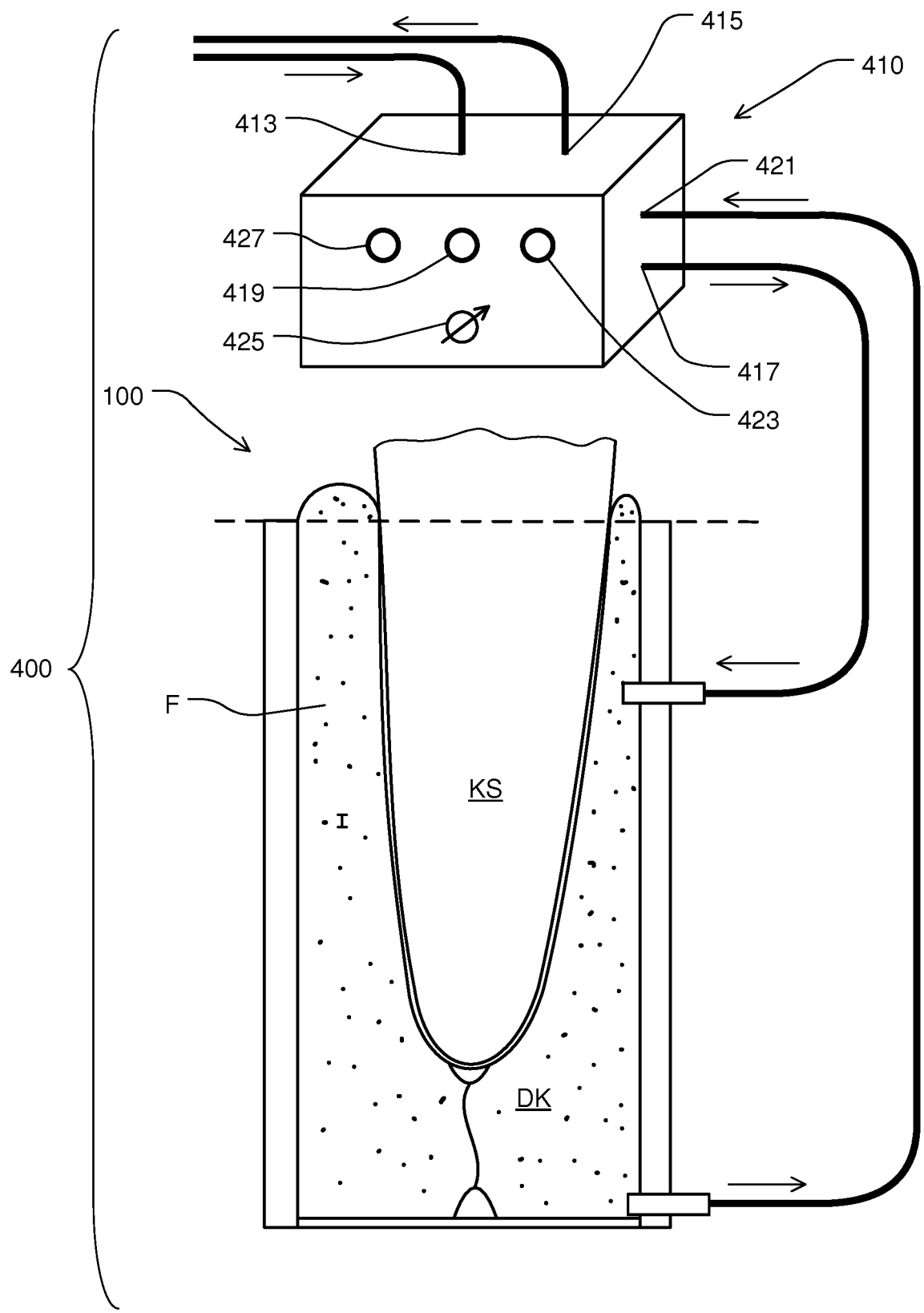
Figures 38, 39:
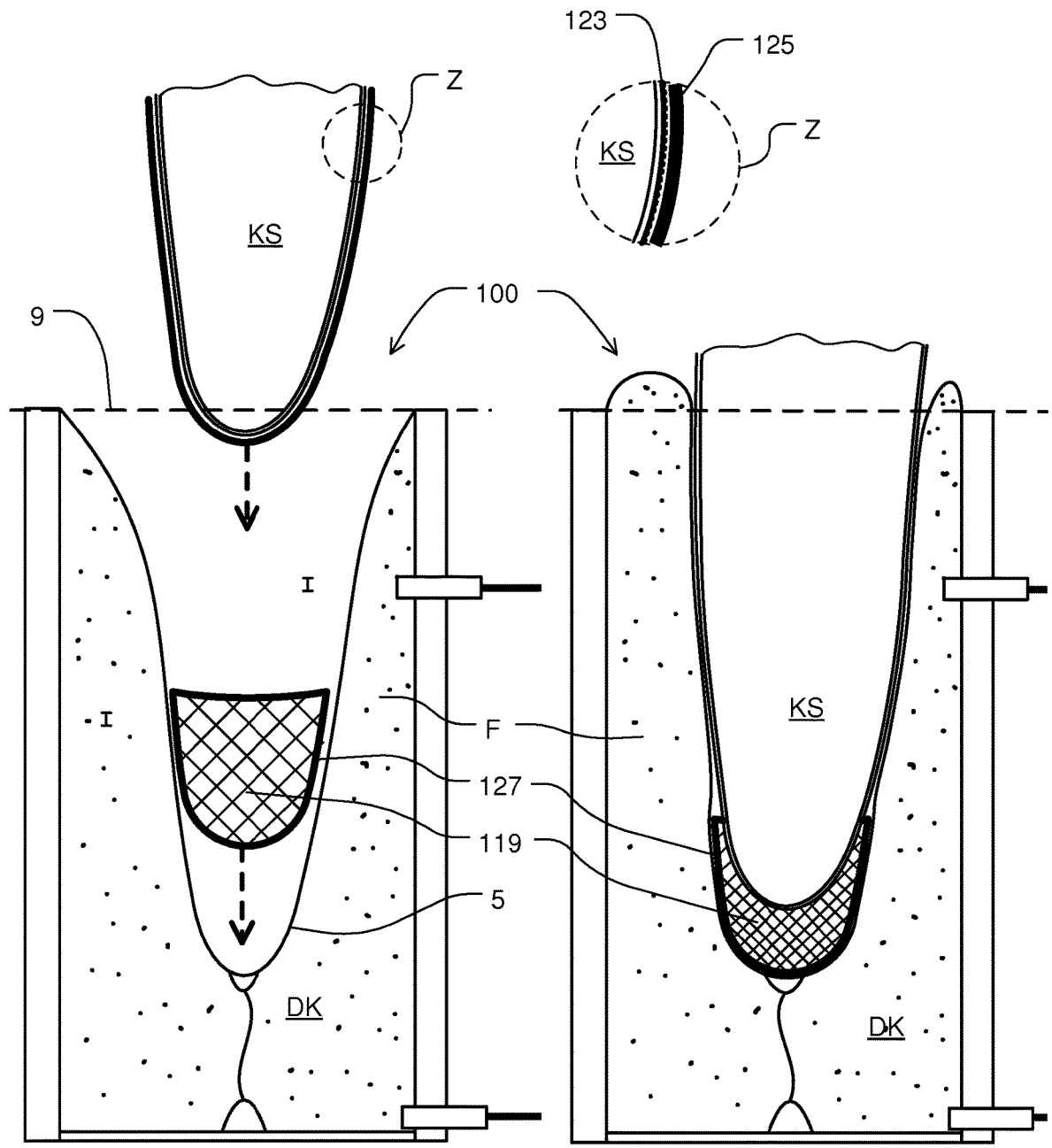
Figure 40:
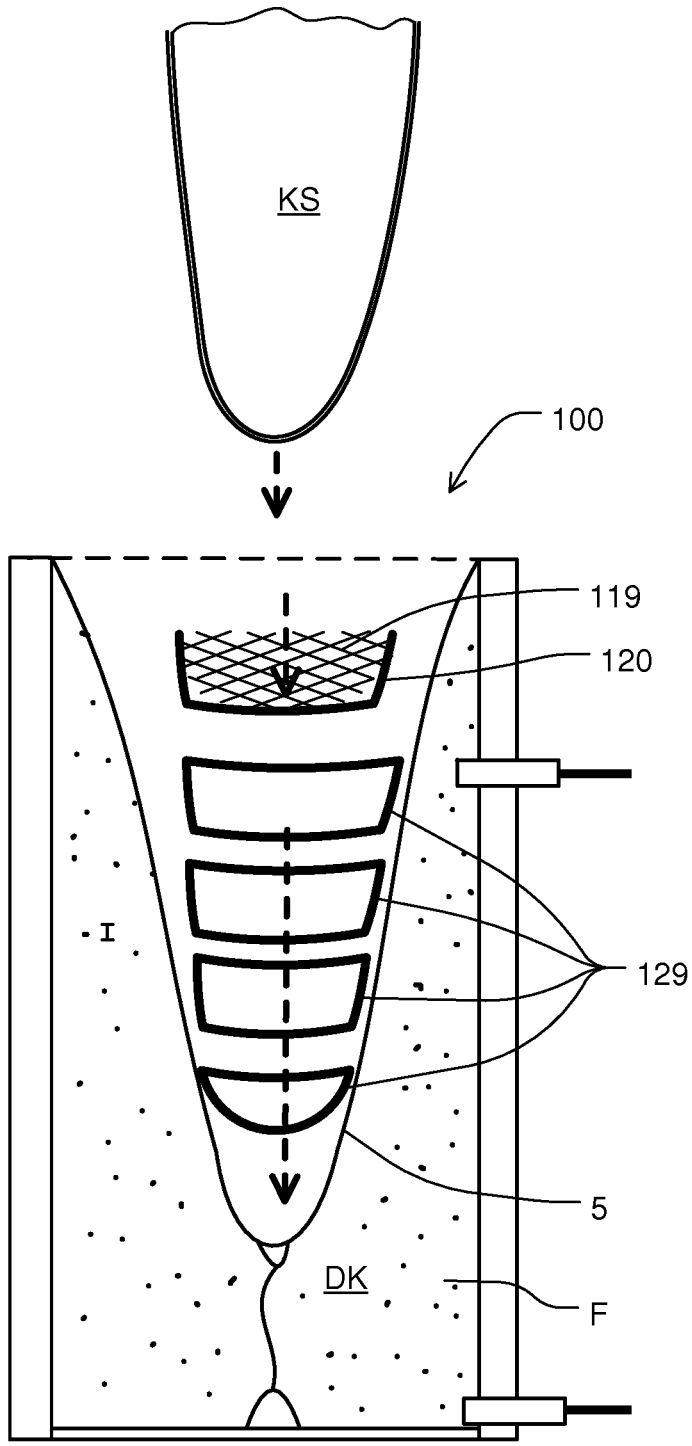
Figure 40A:
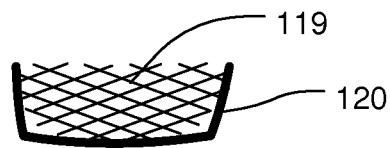
Figure 40B:
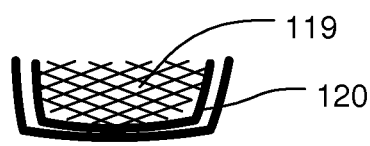
Figure 40C:
Figures 40D, 40E:
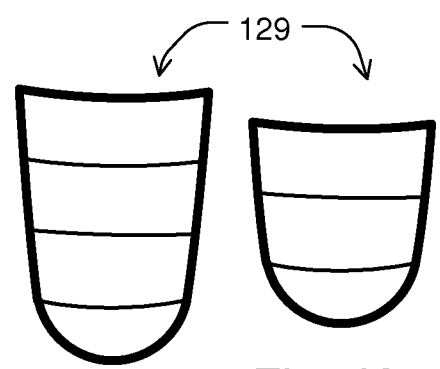
Figures 40F, 40G:
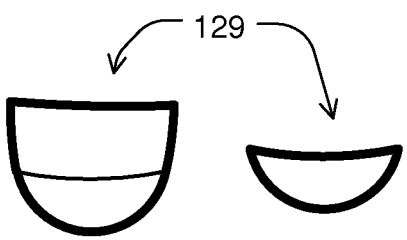
Figure 41:
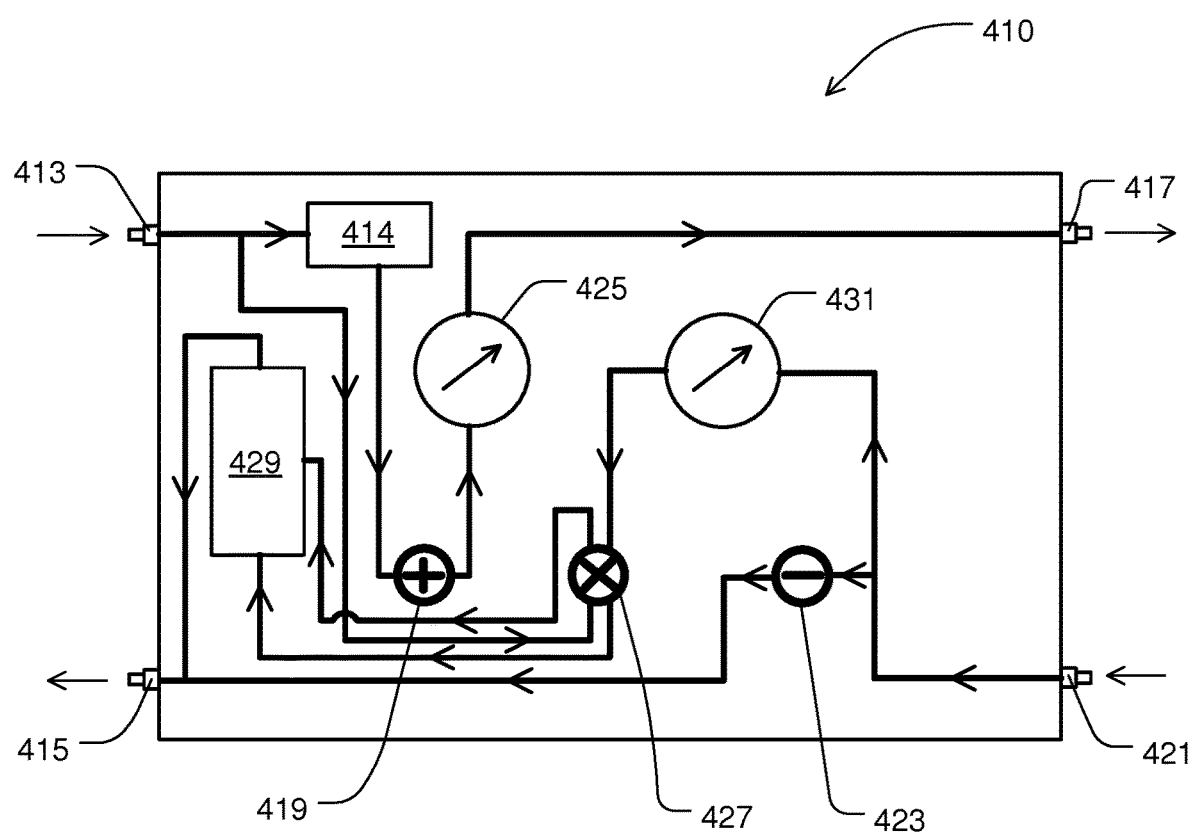

FIG. 6; shows a longitudinal cut of a sixth embodiment of an apparatus according to the present invention, from the side, which stands on a support or base surface or on an underground;

FIG. 7 shows a longitudinal cut of a seventh embodiment of an apparatus according to the present invention, from the side;

FIG. 8 shows a longitudinal cut of an eighth embodiment of an apparatus according to the present invention, from the side;

FIG. 9 shows a front view, with a slight perspective from the top, of a further embodiment of a membrane of an apparatus (not further illustrated) according to the present invention;

FIG. 10 shows a further embodiment of membrane of an apparatus (not further illustrated) according to the present invention;

FIG. 10a shows a membrane of an apparatus (not further illustrated) according to the present invention in a further embodiment;

FIG. 10b shows a membrane of an apparatus (not further illustrated) according to the present invention in another further embodiment;

FIG. 11 shows sections of a pressure vessel of an apparatus according to the present invention in a ninth embodiment;

FIG. 12 shows an apparatus according to the present invention in a tenth embodiment;

FIG. 13 shows an apparatus according to the present invention in an eleventh embodiment;

FIG. 14 shows an apparatus according to the present invention in a twelfth embodiment;

FIG. 15 shows an apparatus according to the present invention in a thirteenth embodiment;

FIG. 16 shows a calculation device according to the present invention;

FIG. 17 shows an apparatus according to the present invention with a multi-part wall in a fourteenth embodiment;

FIG. 18 shows the apparatus according to the present invention of FIG. 17 in a collapsed transport state;

FIG. 19 shows an apparatus according to the present invention with an outwardly convex (or curved) bottom area in a fifteenth embodiment;

FIG. 20 shows an apparatus according to the present invention with a concave bottom area in a sixteenth embodiment;

FIG. 21 shows an apparatus according to the present invention with a spherical lug in or at the bottom area in a seventeenth embodiment;

FIG. 22 shows a system according to the present invention with a medical apparatus according to the present invention and a contact surface separate therefrom;

FIG. 23 shows a system according to the present invention with an ellipsoid contact surface;

FIG. 24 shows a system according to the present invention with a spherical contact surface;

FIG. 25 shows a system according to the present invention with a contact surface connected to the bottom area of the apparatus;

FIG. 26 shows a system according to the present invention with a securing sleeve;

FIG. 27 shows an apparatus according to the present invention in an eighteenth embodiment having a release unit;

FIG. 28 shows an apparatus according to the present invention in a nineteenth embodiment having a further release unit;

FIG. 29 shows an apparatus according to the present invention in a twentieth embodiment having a hitch for fixing the limb stump in the pressure vessel;

FIG. 30 shows the arrangement of FIG. 29 with the limb stump fixed in the pressure vessel;

FIG. 31 shows the apparatus according to the present invention with the pressure vessel and a tube-shaped membrane;

FIG. 32 shows the apparatus according to the present invention with the pressure vessel and a further tube-shaped membrane;

FIG. 33 shows the apparatus according to the present invention with sensors in the adaptor and/or in the membrane;

FIG. 34 shows the apparatus according to the present invention with a device for fixing and/or adjusting the hitch;

FIG. 35 shows the apparatus according to the present invention with a further device for fixing and/or adjusting the hitch;

FIG. 36 shows a set according to the present invention with an adherent stocking and an apparatus according to the present invention;

FIG. 37 shows a unit according to the present invention with an apparatus according to the present invention and a pressurization control device according to the present invention;

FIG. 38 shows an apparatus according to the present invention with a form body for receiving the distal section of the limb stump and a composite adherent stocking;

FIG. 39 shows the arrangement of FIG. 38 in a combined or joined or assembled state;

FIG. 40; shows an apparatus according to the present invention with a multi-part form body for receiving the distal section of the limb stump;

FIG. 40a-c show different sizes of a compressible material and the associated shells for receiving the distal section of the limb stump;

FIG. 40d-g show diverse lengths of a multi-part form body for compensating the different lengths of limb stumps; and FIG. 41 shows a schematical arrangement of components within the pressurization control device.

Figure 1:
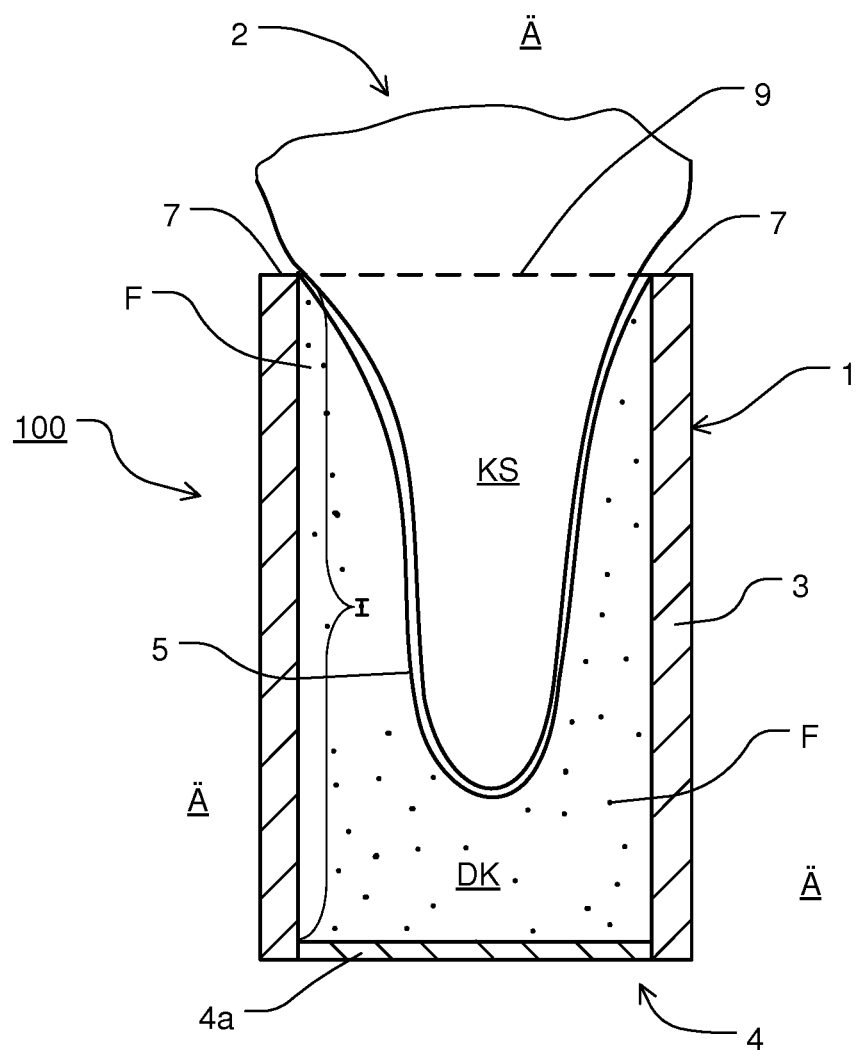
FIG. 1 shows a longitudinal cut of a first embodiment of an apparatus according to the present invention, from the side.

FIG. 1 shows a longitudinal cut (i.e. with respect to FIG. 1 from top to bottom) of a first embodiment of an apparatus 100 according to the present invention from the side.

The first embodiment shows thereby the simplest design of the apparatus 100 consisting of or comprising at least a pressure vessel 1 with a wall 3 and a membrane 5.

The pressure vessel 1, shown in FIG. 1 as purely optionally cylindrical, comprises optionally a first end side 2 (at the top in FIG. 1) and a second end side 4 (at the bottom in FIG. 1). The second end side 4 in the exemplary embodiment of FIG. 1 is fluid-tight sealed with a bottom plate or bottom area 4a against an exterior Ä. The bottom area 4a may be made of the same material as the wall 3.

The membrane 5 separates, in a fluid-tight manner, a fluid chamber or pressure chamber DK of the pressure vessel 1 from an exterior of the fluid chamber or pressure chamber DK, or exemplarily from the exterior Ä, i.e., a surrounding of the pressure vessel 1, or, as shown in FIG. 1, against a limb stump KS inserted into, or surrounded by, the membrane 5.

The membrane 5 may be fluid-tight connected to the pressure vessel 1 at an upper, usually ring-shaped, rectangular, square or differently shaped circumferential edge of the wall 3, or at another site.

The upper edge or rim 7 is situated in a plane in which there is an insertion opening 9 of the pressure vessel 1 or it delimits said insertion opening 9 at its circumference. The insertion opening 9 is situated in the plane which is indicated with a dashed line.

The insertion opening 9 serves inserting the limb stump KS which is wrapped with a wet plaster bandage 125, see below, in an interior I of the pressure vessel 1.

The interior I is the space delimited by the wall 3 of the pressure vessel 1. It extends from the second end side 4, which is fluid-tightly sealed with the bottom area 4a, to the insertion opening denoted with 9 and indicated by a dashed line.

The pressure chamber DK is filled with a fluid, here exemplarily with liquid F indicated with points. A filling with gas is also contemplated or covered by the present invention.

In FIG. 1, the apparatus 100 is illustrated showing the extremely schematically-indicated limb stump KS of the standing patient; said limb stump being inserted into the interior I such that it is surrounded by the membrane 5 at least in its distal section. The membrane 5 contacts the plaster bandage 125 at the limb stump KS like a second skin, wherein there may be further layers, like liners or the like, provided between plaster bandage 125 and membrane 5.

The limb stump KS is weighted or pressed with the full body weight of the standing patient. The amount of the liquid F is measured with regard to the known volume of the interior I or the pressure vessel 1 such that the limb stump KS may enter through the insertion opening 9 into the pressure vessel 1 at least so deep or far that the entire area of the plaster bandage 125 contacts the membrane 5; at least as much as it is relevant for the plaster impression. At the same time, the amount of liquid F is measured such that the distal end of the limb stump KS (at the bottom in FIG. 1) does not touch the bottom of the pressure vessel 1 or does not support itself on the bottom. In this way it is ensured that the patient rests with the inserted extremity on the pressure of the fluid and that the plaster bandage 125 undergoes or experiences at each point the same pressure by means of the membrane 5.

As is shown in the figure, the membrane 5, when no limb stump KS is inserted into the pressure vessel 1, lifts up or floats due to the pressure of the fluid, here of the liquid, and a liquid level is assumed (not shown in FIG. 1). Hence, the shape of the membrane 5, which is shown in FIG. 1, represents the form which the membrane 5 adopts under pressure when it rests on the inserted limb stump KS and is pulled under elastic stretching through the latter—in the example of FIG. 1—deep into the interior I towards the bottom area 4a.

It is further to be seen in FIG. 1 that due to the fact that wall 3 and the membrane 5 both prevent a fluid communication between the pressure chamber DK and the exterior Ä as well as prevent a fluid leakage out of the pressure chamber DK, they, hence, allow that the desired pressure builds up within the pressure chamber DK of the pressure vessel 1. However, they do not permit it to escape out of the latter or to be released.

As is seen in FIG. 1, the pressure chamber DK is thus formed by the membrane 5 and at least by parts of the wall 3 which, in this example, include also the bottom area 4a of the end side 4.

In exemplary embodiments of the present invention unlike those shown in FIG. 1, the pressure chamber DK may consist of or comprise a completely closed membrane, which may lie in the interior I of the pressure vessel 1 like a balloon or a bubble.

The pressure vessel 1, shown in FIG. 1 or in one of the following figures, as well as the pressure vessel of any other embodiment according to the present invention, may comprise a non-round cross section instead of a round one, preferably an edgy cross section. The cross section may exemplarily be rectangular, polygonal or square. Particularly during the automatic measuring, using a camera or the like as described herein, of the limb stump KS inserted into the apparatus 100, the last-mentioned cross sections may advantageously prevent or diminish artifacts which may be caused by the concave circumferential surface.

Figure 2:
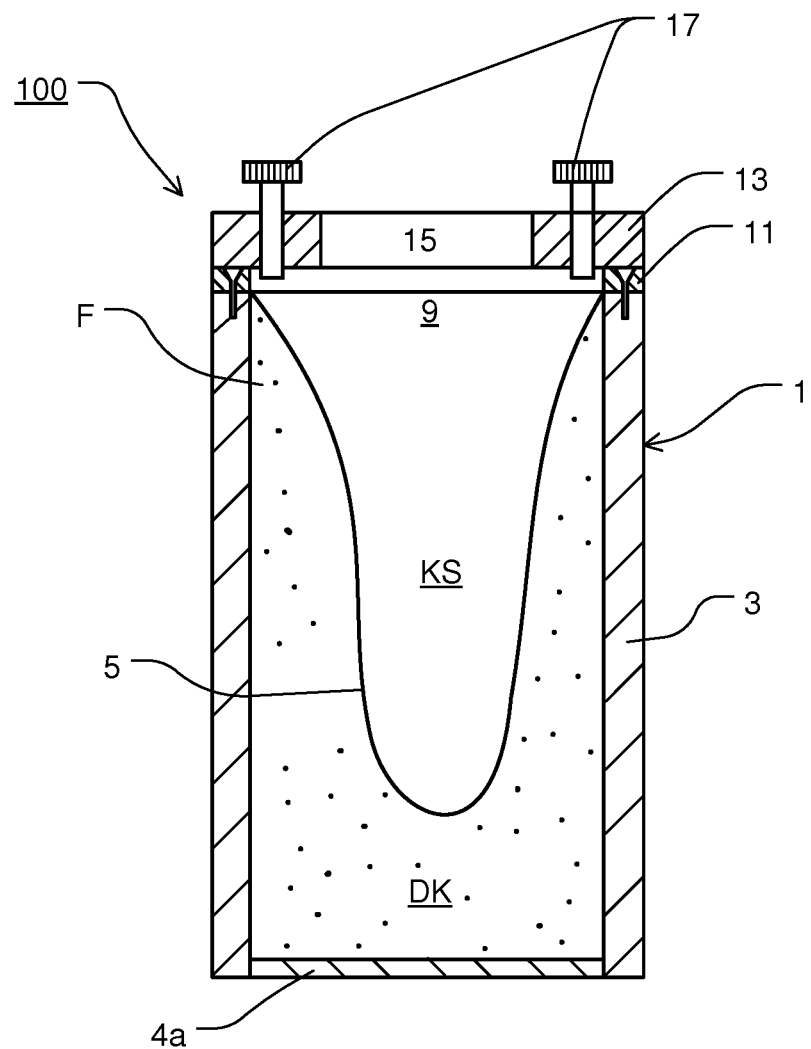
FIG. 2 shows a longitudinal cut of a second embodiment of an apparatus according to the present invention, from the side.

FIG. 2 shows a longitudinal cut of a second embodiment of an apparatus 100 according to the present invention, from the side.

The second embodiment substantially corresponds to the first embodiment shown in FIG. 1. Compared to the illustration of FIG. 1, a clamping ring 11 was added which may be provided, e.g., on the upper edge or wall 3 of the pressure vessel 1 so that it is clamped, or to be clamped, to the latter. The membrane 5 is detachably connected, in a fluid-tight manner against the interior of the pressure chamber, to the pressure vessel 1 between the upper edge and the clamping ring 11. This detachable arrangement allows the pressure vessel 1 to be connected quickly and with little effort to a membrane 5 adapted to the specific or individual circumstances or requirements or to the specific or individual patient. The detachable arrangement allows further advantageously to easily replace a damaged membrane 5.

Also the limiting ring 13, here a thigh sealing ring, shown in FIG. 2, is optional like the clamping ring 11. The limiting ring 13 may be one-piece or multiple piece and may be arranged such that it closes the insertion opening 9 excluding the leg opening 15. The size and/or form of the leg opening 15 is preferably chosen so that it tightly contacts or abuts on the limb stump KS or thigh. This prevents a floating of the membrane 5 past the limb stump KS and beyond the insertion opening 9, wherein the floating is caused by the pressure prevailing in the pressure vessel 1.

The limiting ring 13 may be screwed to the pressure vessel 1 via screws 17 or differently connected thereto in a detachable manner.

FIG. 1 and FIG. 2 show, as FIG. 6 does, a very simple embodiment of the present invention by which the pressure chamber DK comprises a steady or unchangable, predetermined amount of fluid. The pressure prevailing therein increases in the moment the patient presses with the limb stump KS on the membrane 5 through the insertion opening 9. If the amount of the fluid is appropriately selected depending on its compressibility, then no outlet is required for making corrections by adjusting the fluid amount. The remaining figures show on the other hand, embodiments in which such an adjustment is possible by having provided an outlet 19. These embodiments advantageously offer the possibility of adapting the apparatus to the specific or individual patient even if the latter already stands in the device 100 with his limb stump KS.

Figure 3:
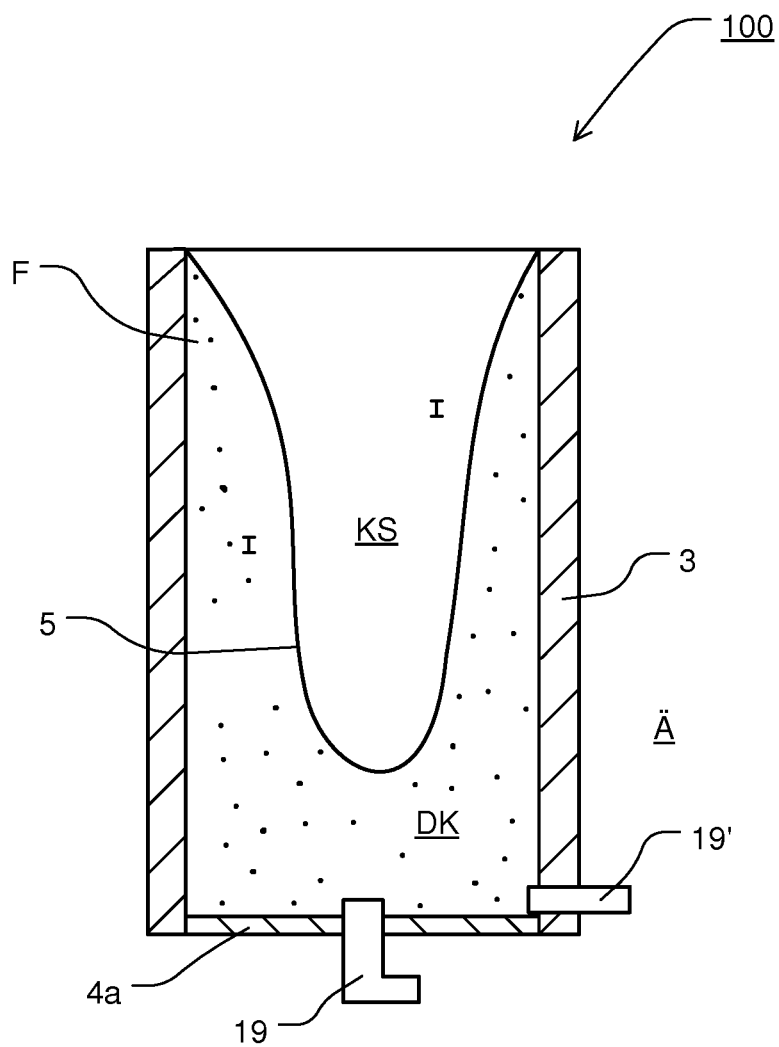
FIG. 3 shows a longitudinal cut of a third embodiment of an apparatus according to the present invention, from the side.

FIG. 3 shows a longitudinal cut of a third embodiment of an apparatus 100 according to the present invention, from the side.

The third embodiment substantially corresponds to the first embodiment shown in FIG. 1, wherein hatched illustration has been omitted as in the following figures. Compared to FIG. 1, an outlet 19 is added or provided in the bottom area 4a of the pressure vessel 1 and/or an outlet 19' is added in the side wall or wall 3 of the pressure vessel 1.

The outlet 19, 19' connects the interior I in the area of the pressure chamber DK to the exterior Ä of the pressure vessel 1. It allows the filling level and/or pressure within the pressure chamber DK to be specifically modified, for example by discharging fluid from the pressure chamber DK via the outlet 19, 19'. For this purpose, the outlet 19, 19' has a valve or stopcock (not presented in details) which can be fluid-tight closed. Notwithstanding its designation as an outlet, the latter may also be used for introducing fluid and thus for the filling of the pressure chamber DK.

Figure 4:
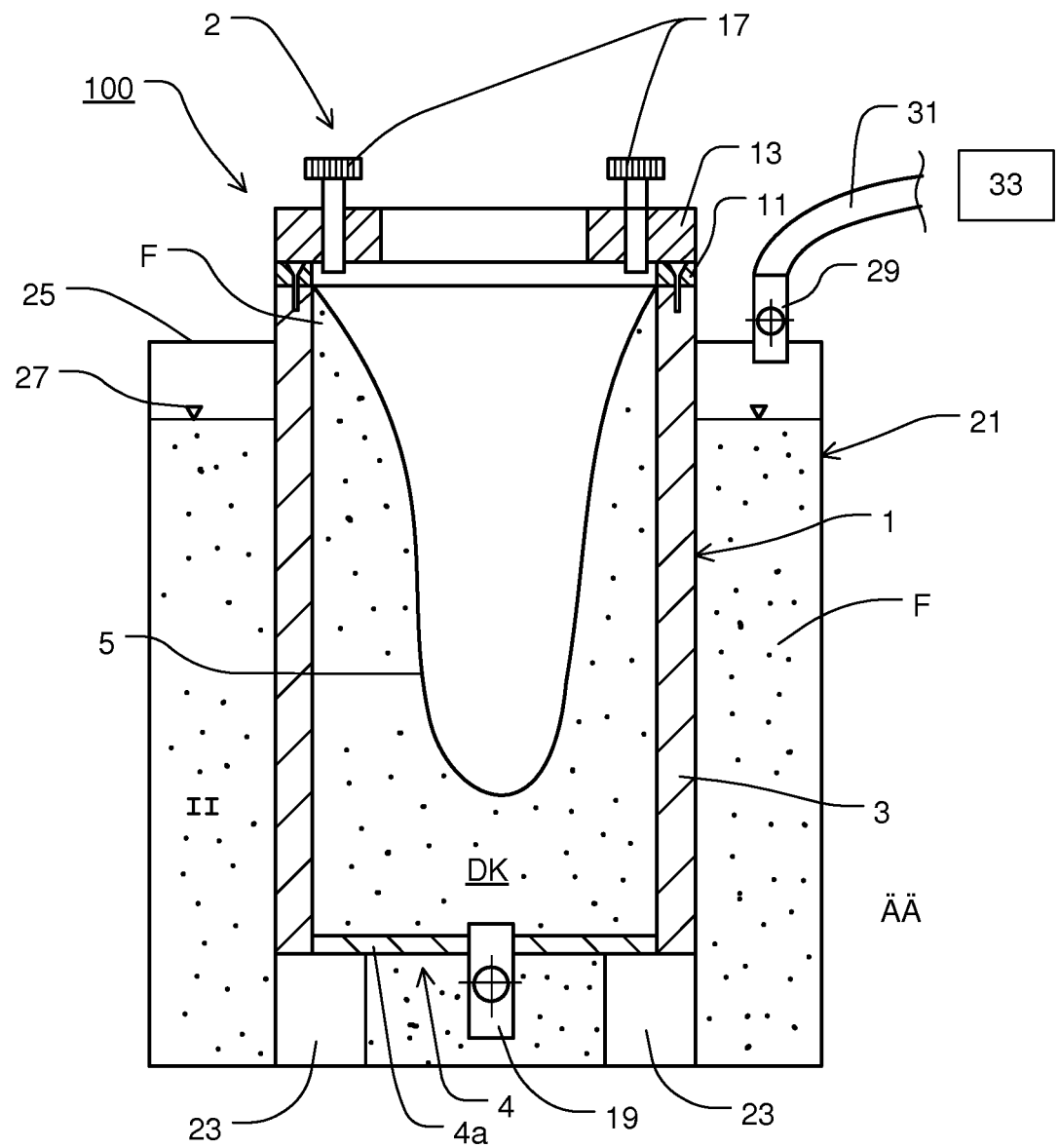
FIG. 4 shows a longitudinal cut of a fourth embodiment of an apparatus according to the present invention, from the side.

FIG. 4 shows a longitudinal cut of a fourth embodiment of an apparatus according to the present invention, from the side.

The fourth embodiment is based on the second embodiment shown in FIG. 2. The apparatus 100 comprises in addition to the pressure vessel 1 also a reservoir 21.

In this exemplary embodiment, the reservoir 21 surrounds at least partially the pressure vessel 1 which is resting on, e.g., its feet 23. An interior II of the reservoir 21 is in fluid communication with the pressure chamber DK of the pressure vessel 1 via the outlet 19 (this may comprise a valve or a stopcock). The fluid communication may be open or closed. A fluid exchange between the pressure chamber DK of the pressure vessel 1 and the interior II of the reservoir 21 may thus be permitted or prevented.

The feet 23 are a possible design of a mounting apparatus of the apparatus 100 by means of which the pressure vessel 1 may be mounted such that its first end side 2 is arranged at the top and its second end side 4 is arranged at the bottom (relative to the use state of the apparatus 100).

The interior II of the reservoir 21 may optionally be fluid-tight sealed against an exterior ÄÄ of the reservoir 21, for example by means of a cover 25.

A fluid is present in the interior II of the reservoir 21 as well as in the interior I of the pressure vessel 1. The fluid F has a level 27. The reservoir 21 may comprise an optional inlet 29 (which again may comprise a fluid-tight sealable valve or a stopcock), through which the interior II of the reservoir 21 may be connected to an again purely optional pressure source 33 by means of a pressure line 31. If the pressure in the interior II is increased by means of the pressure source 33 or in another manner with the inlet 29 being open, it also increases in the pressure chamber DK when the outlet 19 is also open, and vice versa. In this way, the pressure in the pressure chamber DK may be changed and adjusted with corresponding activation of the outlet 19 or inlet 29, respectively.

The fluid required to apply the desired pressure to the limb stump KS may thus be provided in the reservoir 21 of the apparatus 100, completely sealed off against the exterior ÄÄ. There is no need to supply fluid from external sources such as water lines, compressed air sources and the like, when using the apparatus 100 in these embodiments. The pressure which is applied by means of the pressure line 31 and/or to the fluid from the reservoir 21, may be generated by means of a manual air pump, bellows or the like, in particular without needing electrical voltage.

Figure 5:
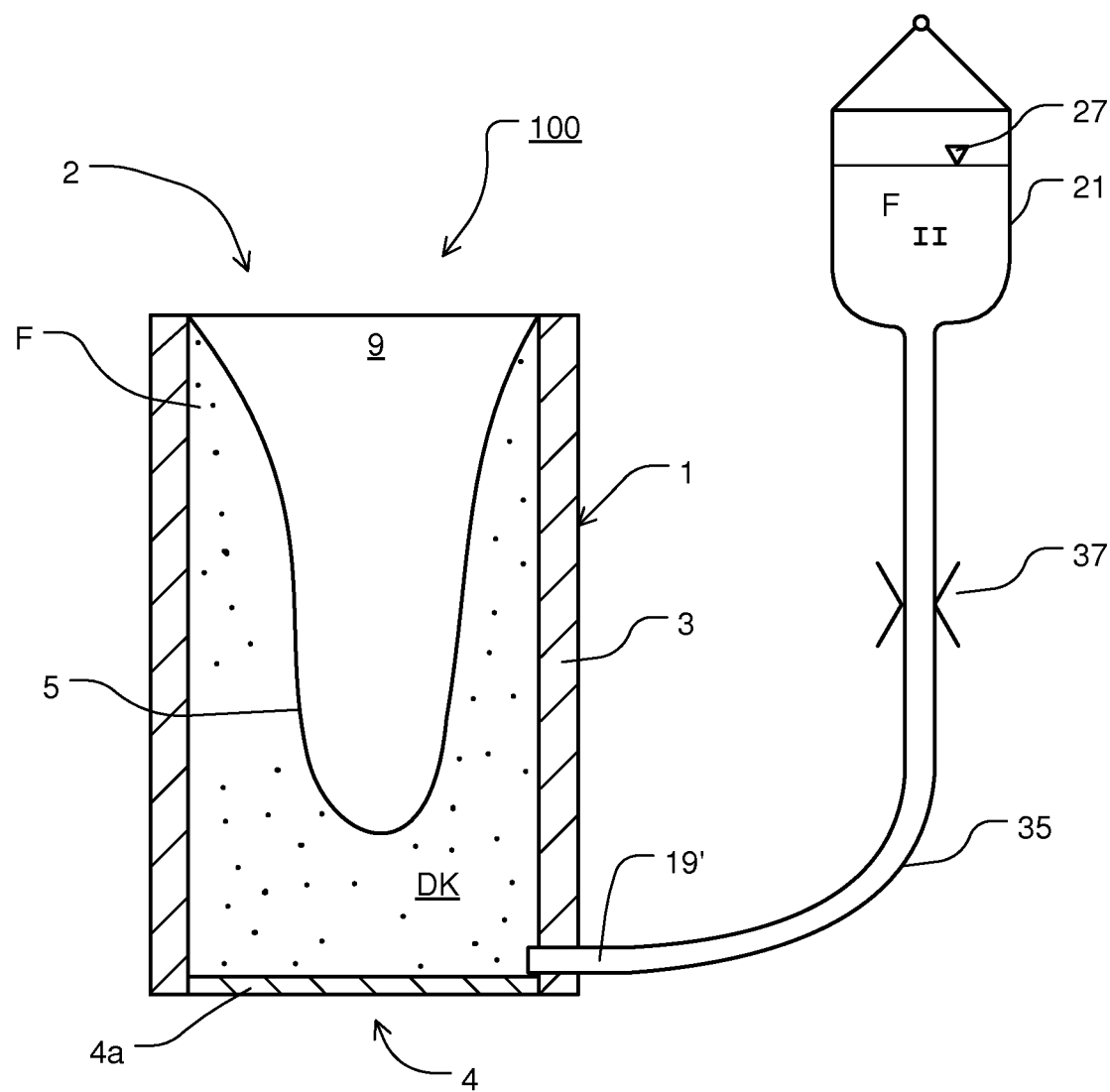
FIG. 5 shows a longitudinal cut of a fifth embodiment of an apparatus according to the present invention, from the side.

FIG. 5 shows a longitudinal cut of a fifth embodiment of an apparatus 100 according to the present invention, from the side.

As in the fourth embodiment, the apparatus 100 comprises both a pressure vessel 1 and a reservoir 21.

While the pressure vessel 1 of the embodiment shown in FIG. 4 is arranged in the interior II of the reservoir 21 such that the pressure chamber DK is directly in fluid communication with the interior II via the outlet 19, the pressure vessel 1 and reservoir 21 are situated separately or independent of each other in the fifth embodiment. They are however connected in fluid communication with each other via a compensating line 35. A flow regulating device, as e.g. a clamp 37, may be provided to prevent fluid flow within the compensating line 35. In addition or alternatively, the outlet 19' may comprise the a.m. valve or the a.m. stopcock.

As in FIG. 4, the reservoir 21 may optionally be connected to a pressure source. Alternatively however, it is often also sufficient to hold the reservoir 21 higher or lower or to press it or to reduce the pressure on it in order to change the pressure in the pressure chamber DK of the pressure vessel 1.

Closable or non-closable vent openings may optionally be provided at the reservoir 21. They may be provided for a pressure compensation.

FIG. 6 shows a longitudinal cut of a sixth embodiment of an apparatus 100 according to the present invention, from the side, which stands on a support or base surface or on an underground 39.

The apparatus 100 of FIG. 6 optionally comprises, regardless of all other features, a roller arrangement 41 with at least one roller or wheel. The roller arrangement 41 allows the apparatus 100, which may have a considerable weight in particular in a liquid-filled state, to be easily moved from one treatment room to the next.

The apparatus 100 of FIG. 6 further optionally comprises, again regardless of all the other features, at least one support 43, at which the patient who stands in the pressure vessel 1 may support him/herself with his/her limb stump KS. The support 43 may at the same time be used to guide or direct the apparatus 100, when the latter is to be rolled across the floor by the roller arrangement 41, if provided, like for example a pushcart or wheelbarrow.

The support 43 may optionally be designed to be adjustable. It may be adjustable in height (for example by means of the telescopic device indicated in FIG. 6), it may be adjustable in the inclination angle (relative to the underground 39) and/or it may comprise a handle 45.

The pressure vessel 1 may comprise in each embodiment according to the present invention an air release opening 47 from which the air that has been introduced already during the production process and for the transport, may escape when filling the pressure chamber DK of the pressure vessel 1, for example, with water. The air release opening 47 does not serve to introduce air or compressed air. It rather serves to ensure that the pressure vessel 1 or its pressure chamber DK is air-free after filling it with a liquid. This ensures that the later impression does not have eventual creases or other undesirable surface structures due to any air bubbles present or that the data model—or the data underlying it—obtained or resulted by the measurement, does not comprise any preventable fault due to air inclusion.

Preferably, the air release opening 47 is disposed in a section of the pressure vessel 1 or its wall 3, which is part of the pressure chamber DK, at a surface, side or end side of the pressure vessel 1 opposite to the outlet 19 or 19'. In this way, the water, introduced into the pressure chamber DK, may completely displace the air by using the different densities between water and air in the simplest and at the same time safest way.

FIG. 7 shows a longitudinal cut of a seventh embodiment of an apparatus 100 according to the present invention, from the side.

In FIG. 7, the pressure chamber DK of the pressure vessel 1 is filled with enough fluid, e.g. water, so that the membrane is bulged outwards beyond the insertion opening 9, i.e., to the exterior Ä of the pressure vessel 1, wherein it is not the interior I of the pressure vessel 1 that enlarges or increases, rather the volume of the pressure chamber DK.

The patient can now get with his or her limb stump KS into the pressure vessel 1 through the insertion opening 9 in a particular easy way. To do that, he/she places the distal end of the limb stump KS on the tip or places the upper region of the membrane 5 onto, for example, where the double arrow in FIG. 7 points. When the limb stump KS is lowered in the direction of the arrow, the latter enters into the pressure vessel 1 through the insertion opening 9 and thereby takes along the membrane 5 limb stump KS by inverting it. The membrane 5 finally assumes its form shown in, e.g., FIG. 1. This appears to be the most convenient way of entering the limb stump KS into the interior I of the pressure vessel 1, where it is surrounded by portions of the pressure chamber DK. This applies in particular due to the fact that the limb stump KS is to be inserted into the interior I against the initial pressure which already exists in the pressure chamber DK at the beginning of the insertion of the limb stump KS into the interior I, wherein this pressure may aggravatingly still increase during this insertion due to space required in the interior by the limb stump KS. The fluid or water displaced from the pressure chamber DK by the limb stump KS during the insertion may be discharged by means of the outlet 19, for example into a reservoir 21 (not shown in FIG. 7), with which the pressure chamber DK may be connected in fluid communication by means of the compensating line 35. The fluid required to bulge the membrane 5, as is shown in FIG. 7, may previously have been introduced through the outlet 19 too. It may have been taken or removed from the reservoir 21.

The outlet 19 is closed when the desired depth for inserting the limb stump KS into the interior I of the pressure vessel 1 is reached. The a.m. markings which are not shown in FIG. 7 may exemplarily determine if said insertion depth has been reached. In addition, it is possible to determine if the insertion desired depth is reached by making a side comparison (left leg to the right leg or hip oblique position). Once the insertion desired depth is reached and outlet 19 is closed, then the patient may load the limb stump KS with full body weight. The pressure, which then acts on the plaster bandage (if present) or on the limb stump KS due to the uniform pressure distribution on all surface areas of the surface of the plaster bandage or of the limb stump KS within the pressure chamber DK, results in an optimum data model from a measurement or in a modeling of the resulting plaster impression which optimally corresponds to a prosthesis shaft for the later load situation. These embodiments are not limited to those shown in FIG. 7.

FIG. 8 shows a longitudinal cut of an eighth embodiment of an apparatus according to the present invention, from the side.

The pressure chamber DK is formed by the wall 3 (illustrated in cut), which includes here the bottom area 4a, and the membrane 5.

The membrane 5 is, preferably in its distal, middle or central section or area, connected to a section 51 of the wall 3 or of the end side in a frictional manner. In the embodiment shown in FIG. 8, the frictional connection is effected by a connector 53, which extends from a distal end of the membrane 5 to the section 51, here purely optionally, the bottom area 4a of the pressure chamber DK.

The connector 53 may be a thread, as is shown in FIG. 8 by way of example. Any other suitable connector, such as a tape or Velcro or the like, is also encompassed by the present invention.

The connector 53 keeps the membrane 5 connected to the pressure vessel 1 or to the bottom area 4a, preferably in the area of the second end side 4 of the pressure vessel 1, in particular in the area of the bottom area 4a and preferably in the center thereof, in a frictional and/or positive and/or firmly-bonded manner.

It is preferred that the connector 53 completely or substantially completely allows a circulation of the distal end of the limb stump KS, at least in the state of use of the apparatus 100, that is, when the limb stump KS is inserted into the pressure chamber DK. A circulation of the limb stump KS is thus still advantageously possible in FIG. 8, except for the surface which corresponds to the cross section of the connector 53. In this way, a floating or a pressure lift or uplifting also of the distal section of the limb stump KS caused by the fluid may occur unchanged; said floating or pressure lift being important for feeling or sensing the load or pressure later in the finished shaft.

In addition to the connector 53 shown in FIG. 8, several or further connectors may be provided. These, like the connector 53, may be connected to the bottom area 4a. They may alternatively or additionally be connected to the pressure chamber DK or to the pressure vessel 1 at another section of the wall 3 than the end side or bottom area 4a. This also applies to the connector 53 shown in FIG. 8.

The connection between connector 53 on the one hand and wall 3 or bottom area 4a on the other hand may—as the connection, independent thereof between connector 53 on the one side and membrane 5 on the other—be an adhesive connection, a screw connection, a plug connection, a snap connection a latch connection or the like. It may be releasable or non-releasable.

The connector 53 shown in FIG. 8, as also preferably each connector of FIG. 1, FIG. 11 and FIG. 12, is not elastically extensible. It is preferably not extensible.

The membrane 5 shown in FIG. 8 is likewise preferably not stretchable and/or non-elastic in the longitudinal direction L.

The form of the membrane 5 shown in FIG. 8, into which the limb stump KS is not yet introduced, i.e. empty, is purely exemplary. The membrane 5 may become more folded together than shown in FIG. 8 due to the pressure of the fluid F. In fact, opposing sections of the membrane 5—when viewed from above, i.e., in the direction from the first end side 2 to the second end side 4—may, at least in sections of the membrane which have a certain distance to the insertion opening 9, contact each other or lie on each other forming a slit-like shape. When viewed from the top of the insertion opening 9, may possibly show an insertion opening formed centrally by the membrane, see above. Said insertion opening may have a diameter of 3 cm or more.

In FIG. 8, an optionally present inlet and/or outlet 19 or 19' is not illustrated, but is nevertheless optionally provided. This also applies to FIGS. 11 and 12.

FIG. 9 shows a membrane 5 of an apparatus 100 according to the present invention, which is not further illustrated, in a further embodiment from the front with a slight perspective from above.

The membrane 5 is made of a material which has a different elasticity in a first direction of the material than in a second direction, which is here only exemplarily, a direction perpendicular to the first direction. The first direction can be described or identified by the courses of longitudinal fibers 55 of the membrane 5, the second direction by the courses of circumferential or transverse fibers 57.

The longitudinal fibers 55 can be less elastic than the circumferential fibers 57 or (in particular with identical force or pressure application) allow a smaller deformation of the membrane in the longitudinal direction than in the circumferential direction. In the extreme case, the longitudinal fibers 55 according to the present invention are not elastic and/or not stretchable, but the circumferential fibers 57 are preferably stretchable. The membrane 5 does not stretch or expand, or does so only slightly, in the longitudinal direction L (from the top downwards in FIG. 9), while it can lay on or be applied to the limb stump KS in the circumferential direction and can stretch to a required extent in a transverse direction Q.

The longitudinal direction L may correspond to the a.m. insertion direction.

The reference numeral 58 denotes a middle or central region or section of the membrane 5, here the distal tip of the membrane 5.

FIG. 10 shows a membrane 5 of an apparatus 100 (not further illustrated) according to the present invention in a further embodiment.

The membrane 5 is shown in the cut-open state, in which it does not take the form in which it is used in the apparatus 100. It could be brought into the form shown in FIG. 9, which is ready for use, by joining its left and right edges together and cutting them where necessary.

Two exemplary pairs of longitudinal fibers and transverse fibers, each of which is designated by 55a or 57a and 55b or 57b, respectively, which are perpendicular to each other only by way of example, are to be seen here.

The longitudinal fiber 55a is stretched and therefore does not allow any further elongation in the longitudinal direction L. The transverse fiber 57a to be considered in connection therewith can, on the other hand, due to its waved or wavy course or material in the matrix of the membrane 5 which is made of, in addition to fibers, silicone or comprises the latter, allow a stretching of the membrane 5 in the transverse direction Q. Thus the longitudinal fiber 55a and the transverse fiber 57a differ from each other in their extensibility.

In the two exemplary fibers 55b and 57b being considered, the same effect may be achieved in another way. The longitudinal fiber 55b is made thick and therefore cannot stretch or, compared to the corresponding thinner transverse fiber 57b, stretches less.

No need to mention that the membrane 5 may comprise more than the fibers shown here. Also not worth mentioning is that the membrane 5 preferably comprises longitudinal fibers and transverse fibers 55a and 57a or longitudinal fibers and transverse fibers 55b and 57b, but preferably not both pairs of the longitudinal and transverse fibers discussed here.

FIG. 10a and FIG. 10b show similar to the illustration of FIG. 10, membranes 5 with longitudinal fibers 55 and transverse fibers 57, wherein the transverse fibers 57 connect the longitudinal fibers 55.

The longitudinal fibers 55 are straight, while the transverse fibers 57 are transverse or also longitudinal between adjacent (alternatively non-adjacent) longitudinal fibers 55.

To this end, the transverse fibers 57 extend, as shown in FIGS. 10a and 10b, e.g. in a zig-zag form. They may thereby extend, as in FIG. 10a, in a single zig-zag form, in a double zig-zag form, as in FIG. 10b, or in a multiple zig-zag form, not shown.

In this, the transverse fibers 57 and the longitudinal fibers 55 may also be of the same material and/or of the same thickness. It is their arrangement relative to the longitudinal direction which makes the membrane 5 stretchable (in transverse direction Q) (or more stretchable) or (in longitudinal direction) not stretchable (or less stretchable).

If the longitudinal fibers 55—unlike in FIGS. 10a and 10b—are not straight, but rather have a more or less strong zig-zag course about a line in longitudinal direction L, then a desired shortening of the membrane in the longitudinal direction may be advantageously achieved when the membrane is loaded or weighted due to the insertion of the limb stump KS. The possible shortening may thereby be adjusted or limited in advance by matching the stretching and the size of the zig-zag pattern of the longitudinal fibers 55 and/or of the transverse fibers 57. A shortening may be advantageous in that a lengthening of the membrane 5 and/or its undesired floating on a structural level may be countered simply and still effectively.

FIG. 11 shows a sectional side view of a lower section or the second end side 4 of a pressure vessel 1 of an apparatus 100 according to the present invention in a ninth embodiment.

The membrane 5 is connected with its lower section 61 by a connector 53. The connector 53 is in turn connected to the bottom area 4a of the pressure chamber DK, preferably in the middle or centrally. In this way, the membrane 5 may be prevented to float in the longitudinal direction toward the insertion opening (in FIG. 11 to upwards). It also cannot extend—or not beyond a desired point—from the insertion opening into the exterior Ä.

As can be seen in FIG. 11, also a longer limb stump KS could be inserted into the membrane 5. Material 62 is still present between the lower section 61 of the membrane 5 and the area of the membrane 5 which area is filled by the limb stump KS, wherein the membrane 5 is compressed by the pressure of the fluid F.

The connector 53 comprises, here purely exemplarily, a shell 63 in which the membrane 5, here for example, is glued with its lower section 61, or is connected in another way fixedly or releasably, for example by means of a hook-eye connection.

Optionally, the shell 63 is manufactured as one-piece with the membrane 5.

In the example of FIG. 11, the shell 63 is connected to a socket 67 via a thread 65. The socket 67 is screwed to the bottom area 4a, but could also be connected differently, or be an integral part of the wall 3, for example the front or bottom area 4a.

By means of the thread 65, the membrane 5 may advantageously be detached from the wall 3 or the bottom area 4a. Other releasable or non-releasable connections such as plug-in connections, clamping connections, screw connections, etc., are also contemplated by the present invention.

FIG. 12 shows a sectional side view of the pressure vessel 1 of an apparatus 100 according to the present invention in a tenth embodiment.

In its wall 3 and/or bottom area 4a, the pressure vessel 1 comprises, for measuring or scanning the dimensions of the limb stump KS, two or more cameras 71 (or other devices as described supra, the cameras 71 are purely exemplary; they are also exemplary for all other devices which are partially non-optical devices).

The scanning may be achieved, for example, by simply determining the difference or the distance between the camera (or another device, e.g. an ultrasound device or an infrared device) or wall 3 on the one hand and membrane 5 (or plaster surface or skin surface) on the other hand. The scanning may be performed on a sufficient number of planes having different heights (the height may be determined from the insertion opening 9 or its plane or from the bottom area 4a), for example, by means of infrared or ultrasound or other devices/measurement methods mentioned herein. A volume model or a surface data model may be calculated in a manner known to the person skilled in the art based on these distances and the knowledge of the angle at which they were measured.

Scanning may also be carried out by methods as described in the disclosures WO 09/015455 A1, WO 2009/052602 A1 and WO 2010/111768 A1, also from Ming Zhang et al., "Finite element modelling of a residual lower limb in a prosthetic socket: a survey of development in the first decade", Medical Engineering & Physics, Volume 20, No. 5, 1998, pages 360-373, Elsevier Science Ltd. ISSN: 1350-4533, and Douglas T et al: Ultrasound imaging in lower limb Prosthetics, IEEE Transactions on Neural System and Rehabilitation Engineering Vol. 10, No. 1, March 2002 (2002-03), pages 11-21, IEEE, USA, ISSN: 1534-4320 (XP11078071). The corresponding disclosures of documents referred to herein are hereby incorporated by reference. The corresponding content thereof is hereby incorporated by reference.

FIG. 13 shows a sectional side view of an apparatus 100 according to the present invention in an eleventh embodiment. Cameras 71 are connected to a device 73, which is configured to transfer the data collected by means of the cameras 71 or by another device mentioned herein into a data model (data collection which may optionally have a matrix format). The data model may be computationally processed in a known, suitable manner and may reflect the surface or other information on the geometry, inter alia, of the limb stump KS.

The device 73 may be configured to process the data transmitted to it before the completed data model is created. Smoothing processes, reconstruction algorithms and correction factors may be implemented or done during this processing.

The device 73 may be configured to store and/or output the data model in a known file format. A corresponding output device may be provided, as well as a suitable display device for displaying the data model or representation based thereon, in particular of the limb stump KS or the shaft to be produced. The data model thus created may be used elsewhere to create a shaft. For this purpose, the file which contains the data model may be sent, e.g., to a remote workshop for prosthesis shafts, which is likewise encompassed by the present invention.

However, the data model may also be connected in signal communication with a shaping device 75 adapted to manufacture the prosthesis shaft on the basis of the data model of the limb stump KS or the shaft to be manufactured for the limb stump KS. The signal connection may be wired or "wireless".

FIG. 14 shows a sectional side view of an apparatus 100 according to the present invention with the limb stump KS inserted.

The membrane 5 is connected to the bottom area 4*a* by a connector 51. The connector 51 is not (or only slightly) elastic or stretchable. The membrane 5 is also not (or only slightly) elastic or stretchable in the longitudinal direction.

The connector 51 allows the membrane 5 to float proximally (upward in FIG. 14). Therefore, a more or less annular, but in any case closed-in-its-circumference, uplifting or floating 81 arises at the second end side 2. The uplifting or floating 81 is to be seen, due to the sectional illustration in FIG. 14, as protrusions left and right of the limb stump KS.

The membrane 5 touches or contacts the limb stump KS (or a plaster bandage, a liner or the like being pulled thereover) at a contact point surface 83, which is more or less annular but in any case closed in its circumference. The contact point surface 83 is the circumferentially closed line or surface which comprises the points at which the limb stump KS has a final or closing proximal contact with the membrane 5. The contact point surface may also be referred to as contact area.

At the same time, the membrane 5, at its radial circumference in the area of the second end side 2 of the wall 3, contacts, or is fixed with, a transition section 85 which is likewise closed in its circumference. The transition section 85 may be understood to be an area in which the limitation of the pressure chamber DK passes or merges from a limitation through the wall 3 into a limitation through the membrane 5. This can be well seen in FIG. 14 in that the pressure chamber DK below the arrow tip of the reference numeral line of the reference numeral 85 is only limited by the wall 3; above only by the membrane 5, which itself cannot be supported against a section of the wall 3.

The floating 81 may be adjusted by either releasing or introducing fluid through the interior outlet 19' in interaction with the connector 51 such that the contact point surface 83 and the transition section 85 are at the same height H indicated by the dashed line in FIG. 14. Based on the experience of the inventor of the present invention, once this happens, the optimum pressure conditions for manufacturing the plaster impression are available.

Even if the connector is not adjustable in length, it advantageously ensures that a predetermined extent of floating 81 cannot occur. A predetermined extent may be 1 to 4 cm, more preferably about 2 cm.

FIG. 15 shows an apparatus 100 according to the present invention in a thirteenth embodiment. It comprises a first pressure sensor 91 (or a plurality of sensors of this type), shown on the left side in FIG. 15, which sensor is located in the fluid of the pressure chamber DK and is optionally connected to the wall 3. The at least one pressure sensor 91 is arranged, configured and/or integrated in order to measure a pressure which prevails in the pressure chamber DK. The pressure sensor 91 may be wirelessly or in a wired manner connected to, or in signal communication with, the apparatus 100 or with one of its units or arrangements.

Alternatively or additionally, a pressure sensor 91, which is shown on the right in FIG. 15, may be provided to be arranged at or in the membrane 5 or on a section of the surface of the limb stump KS covered by the membrane 5 during use of the apparatus 100 and/or is arranged between the membrane 5 and the limb stump KS and measures the pressure prevailing there.

Optionally, the medical apparatus 100 comprises or is connected to a display device 93. The latter is configured to receive and display a signal corresponding to a pressure signal from a pressure measuring device such as the above-mentioned pressure sensor 91 or from an evaluating device 95. A connection between the pressure sensor 91 and the display device 93 is indicated by a dashed line respectively. The connection can be wired or wireless.

Optionally, the medical apparatus 100 comprises or is connected to a detection device 97. The latter is configured, for example, by using a pressure value determined by a pressure measuring device such as the at least one pressure sensor 91 or based thereon, to determine the weight with which the patient must be weighed so that the pressure in the pressure chamber DK (which in turn can be measured by means of the pressure measuring device such as the pressure sensor 91) is in a predetermined target value range for the pressure, or moves into this range, when the limb stump KS is inserted into the medical apparatus 100.

In this, the medical apparatus 100 may optionally comprise a display device 99 configured to display the weight with which the patient whose limb stump KS is inserted into the medical apparatus 100 must be weighted so that the pressure in the pressure chamber DK is in a predetermined target range.

The display device 99 may be realized or embodied together with the display device 93; however separate display devices may also be provided, for the purposes mentioned supra.

The display device 99 may be connected directly or indirectly to the pressure sensor(s) 91, as indicated in FIG. 15.

FIG. 16 shows a calculation device 200 according to the present invention in an exemplary first embodiment. This can be part of the apparatus 100 according to the present invention or connected physically or in a signal communication thereto. It may however also be independent of the apparatus 100.

The calculation device 200 comprises an input device 201 (for example, a keyboard, a scanner, a mouse, an interface, a stick, a memory unit, an interface (Bluetooth or the like) etc.) and an output device 203 (for example, a monitor, a display, a printer, a memory unit an interface (Bluetooth or the like) etc.).

The calculation device 200 is configured to determine, using patient-related data which can be entered via the input device 201, the weight with which the patient must be weighted with when using an apparatus for manufacturing a plaster impression, for example the one described herein, with a membrane 5 and a pressure chamber DK. This allows to advantageously achieve a determined or specified load of the membrane 5 in advance. The load determined in advance may be a pressure which is within a predetermined target range as described herein.

The calculation device 200 is here optionally configured to access stored algorithms. Alternatively or additionally, the calculation device 200 may be configured to access reference data or values 205, which are stored, for example, in a look-up table.

FIG. 17 shows an apparatus 100 according to the present invention in a fourteenth embodiment with a multi-part wall. The multi-part wall comprises three cylindrical wall sections 101, which can be inserted into each other. The uppermost wall section 101 comprises the largest diameter, the middle wall section 101 comprises a smaller diameter and the lower wall section 101 comprises an even smaller diameter. Due to this gradation, the middle wall section 101 can be inserted into the upper wall section 101 and the lower wall section 101 can be inserted into the middle wall section 101. Other constellations are likewise possible, for example, the middle wall section 101 may comprise the smallest diameter.

Guide pins 105 and oblong holes 107 are provided in this exemplary embodiment as guide aids for pushing together the cylindrical wall sections 101. The uppermost and the middle wall sections 101 comprise each at least one oblong hole 107 on its circumference into which guide pins 105, which are arranged on the middle and lower wall section 101, can be inserted.

The number of wall sections 101 is of course not thereby limited to three. More or less wall sections 101 may be provided.

Furthermore, locking devices may be arranged for the releasable fixing of the wall sections 101, not shown in FIG. 17, which are displaceable relative to each other. A securing pin may, for example, be inserted into openings or bores provided for this purpose (not shown in FIG. 17), wherein the openings may be arranged, for example, perpendicular to the direction of movement of the displaceable wall sections 101 and in these wall sections 101. Further, a locking device may comprise the guide pin 105. For example, the guide pin 105 may be arranged to be rotatable or tiltable, and it may be inserted plugged in oblong holes arranged at a predetermined angle relative to the movement direction of the displaceable wall sections 101. The angle may, for example, be arranged perpendicular relative to the movement direction of the displaceable wall sections 101. A locking of the wall sections 101 may take place in a partially or completely extended state (as shown in FIG. 17) so that an unwanted collapsing or pushing-together of the wall sections 101 can be prevented. However, a locking of the wall sections 101 can also take place in the collapsed state (as shown in FIG. 18) or in the partially collapsed state.

In the embodiment of FIG. 17, the three wall sections 101 are of the same length in the longitudinal direction L. In other embodiments, the lengths may be different from each other.

Further, the embodiment of FIG. 17 comprises a tubing section 103, which is designed as a fluid-tight, in particular water-tight membrane or film. The tubing section 103 seals the fluid F of the pressure chamber DK against the wall sections 101. In this exemplary embodiment, the tubing section 103 is fastened purely by way of example to the upper edge 7 of the uppermost wall section 101 of the apparatus 100 according to the present invention and to the bottom area 4a of the lowest wall section 101. Likewise, the tubing section 103 can be fastened, for example, with its upper end to the inner side of the upper wall section 101 and/or with its lower end to the inner side of the lower wall section 101. Other positions for fastening are also possible.

Fastening may for example be executed by a mechanical fastening, e.g. clamping, by a material fastening, e.g. adhesion, or in another manner.

The outlet 19' in the lower wall section 101 is connected to the pressure chamber DK. Compared to the previous embodiments, the outlet 19', thus, not only reaches through the side wall of the wall section 101 but rather extends through the wall, membrane or film of the tubing section 103 into the pressure chamber DK so that a fluid exchange between the exterior and the pressure chamber DK can be carried out.

The outlet 19' may, for example, be connected to the tubing section 103 by means of material bond or adhesion and thus establish a fluid connection between the interior I and the exterior of the apparatus 100. Notwithstanding its designation as an outlet, this can also be used for the admission or introduction of fluid and thus for the filling of the pressure chamber DK.

The remaining construction substantially corresponds to the apparatus 100 according to the present invention of the embodiment shown in FIG. 3, so that reference is made to this description.

The tubing section 103 does not contact the wall sections 101 in FIG. 17. This illustration is for the sake of clarity only. In practice, the fluid pressure of the fluid in the interior I of the apparatus 100 forces the tubing section 101 radially outwardly against the wall sections 101.

It should also be noted that the tubing section 103 is purely optional. It serves to seal between the adjacent wall sections 101. Should it be unnecessary to seal the latter, then the tubing section 103 is not needed. Likewise, instead of the tubing section 103 or in addition to it, any other sealing device may also be provided, for example labyrinth seals, rubber seals, frictional seals or the like.

FIG. 18 shows the apparatus of FIG. 17 according to the present invention in a fully collapsed transport state. Compared to FIG. 17, the fluid F has been emptied from the pressure chamber DK through the outlet 19' and the three wall sections 101 are pushed into one another. The total length L in the collapsed transport state shown in FIG. 18 corresponds approximately to one third of the length shown in FIG. 17 in the fully extended state. The first membrane 5 and the tubing section 103 are collapsed or partially folded.

In the collapsed state, the guide pins 105 are inserted into the oblong holes 107.

By way of example, the total length in the extended state (FIG. 17) could be approximately 50 cm, and in the collapsed state approximately 20 cm.

In an exemplary embodiment according to the present invention, a disengagement from the transport state (FIG. 17) into the extended state or application or use state of FIG. 16 may take place by filling the fluid F into the pressure chamber DK through the inlet 19'. The fluid introduced under pressure widens the space of the pressure chamber DK, with the wall sections 101 increasingly switching from the state shown in FIG. 18 to the state shown in FIG. 17. By means of the ducts of the guide pins 105 in the oblong holes 107, the wall sections 101 can be simply and securely pushed into each other and pulled apart. A tilting or jamming of the wall sections 101 resulting from a movement, which is not straight in the longitudinal direction L, of the wall sections 101 can be advantageously prevented.

FIG. 19 shows an apparatus 100 according to the present invention in a fifteenth embodiment with an outwardly curved bottom area 4a. This form of the bottom area 4a may be referred to as a convex form.

The outwardly curved bottom area 4a makes it possible, preferably during the production of a plaster impression or a data model of the limb stump KS, to roll or move the medical apparatus. Thus, not only a static load, as it occurs without moving the apparatus, but also a dynamic load can be generated or readjusted in the plaster impression. Dynamic load allows, during the making of a plaster impression, to incorporate or simulate a muscular and/or bony displacement which occurs during walking.

The outwardly curved bottom area 4a is exemplarily shown in FIG. 19 as a hemispherical calotte in a sectional view. The bottom area 4a can alternatively have other forms, e.g. (partly) cylindrical paraboloid or other curved forms.

The wall 3 is shown in one-piece, but can also be configured in multiple piece, as shown in FIG. 17 and in FIG. 18. Likewise, the exemplary embodiment may have a tubing section 103, or one or all other features of the exemplary embodiments discussed supra.

FIG. 20 shows an apparatus 100 according to the present invention in a sixteenth embodiment with an inwardly curved bottom area 4a. The discussion and explanations of the embodiment of FIG. 19 (convex form of the bottom area 4a) apply analogously to the embodiment with the inwardly curved bottom area 4a, which can be designated as a concave form of the bottom area 4a.

A convexly formed bottom area 4a preferably requires a special form of a bearing or support surface on which the apparatus can move, for example, in a tiltable, rotatable, or displaceable manner relative to the support surface. For example, a spherical concave-formed bottom area 4a with a smaller radius, compared to the radius of the concave-formed bottom area 4a, would be a preferred form of a contact surface.

FIG. 21 shows an apparatus 100 according to the present invention in a seventeenth embodiment with a spherical or cylindrical lug 109 in or on the bottom area 4a. The lug 109 is designed as a one-piece component or as an integral component of the bottom area 4a. The lug 109 may, for example, be moved on a flat or curved base such that the apparatus can be tilted, rotated or displaced against the base and a dynamic loading of the plaster impression, as described in FIG. 19, is enabled.

FIG. 22 shows a system 300 according to the present invention with a medical apparatus 100 according to the present invention and a contact surface 111. The contact surface 111 illustrated in section may have a three-dimensional form of a paraboloid, a roller or another form. The apparatus 100 can be moved on the contact surface 111 so that it may be tiltable, rotatable or displaceable relative to the contact surface 111, and thus generating a dynamic load as described in FIG. 19.

The contact surface 111 and a body connected thereto may be a part or section of a floor or underground. Likewise, the body of the contact surface 111 can be arranged on an underground or can be connected thereto, releasably or non-releasably, FIG. 23 shows a further system 300 according to the present invention with a contact surface 111 designed as an ellipsoid. The ellipsoid is arranged on an underground 113. Preferably, the ellipsoid is fixed to or on the underground 113 so that, upon movement of the apparatus 100 on the contact surface 111, the ellipsoid does not move or displace itself.

FIG. 24 shows a further system 300 according to the present invention with a contact surface 111 designed as a ball.

FIG. 25 shows a system 300 according to the present invention with a contact surface 111 connected to the bottom area 4a of the apparatus 100. The connection may be, for example, a material connection, e.g. adhesive, or form-fit connection, e.g. by hinges. The connection may be a screwed connection or other connection.

The system 300 according to the present invention is arranged, for example, on an underground 113. The system 300 according to the present invention may be moved on the underground 113, for example it may be tilted, rotated or displaced.

FIG. 26 shows a system 300 according to the present invention with a securing collar 115 designed as tube.

The securing collar 115 is connected to the upper end of the apparatus 100 according to the present invention, for example by a collar, an adhesive or some other type of fastening. The securing collar 115 encloses a part of the limb stump KS protruding upwards out of the insertion opening 9. In particular, this enclosing prevents the limb stump KS from accidently slipping out of the pressure chamber DK due to a tilting, rotational, displacement movement or a mixed superimposed movement of the mentioned types of movements of the apparatus 100 on the contact surface 111.

Securing the limb stump KS against an unwanted slipping out of the pressure chamber DK may additionally be improved by applying a vacuum in the space between the securing collar 115 and the limb stump KS. For this purpose, the material of the securing collar 115, the connection of the securing collar 115 to the apparatus 100 and all other connection points are preferably designed to be pressure-tight and/or fluid-tight.

FIG. 27 shows an apparatus 100 according to the present invention in an eighteenth embodiment with an upwardly open hollow vessel 117, which is a release unit for relieving pressure of the distal region of the limb stump KS. The hollow vessel 117 comprises a cup-like form. The pressure relief is achieved by the cavity between the distal end of the limb stump KS and the bottom of the hollow vessel 117. This cavity relieves the delicate soft tissues at the distal end of the limb stump KS, by not causing any pressure load by the fluid F, which is felt as unpleasant by some patients.

The hollow vessel 117 is inserted or pushed into the insertion opening 9 and into the membrane 5 before the introduction of the limb stump KS. The hollow vessel 117 can then be positioned in the lower region of the pressure vessel 1, e.g. in the immediate vicinity of the connector 53. Subsequently, the limb stump KS can be introduced into the pressure vessel 1. The hollow vessel 117 may however be pushed into the depth of the membrane 5 by the limb stump KS itself.

FIG. 28 shows an apparatus 100 according to the present invention with a further release unit. The release unit is filled as a hollow vessel 117 with a preferably soft and compressible material 119. The hollow vessel 17 is purely optionally closed from the top by a top coating 121 which may be a membrane. The material 119 may comprise open or closed pores, and may for example be a foam material.

In FIG. 28, the limb stump KS does not touch the upper edge of the release unit, it rests on the material 119. However, this is to be understood as purely exemplary. The edge may also be used for support in the embodiment shown in FIG. 28.

FIG. 29 shows an apparatus 100 according to the present invention in a twentieth embodiment with an adapter 207 for fixing the limb stump KS in the pressure vessel 1.

In the example of FIG. 29, the adapter 207 comprises a release unit, designed as a hollow vessel 117, an adherent stocking 215, a belt 209, a fastening ring 213 and a diverting or deflecting ring 211. The belt 209 may also be a rope or other suitable means for pulling or holding. The adapter 207 could additionally comprise a unit 223 for fixing and/or adjusting the belt 209.

The belt 209 is fixed at its one end to the hollow vessel 117 by the fastening ring 213. The hollow vessel 117 is connected to the adherent stocking 215 (which is referred to herein as a so-called liner). The adherent stocking 215 may be fastened, e.g., to the upper edge of the hollow vessel 117, e.g. by an adhesive or a mechanical fixation, or may surround the entire hollow vessel 117 on its outer and/or inner side (not shown in FIG. 29). The adherent stocking 215 is put over or pulled over the limb stump KS (or its distal end).

It is preferred that the limb stump KS cannot slip out of the adherent stocking 215 with or without the hollow vessel 117.

In the embodiment shown in FIG. 29, the hollow vessel 117, together with the adherent stocking 215, is a part of the adapter 207. In other embodiments of the adapter 207, the latter may comprise further components, such as the belt 209 and/or the fastening ring 213. In other embodiments of the adapter 207 however, the latter does not comprise a hollow vessel 117 rather, e.g., only the adherent stocking 215 and, e.g., a fastening ring 213 attached thereto, with without the belt 209.

The belt 209 is guided further outwards via the diverting ring 211, which is exemplarily arranged herein within the pressure vessel 1. The diverting ring 211 is connected to the bottom of the pressure vessel 1 by a common connector 217. The common connector 217 concurrently fixes the membrane 5 to the bottom of the pressure vessel 1.

The common connector 217 may be different in length.

Depending on the selected length of the connector 217, the limb stump KS can be differently-deep positioned in the pressure vessel 1 near the bottom area 4a. The common connector 217 may also be adjustable in its length, e.g., in different steps, which may be fixed and adjusted at the bottom area 4a.

The membrane 5 in FIG. 29 has a bag shape. Likewise, the membrane 5 could have a different shape, e.g. a tube shape. For creating or manufacturing a plaster impression, the limb stump KS, which is inserted in the adapter 207, i.e., in the adherent stocking 215 with the hollow vessel 117, is introduced into the pressure vessel 1 together with the adapter 207. At the same time, the belt 209 is introduced, wherein usually it is not actively pulled.

After the limb stump KS (together with the hollow vessel 117 and the adherent stocking 215) is placed at the desired depth in the pressure vessel 1 (shown in FIG. 30), the limb stump KS may be fixed or held in the pressure vessel 1 by the pulling device 209 during the building up of pressure in the pressure chamber DK and during the hardening of the plaster impression. This may be done, e.g., by manually fixing the outer end of the belt 209. The limb stump KS is advantageously prevented, by means of the adapter 207, from being moved, against the inlet direction or the longitudinal direction L (see FIG. 8), due to the forces exerted on it by the membrane 5 as well as due to floating caused by the fluid.

By means of the adapter 207, the limb stump KS may advantageously be held or fixed in the pressure vessel 1 during the preparation (or curing) of the plaster impression without the patient himself/herself having to continuously exert any active pressure on the limb stump KS. The limb stump KS is held in the pressure vessel also at a higher pressure prevailing in the pressure chamber DK. It cannot axially escape the pressure required for creating a suitable plaster impression.

FIG. 30 shows the arrangement of FIG. 29 in the fixed state of the limb stump KS in the pressure vessel 1.

FIG. 31 shows the apparatus 100 according to the present invention with the pressure vessel 1 and a tubular membrane 5. The tubular membrane 5 is fixed to the bottom area 4a of the pressure vessel 1 by an optional intermediate piece 219.

FIG. 32 shows the apparatus 100 according to the present invention with the pressure vessel 1 and a further tubular membrane 5. The tubular membrane 5 is fixed or fastened to the outer edge of the bottom area 4a of the pressure vessel 1. The connector 217 in this embodiment is fastened to the bottom area 4a without an intermediate piece 219 (see FIG. 31).

FIG. 33 shows the apparatus 100 according to the present invention with at least one sensor 221; in this exemplary embodiment with two sensors 221. The at least one sensor 221 can be connected to the adapter 207 and/or to the membrane 5. In particular, the sensor 221 is integrated into the adherent stocking 215 and/or into the membrane 5, for example, in an interspace of a double-walled design of the adherent stocking 215 and/or of the membrane 5.

The position and application of the sensor 221 is expressly not limited to the embodiment of FIG. 33, but can be applied or used in any other described embodiment.

The sensor 221 may be a sensor 221 for detecting physiological data of the limb stump KS. For example, in an oximetry with an oximeter as sensor 221, the oxygen content of the blood may be determined for checking the vascular blood flow or perfusion in the limb stump KS. Examining the vascular blood flow in the limb stump KS may also be carried out with other sensor measuring methods, for example using the Doppler principle as a measuring method or the ultrasonic principle.

FIG. 34 shows the apparatus 100 according to the present invention with a unit 223 for fixing and/or adjusting the adapter 207. The pulling device of the adapter 207 may the belt 209.

By means of the unit 223, the belt 209 can be fixed, e.g., when the limb stump KS is to be fixed in the pressure vessel (see FIG. 30). Likewise, the belt 209 may be moved for example, in particular controlled manner, by a unit 223, for example by a step-shaped movement. Such a unit may be referred to as a so-called "ratchet".

FIG. 35 shows a detail of the apparatus 100 according to the present invention with a further unit 223 for fixing and/or adjusting the adapter 207. In this exemplary embodiment, the belt 209 is guided outwards to the unit 223 via a diverting ring 211 being arranged below the bottom area 4a of the pressure vessel 1. The belt arrangement and the diversion by means of the diverting ring 211 may thus advantageously be positioned outside the membrane 5 and the liquid F.

FIG. 36 shows a set according to the present invention with an adherent stocking 215 according to the present invention and an apparatus 100. The adherent stocking 215 has been pulled over or worn over the limb stump KS prior to introducing the limb stump KS into the pressure vessel 1. In the arrangement of FIG. 36, the adherent stocking 215 is frictionally connected to the membrane 5 on its outer side, e.g. by a roughened, structured, coated and/or treated surface. The membrane 5 is fixed in the pressure vessel 1 by the connector 53. By means of this arrangement, the limb stump KS cannot slide out of the pressure vessel 1 without additional force, or cannot unintentionally move out of it. In this, a plaster impression or a data model of a limb stump, in particular of a lower leg, can advantageously be manufactured without the patient causing unforeseen or unintended movements with the limb stump KS during the plaster impression or during the production of a data model. Such movements may adversely affect the production of the plaster impression or the data model.

FIG. 37 shows a unit 400 according to the present invention with a medical apparatus 100 according to the present invention and a pressurization control device 410 according to the present invention. The pressurization control device 410 is hereinafter abbreviated as the control device 410.

The control device 410 comprises a pressure reservoir connection or port 413, which can be designed as a connection to a pressure source, e.g. to a water line. Furthermore, in the embodiment shown here, the control device 410 comprises a separate outflow connection 415 for emptying the fluid from the pressure chamber DK. The outflow could alternatively take place, e.g., by means of a multi-way valve, which can be connected to the pressure reservoir connection 413.

The control device 410 of FIG. 37 further comprises an optional pressure-control valve disposed within the control device 401 (not shown in FIG. 37). The pressure-control valve may limit the pressure prevailing in the pressure reservoir connection 413, so that the pressure applied downstream of the pressure-limiting valve does not exceed a pre-determinable or an optionally user-adjustable value. As a result, an excessively high pressure in the pressure chamber DK may advantageously be avoided or prevented, which, for example, might cause an excessive pressure load on the limb stump KS, and thus could cause damage and pain, as well as a distortion of the plaster impression. The pressure-control valve may purely exemplarily limit the pressure to max. 0.8 bar.

The control device 410 further comprises a pressure chamber connection 417, which is connected to, or comprises, a regulating valve 419 for increasing pressure in the pressure chamber DK. When the control valve 419 is actuated, e.g. manually, it can increase the pressure in the pressure chamber DK, e.g. gradually, up to a desired pressure or to the maximum pressure which is limited by the pressure-control valve.

Furthermore, the control device 410 comprises a pressure chamber backflow connection 421, which is connected to, or comprises a further regulating valve 423 for reducing pressure in the pressure chamber DK. When the further control valve 423 is actuated, e.g. manually, it can reduce the pressure in the pressure chamber DK, e.g. gradually, as required. Once the plaster impression has been completed, the pressure in the pressure chamber DK can be reduced to the point where the patient may pull the limb stump KS out of the apparatus 100.

In the illustrated embodiment, the control device 410 further comprises an optional inlet-pressure display 425 and a likewise optional emergency shut-down device 427. The inlet-pressure display 425 may be referred to as a manometer and may be provided as an additional display, for example as a safety display or redundancy arrangement for monitoring the pressure in the pressure chamber DK. The inlet-pressure display 425 is arranged, e.g., with, or in, a connection line in the control device 410 between the regulating valve 419 (for the pressure increase in the pressure chamber DK) and the pressure chamber connection 417.

Emptying the pressure chamber DK by the pressure chamber backflow connection 421 and the outlet connection 415, controlled by the further regulating valve 423, may be effected in various ways. For example, a suction pump can be sucked in, for example, downstream of the outlet connection 415, which, when the further regulating valve 423 is opened, sucks fluid F from the pressure chamber DK and, if necessary, until empty. Likewise, a venturi nozzle or a venturi tube for sucking or draining the fluid F from the pressure chamber DK may be connected, for example, downstream of the outlet connection 415. A venturi nozzle may, for example, be connected to an external water connection, for example, to a water tap on a wash basin. If the water tap is opened and water flows through the venturi nozzle, a vacuum is generated in a line connected to the outlet connection 415, and fluid F, with the further regulating valve 423 being opened, is sucked. A venturi nozzle advantageously does not require any electrical connection, as would for example be necessary for a suction pump.

The exemplary embodiment of the control device 410 described here, advantageously does not require any electrical components and thus no power supply and no power connection.

In embodiments of the invention other than those described herein, the pressurization control device is, or comprises, a device for applying pressure to a fluid reservoir such as the reservoir 21 of FIG. 5.

For this purpose, it is contemplated to provide, e.g., a mechanical or hydraulic pressing device by means of which the fluid may be discharged from the reservoir 21 or from the pressurization control device under a desired pressure or in any case a sufficient pressure.

Such a mechanism may include a crank mechanism, a pressing or clamping mechanism having clamping surfaces, a foot actuating device the construction of which is similar to a pair of bellows or to a bicycle pump or the like. By means of such a pressurization control device, one the one hand, the required pressure may be achieved, on the other hand, the user of the apparatus according to the present invention is not dependent on external pressure sources, such as water connections or the like.

The pressurization control device can be operated electrically. However, this is not required. It can be provided to operate without power supply.

FIG. 38 shows a medical apparatus 100 according to the present invention with a form body 127 for receiving the distal region of the limb stump KS, as well as a composite stocking 123, characterized in the partial enlargement Z.

The composite stocking 123 is pulled over or worn over the limb stump KS and directly contacts the skin of the limb stump KS. The plaster bandage 125 is wrapped over the composite stocking 123 on the outside. Optionally, in an intermediate step, a thin plastic film maybe applied over the composite stocking 123, in particular to protect the composite stocking 123 from the damp plaster of the plaster bandage 125 and to avoid additional subsequent cleaning steps. The composite stocking 123 comprises a smooth or smoother surface on its inner side oriented toward the limb stump KS and comprises a rough or rougher and/or structured or a more structured surface on its outer side oriented toward the plaster bandage 125. The smooth inner side is intended to produce a frictional adhesion or connection to the limb stump KS, in order to secure a slipping of the limb stump KS, in particular when applying pressure during the plaster impression in the apparatus 100 and a pressure increase in the pressure chamber DK up to the maximum pressure, which is limited by the pressure-control valve. The rough and/or structured surface of the composite stocking 123 is intended to secure a good and force-fit connection and/or form-fit connection as possible to the plaster bandage 125. The plaster bandage 125 is moist and formable when placed on the limb stump KS so that the inner side of the plaster impression is fitted to the rough and structured form and may become part of the dried plaster impression.

The form body 127 comprises a hard and a dimensionally stable shell, the outer side of which is preferably smooth. The outer side is intended to secure and ensure a high adhesion friction of the form body 127 on the membrane 5 in the assembled state. Hence, it is advantageously intended to enable the form body 127 and thus the limb stump KS arranged in the form body 127 to be pushed out or moved out when applying pressure during the production of the plaster impression in the apparatus 100 and a pressure increase in the pressure chamber DK up to the maximum pressure, which is limited by the pressure-control valve.

A compressible, preferably soft, material 119 is arranged in the form body 127. The material 119 may, for example, be foam. This material 119 may advantageously protect the distal region of the limb stump KS and release pressure therefrom, particularly in the case of a pressure increase in the pressure chamber DK up to the maximum pressure.

The Form body 127 may, for example, be made of, or comprise, a thermoplastic. Thermoplastics are, for example, acrylonitrile butadiene styrene (ABS), polyamide (PA), polylactate (PLA), polymethyl methacrylate (PMMA), Polycarbonate (PC), polyethylene terephthalate (PET), polyethylene (PE), polypropylene (PP), polystyrene (PS), polyetheretherketone (PEEK) or polyvinylchloride (PVC). Likewise, the form body 127 may be made of, or comprise, a different material, for example, a fiber-reinforced composite material.

The dashed arrows of FIG. 40 show the direction of the limb stump KS and the form body 127 when being inserted or introduced into the apparatus 100.

FIG. 39 shows the arrangement of FIG. 38 in the assembled state. The distal end of the limb stump KS is inserted or pushed or introduced into the compressible material of the form body 127. Due to the pressure in the pressure chamber DK, the membrane 5 bulges or cambers above the insertion opening 9 (see FIG. 38).

FIG. 40 shows an apparatus 100 according to the present invention with a multi-part form body 129 for receiving the distal region of the limb stump KS.

By means of the multi-part and module-form form body 129, different lengths of the limb stump KS can be compensated or adapted. The basic structure and the material selection is analogous to the form body 127, which has been described in detail in FIG. 39. For example, the individual modules of the form body 129 comprise smooth surfaces on the outer side in order to achieve high static or adhesion friction on the membrane 5.

The compressible material 119 has the same function as already described in FIG. 39. The volume of the material 119 can be adapted according to the final size and height of the modular form body 129. When the material 119 is possibly a foam material, then the volume may be adapted by trimming.

Analogous to FIG. 38, the limb stump KS may be enwrapped by a composite stocking 123 and its characteristics described above and a plaster bandage 125. For the sake of simplicity, only one wrap is shown in FIG. 40.

The dashed arrows indicate the direction of the limb stump KS, of the material 119 and of the multi-part form body 129 upon inserting or introducing into the apparatus 100.

FIGS. 40a-c show the different sizes of a compressible material 119 and associated shells 120 for receiving the distal region of the limb stump KS. The compressible material 119, for example foam, may be prepared or adapted or pre-fabricated, for example by means of trimming. Pre-fabricated materials 119 may be referred to as ready-for-use materials 119.

The shells may be stacked one inside the other as shown in FIGS. 40a, 40b and 40c. Depending on the size of the innermost shell 120, a correspondingly large compressible material 119 may be inserted.

Shells 120 having different sizes and the material 119, which is inserted according to the size, may advantageously be used for differently sized distal end dimensions of the limb stump KS. The compression pressure may thus be adapted to pressure-sensitive, distal regions of the limb stump KS.

The shells 120 may be adapted to the multi-part form body 129 in a module manner and combined.

FIGS. 40d-g show different lengths of a multi-part form body 129 for the length compensation of differently long limb stumps KS. The lowermost module is formed like a dome to be inserted into the membrane 5. The form bodies 129 adjoining the latter in a module-form manner may be adapted according to the length of the limb stump KS. The individual form bodies 129, which are modularly connected, may be denoted as discs or disc-shaped. They may be adapted to each other with tight-fits.

FIG. 41 shows an exemplary embodiment of a schematic arrangement of components within the pressurization control device 410.

In addition to the description of FIG. 37, only additional components or functions are described below.

In the following, an incoming fluid at port 413 is described as water, but without being limited to water as a fluid.

The incoming water may initially enter or flow in the optional pressure-control valve 414. The pressure-control valve 414 may limit or reduce the water pressure at the port 413. Purely exemplarily, the water pressure at the port 413 may be 8 bar or 10 bar and may be reduced to, for example, 2 bar or 1 bar by the pressure-control valve 414.

Downstream of the pressure-control valve 414, the water flows via a line into (or passes through) a first regulating valve 419 with which the line may be, e.g., opened and (in particular completely or partially) closed as required. Thus, the supply of water into the pressure chamber DK (not shown) of the apparatus 100 or the filling of the apparatus 100 may be controlled. The control may for example be manually effected by actuating the regulating valve 419.

Further downstream, an inlet pressure display 425 is optionally arranged. When the regulating valve 419 is open, the water pressure is displayed downstream of the pressure-control valve 414. When the regulating valve 419 is closed, the pressure in the pressure chamber DK of the pressure vessel 1 is displayed. Further downstream, the water flows via the pressure chamber connection 417 to the pressure chamber DK (not shown).

A further regulating valve 423 likewise regulates the passage between the pressure chamber backflow connection 421 returning from the pressure chamber DK and the outlet connection 415.

An optional line branch leading to an emergency shut-down device 427 is illustrated upstream the pressure-control valve 414; further downstream (lower branch at the emergency shut-down device 427), a line branch leading to an also optional venturi nozzle 429 is illustrated. The emergency shut-down device 427 is usually always open, unless it is actuated and closed in an emergency. Further downstream, outgoing from the venturi nozzle 429, the water continues to flow to the outlet connection 415. A vacuum is generated inside or by means of the venturi nozzle 429 (e.g. by means of a Laval nozzle). A further line for sucking off water from the pressure chamber DK is connected to this vacuum. This connection first branches off upstream of the further regulating valve 423 and leads to a vacuum display 431, e.g. a manometer. At the outlet of the vacuum display 431, this line further leads, optionally via the emergency shut-down device 427, to the venturi nozzle 429 at the previously described vacuum connection.

The venturi nozzle 429 with the described connecting lines can be switched (off) or switched on as required in order to empty the pressure chamber DK. This is realized, for example, by means of optional shut-off valves or the like which, however, are not shown in FIG. 41 for the sake of clarity.

By means of the venturi nozzle 429, the pressure chamber DK may advantageously be emptied without, advantageously, having to connect the pressurization control device 410 to a source for electric current/electric voltage.

The pressurization control device 410 of FIG. 41, as well as of other embodiments of the present invention, comprises no (electric) current connection.

LIST OF REFERENCE NUMERALS

100 apparatus
1 pressure vessel
2 first end side
3 wall
4 second end side, may optionally be closed or sealed with the bottom area
4a bottom area
5 membrane
7 upper rim or edge
9 insertion opening
11 clamping ring
13 limiting ring or thigh sealing ring
15 leg opening
17 screws
19, 19' outlet, inlet
21 reservoir
23 feet or support device
25 cover
27 level of the fluid/fluid level
29 inlet
31 pressure line
33 Pressure source
35 compensating line, fluid communication
37 clamp
39 contact surface or underground or base
41 roller arrangement
43 support
45 handle
47 air release opening
51 lower section of the wall
53 connector
55 longitudinal fiber
55a longitudinal fiber
55b longitudinal fiber circumferential fiber or cross fiber
57a circumferential fiber or cross fiber
57b circumferential fiber or cross fiber
58 central or middle area or section of the membrane
61 lower section of the membrane
63 shell
65 threads
67 socket
71 camera as an example of a device for measuring, scanning or detecting
73 device for preparing or calculating a model of the limb stump or of the stem intended to be produced for the limb stump
75 shaping device
81 uplifting or floating of the membrane
83 contact point surface
85 transition section
91 pressure sensor
93 display device
95 evaluation device
97 detection device
99 display device
101 wall section
103 tubing section
105 guide pin
107 oblong hole
109 spherical lug
111 contact surface
113 Underground
115 securing collar
117 hollow vessel
119 material
120 shell
121 top coating
123 composite stocking
125 plaster bandage
127 form body
129 multi-part form body
200 calculation device
201 input device
203 output device
205 reference data
207 adapter
209 belt
211 diverting or deflecting ring
213 fastening ring
215 adherent stocking
217 common connector
219 intermediate piece
221 sensor
223 unit for fixing and/or adjusting
300 system with device/contact surface/securing collar
400 unit
410 pressurization control device
413 pressure reservoir connection or port
414 pressure control valve
415 outlet connection
417 pressure chamber connection
419 regulating valve
421 pressure chamber backflow connection
423 further regulating valve
425 inlet-pressure display
427 emergency shut-down device
429 venturi nozzle
431 negative-pressure display
DK pressure chamber of the pressure vessel
I pressure vessel interior
II reservoir interior
F fluid or liquid
Ä pressure vessel exterior
ÄÄ reservoir exterior
KS limb stump
L longitudinal direction
Q cross direction

The invention claimed is:

1. A medical apparatus (100) for use in the preparation of a plaster impression or a data model of a limb stump, wherein the apparatus (100) comprises:
   a pressure vessel (1) with a fluid chamber or a pressure chamber (DK) for receiving or storing a fluid under pressure, wherein the pressure vessel (1) comprises a wall (3) made of a first material, wherein the wall (3) limits an interior (I) of the pressure vessel (1) against an exterior (Ä), wherein the pressure vessel (1) comprises an insertion opening (9) in a first end side (2) of the pressure vessel (1) for inserting the limb stump (KS) into the interior (I) of the pressure vessel (1); and
   a fluid-impermeable membrane (5) made of a second material, which membrane (5) is connected to the pressure vessel (1) at a side of the insertion opening (9) at the first end side (2) arranged to form or limit the fluid chamber or the pressure chamber (DK), wherein at least a section (58) of the membrane (5) is fastened to a bottom area (4a) or to a second end side (4) of the pressure vessel (1) opposite the first end side (2) by at least one connector (53).

2. The medical apparatus (100) as in claim 1, with:
   an outlet (19, 19') which is a fluid communication between the fluid chamber or the pressure chamber (DK) and the exterior (Ä) of the pressure vessel (1); and
   a valve, a stop or lock device or a stopcock for opening or closing the outlet (19, 19') or the fluid communication.

3. The medical apparatus (100) as in claim 2, wherein the outlet (19, 19') of the pressure vessel (1) is arranged in the area of the second end side (4) or in an area of an end side of the pressure vessel (1), and in particular in its wall (3).

4. The medical apparatus (100) as in claim 1 which further comprises or is connected to:
   a fluid source or a reservoir (21) having an interior (II) and an exterior (ÄÄ); and
   a fluid connection (35) by means of which the interior (II) of the reservoir (21) or the fluid source on the one hand and the outlet (19, 19') on the other hand are in contact and/or in fluid communication with each other, respectively.

5. The medical apparatus (100) as in claim 1, wherein at least a section (58) of the membrane (5) is fastened to a section of the wall (3) by at least one connector (53).

6. The medical apparatus (100) as in claim 5, wherein the connector (53) is not elastic and/or is not stretchable.

7. The medical apparatus (100) as in claim 5, wherein the connector (53), the membrane (5) and/or the bottom area (4a) comprises at least a thread (65) for directly or indirectly screwing the membrane (5), or an element connected thereto, to the pressure vessel (1).

8. The medical apparatus (100) as in claim 1, wherein the at least a section (58) of the membrane (5) is a central or middle section (58) of the membrane (5) is releasably fastened to a middle or central section of the bottom area (4a) or to the second end side (4) of the pressure vessel (1) by the at least one connector (53).

9. The medical apparatus (100) as in claim 1, wherein the membrane (5) is made of or comprises a material which comprises another elasticity or extendibility in a first direction of the material than in a second direction being perpendicular to the first direction.

10. The medical apparatus (100) as in claim 1, wherein the membrane (5) is made of or comprises a material which comprises, in a first direction and/or in a second direction of the material, fibers (55a, 57a, 55b, 57b) which are embedded in a matrix or connected thereto in a different way.

11. The medical apparatus (100) as in claim 1, wherein the membrane (5) is not extendable or is not elastic in a first direction (L) thereof and/or in a second direction (Q) thereof.

12. The medical apparatus (100) as in claim 1 which comprises a release unit for releasing pressure from a distal section of the limb stump (KS), wherein the release unit is arranged, or is configured to be arranged on the membrane (5), outside the pressure chamber (DK) and/or within a space formed by the membrane (5).

13. The medical apparatus (100) as in claim 12, wherein the release unit is a hollow vessel (117) with at least an opening or recess, wherein the opening or recess is directed towards the distal section of the limb stump (KS) or is determined for this purpose.

14. The medical apparatus (100) as in claim 13, wherein the opening or recess comprises, or is covered by, a top layer (121), and/or the hollow vessel (117) is at least partially filled with a compressible material.

15. The medical apparatus (100) as in claim 1 which comprises a form body (127, 129) arranged in the interior (I) of the pressure vessel (1) for receiving a distal section of the limb stump (KS), wherein an exterior surface of the form body (127, 129) frictionally contacts, at least in section, a surface of the membrane (5).

16. The medical apparatus (100) as in claim 15, wherein the form body (127, 129) is a multiple-part and/or module-shaped form.

17. The medical apparatus (100) as in claim 15, wherein the form body (127, 129) contains or comprises a compressible material (119).

18. A set, comprising
   at least a medical apparatus (100) as in claim 1; and
   at least two membranes (5) which are at least in one aspect different from each other and/or at least a weight to temporarily increase or load or add to the weight of the patient and/or at least a release unit, and/or at least an adaptor (207) for releasably connecting or fixing the limb stump (KS) to or at the pressure vessel (1).

19. The set of claim 18, further comprising at least one adherent stocking (215) to cover and/or to be pulled over the limb stump (KS), wherein the adherent stocking (215), which is connected to the limb stump (KS) in a force-closure or frictional manner, is connected to a surface of the membrane (5) at or in the pressure vessel (1).

20. A method for fitting a plaster impression to a limb stump (KS) or for measuring the dimension of the limb stump (KS) of a patient encompassing the steps of:
   providing a medical apparatus (100);
   filling the fluid chamber or the pressure chamber (DK) of the pressure vessel (1) with a liquid (F), or changing a liquid level within the fluid chamber or the pressure chamber (DK), such that the membrane (5), at least in sections thereof, is covered with or by the liquid (F) around the entire circumference of these sections, or such that the membrane (5) cambers through the insertion opening (9) of the pressure vessel (1) outwardly into the exterior (Ä) of the pressure vessel (1).

21. The method as in claim 20 encompassing the further step of:
   regulating or controlling how deep the limb stump (KS) has been inserted as is being intended into the pressure vessel (1), by opening and/or closing the outlet (19, 19') or the valve or stopcock, and/or adjusting a length of the connector (53) such that a floating of the membrane (5) caused by fluid in a pressure chamber (DK) is such that a contact point surface (83) between the limb stump (KS) and membrane (5) is on the same height level (H) as a transition section (85) at which the pressure chamber (DK) is just not formed by the wall (wall) anymore, but by the membrane (5).

22. The method as in claim 20 encompassing the further step of:
increasing the pressure prevailing in the fluid chamber or pressure chamber (DK) of the pressure vessel (1).

23. A calculation device (200), programmed, configured and/or set to execute the method or parts of the method according to claim 20.

24. A method for adjusting a plaster impression to a limb stump (KSO or for measuring the limp stump (KS) of a patient encompassing the steps of:
Providing a medical apparatus (100) as in claim 1;
Inserting the limb stump into the membrane (5) such that the limb stump (KS) is covered or surrounded or enclosed at least in sections thereof by the membrane (5) around its entire circumference;
Determining, via a pressure measuring device, the pressure prevailing on the membrane (5), in the pressure chamber (DK), on a section of the surface of limb stump (KS), the latter being covered during use of the apparatus (100) by the membrane (5), and/or between membrane (5) and limb stump (KS);
Determining a weight with which the patient, whose limb stump (KS) is inserted into the medical apparatus (100), should be weighted in order for the pressure, measured by the pressure measuring device, to be in a pre-determined target value range.

25. A method for determining an additional weight while adjusting a plaster impression to a limb stump (KS) or while measuring the limb stump (KS) of a patient, encompassing the steps of:
providing patient-related data;
entering the patient-related data into the detection device (97);
detecting, based on the patient-related data, a weight with which the patient, whose limb stump (KS) is inserted into the medical apparatus (100) according to claim 1, should be weighted such that the pressure prevailing on the membrane (5), in the pressure chamber (DK), on a section of the surface of limb stump (KS), the latter being covered during use of the apparatus (100) by the membrane (5), and/or between membrane (5) and limb stump (KS) be within a pre-determined target value range.

26. A unit (400) comprising at least a pressurization control device (410) for the pressure chamber (DK) of the medical apparatus (100) and at least a medical apparatus (100) according to claim 1, wherein the pressurization control device (410) comprises:
a pressure reservoir connection or port (413);
a pressure-control valve (414); and
at least one connection (417, 421) to or at the pressure chamber (DK) with a regulating valve (419, 423) for increasing pressure and/or with a regulating valve (419, 423) for decreasing pressure in the pressure chamber (DK).

* * * * *